US005647350A

United States Patent [19]
Mutch et al.

[11] Patent Number: 5,647,350
[45] Date of Patent: Jul. 15, 1997

[54] CONTROL OF LIFE SUPPORT SYSTEMS

[75] Inventors: William Alan C. Mutch; Gerald Robin Lefevre, both of Winnipeg, Canada

[73] Assignee: University of Manitoba, Winnipeg, Canada

[21] Appl. No.: 404,464

[22] Filed: Mar. 15, 1995

[30] Foreign Application Priority Data

Mar. 15, 1994 [GB] United Kingdom ............... 9405002

[51] Int. Cl.$^6$ ............................................. A61M 16/00
[52] U.S. Cl. .............................. 128/204.21; 128/204.23
[58] Field of Search ........................ 128/204.23, 204.21

[56] References Cited

U.S. PATENT DOCUMENTS

| 4,001,700 | 1/1977 | Cook et al. ............ 128/204.21 X |
| 4,584,996 | 4/1986 | Blum ....................... 128/204.21 |

FOREIGN PATENT DOCUMENTS

| 2 624 744 | 6/1989 | France . |
| 2 025 662 | 1/1980 | United Kingdom . |
| WO93/10844 | 6/1993 | United Kingdom . |

OTHER PUBLICATIONS

Maeda, K. et al., Asaio Transactions, "Predictive Control By Physical Activity Rate Of A Total Artificial Heart During Exercise", vol. 34, No. 3, Jul. 1988, 480–484, XP 000053170.

Primary Examiner—Vincent Millin
Assistant Examiner—Eric P. Raciti
Attorney, Agent, or Firm—Sim & McBurney

[57] ABSTRACT

The flow of a biological fluid to an organ is computer-controlled so that the natural variation of such flow is simulated. Specifically described are control of a blood pump flow output during CPB to mimic normal pulsatile blood flow from the heart and control of a ventilator output to mimic normal breathing of healthy lungs. A pattern of variation over time of instantaneous flow of a biological fluid to an organ of a mammalian species is established, a variable control parameter for regulation of flow of the biological fluid to the organ is generated in accordance with the pattern, and the flow of biological fluid to the organ is controlled in accordance with the variable control parameter.

3 Claims, 39 Drawing Sheets

DAS16 'JUMPER BOX'

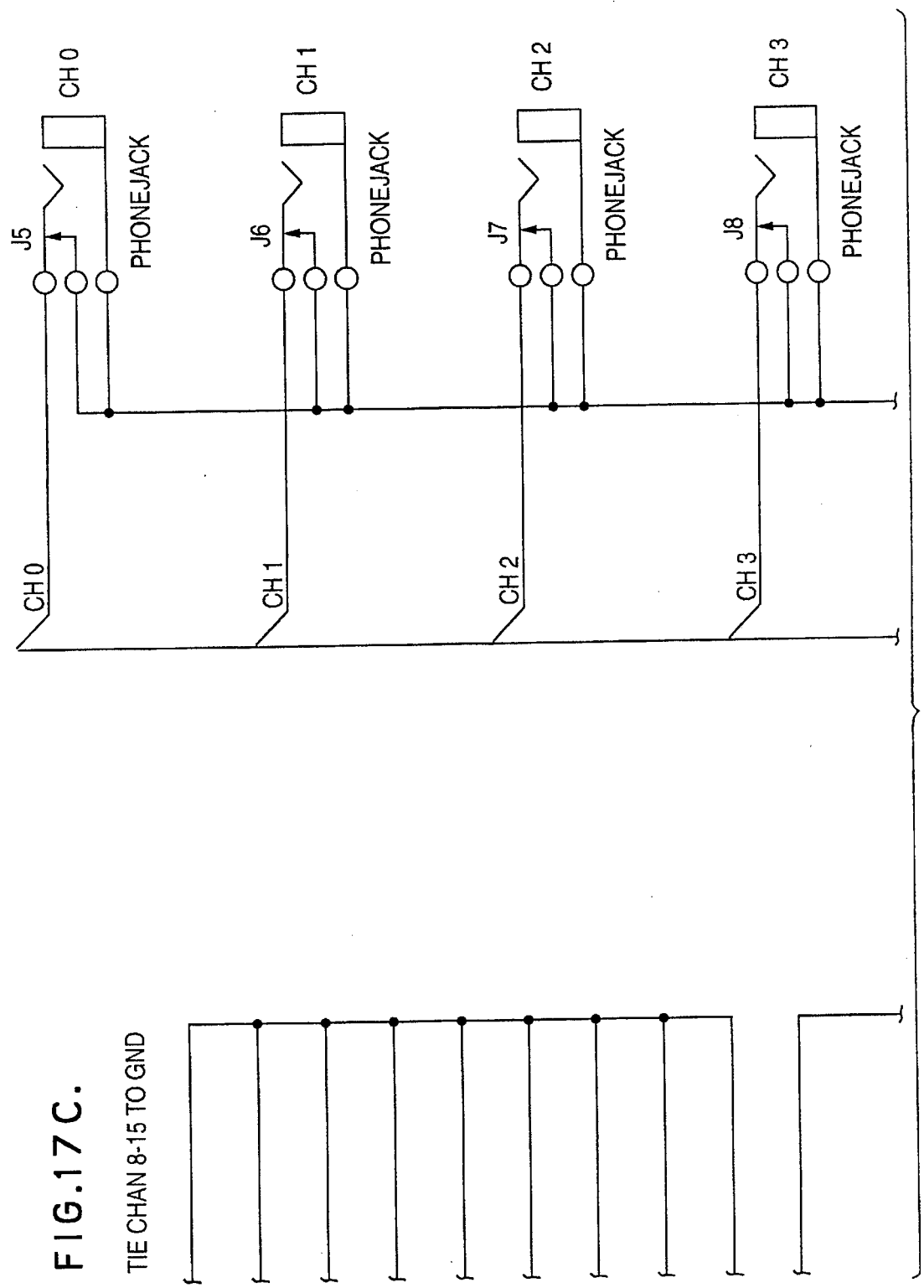

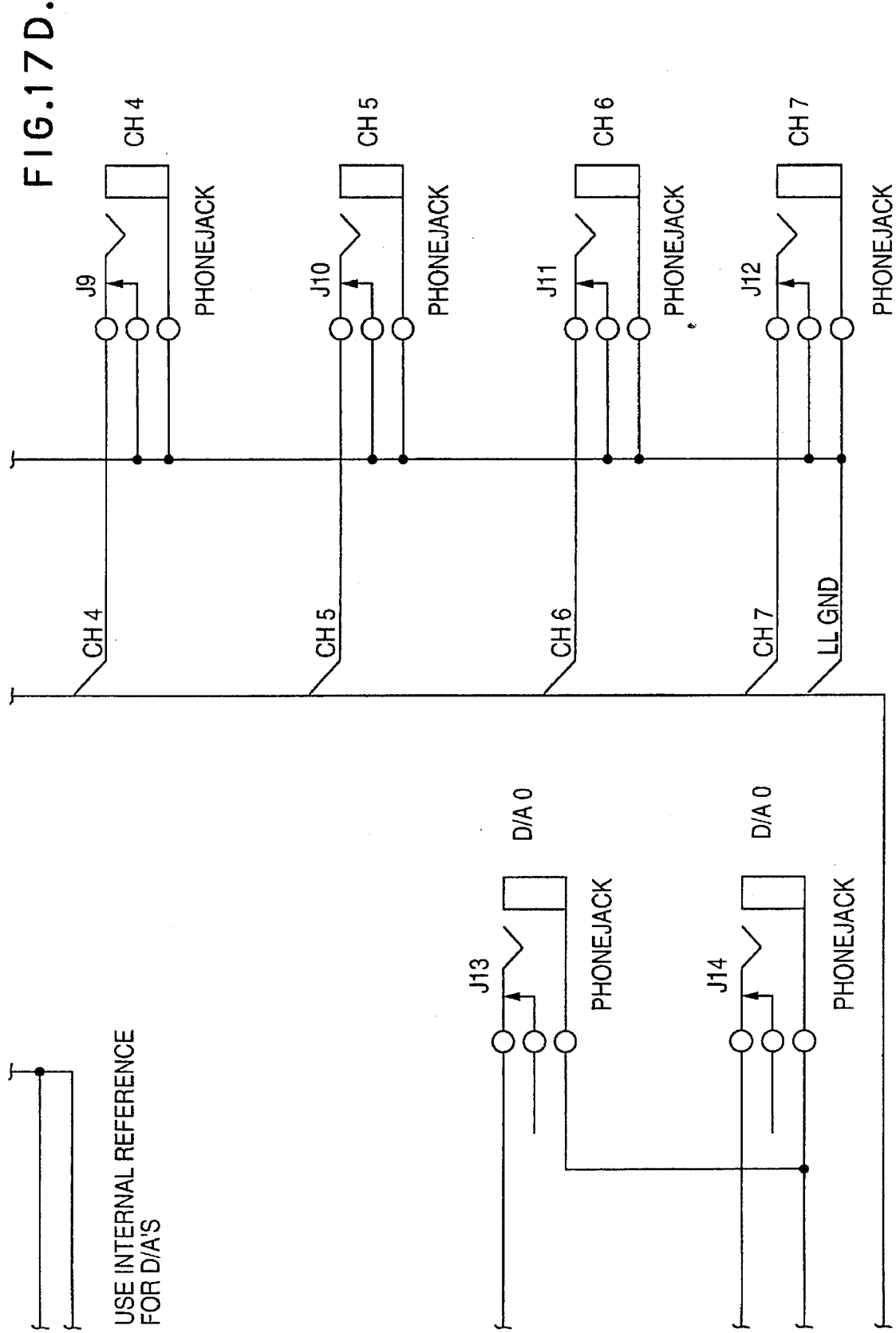

CONTROL OF LIFE SUPPORT SYSTEMS

FIELD OF INVENTION

The present invention relates to medical life support systems, and, in particular, to the control of cardiopulmonary bypass pumps for open heart surgery and mechanical ventilators to lungs.

BACKGROUND TO THE INVENTION

During cardiopulmonary bypass surgery (CPB), the most common operation conducted in North America, the heart is stopped and the blood which normally returns to the right side of the heart passes through a pump and oxygenating system and is returned to the aorta, thereby bypassing the heart and lungs. The flow of blood is essentially non-pulsatile with a low amplitude waveform having monotonous regularity.

Although a common procedure (in excess of 400,000 open heart procedures per annum are conducted in North America) and although tremendous strides have been made so that open heart surgery is safer for patients, the procedure is not without its dangers. Although the vast majority of patients have marked improvement in their cardiac functional status following their procedure, of concern is the potential for damage to other organ systems which can occur due to the need for CPB.

The following consequences have been identified with conventional non-pulsatile CPB, namely metabolic acidosis, interstitial fluid accumulation, elevated systemic vascular resistance, arteriovenous shunting and impaired brain oxygenation. Of greatest concern is the potential for neurologic damage. Increasingly, well conducted prospective trials have demonstrated an alarming rate of post-operative neuropsychologic disturbances following cardiac surgery. Recent studies have shown that up to 60 percent of patients undergoing open heart surgery have neuropsychologic deficits following their operation, so that as many as 240,000 patients per annum may develop neurologic abnormalities following cardiac surgery. These disturbances are subtle but involve higher cognitive functions of the brain.

Mechanical ventilation of the lungs represents one of the major accomplishments of modern medicine and is one of the cornerstones upon which modern surgery and intensive care is based. Despite many major advances, mechanical ventilation is still associated with a number of alterations in respiratory function which causes morbidity and mortality in patients requiring this type of support. Inability to maintain gas exchange remains one of the major limiting factors with regard to life-support of critically ill patients. Even in healthy patients being ventilated during elective surgery, alterations in gas exchange can be demonstrated. These relate to collapse of small airways and alveoli. Prevention of these alterations would likely represent a major advance in management of all patients requiring ventilatory support. Conventional mechanical ventilation is monotonously regular in delivery of set tidal volume and respiratory rate.

The monotonous regularity of pumping of blood during CPB and of set tidal volume and respiratory rate of a mechanical ventilator is in contrast to the intrinsic spontaneously variable rhythms of heart rate, blood pressure and respiration, associated with a normal functioning heart as well as the considerable range of tidal volume and respiratory rate which a healthy individual demonstrates during breathing.

SUMMARY OF THE INVENTION

In the present invention, the operation of a blood pump and mechanical ventilator are controlled to provide a flow of blood on the one hand and medical gases on the other which is varied in a manner that closely mimics the natural variation action of the heart and lungs and thereby overcomes some of the defects noted above. The invention is not applicable only to these two devices but is applicable to regulation in control of flow of any biological fluid to any organ. Although the existence of such variability in biological fluid flow is known, no one has heretofore taken such variability into account during the application of life support systems.

Blood is pumped in a monotonously regular non-pulsatile fashion or low amplitude pulsatile manner.

In the present invention, a pattern of variations over time of instantaneous changes in flow of a biological fluid to an organ of a mammalian species first is generated. The mammalian species may be the human to whom the procedure is to be applied, another human or another mammalian species which is a model for a human, such as, a dog or a pig. The generated pattern may be an actual pattern determined from the mammalian species or may be a computer simulation of the known variation in the flow. The generated pattern generally is provided with a sufficient number of determinations as to be representative of normal variation. Depending on the procedure involved, the pattern of variation may be established for the appropriate change in flow. For example, for control of blood pump during CPB, a pattern of variation over time of instantaneous blood pressure and heart rate is established. For control of a ventilator device, a pattern of variation over time of instantaneous respiratory rate and tidal volume is established.

A variable control parameter then is generated for regulation of flow of the biological fluid to an organ in accordance with the pattern. This control parameter is most readily achieved by computer processing of the pattern of variation. In effecting such computer processing, the individual values of the parameter in the pattern and the peak-to-peak time interval between the individual values are recorded and analyzed. For example, for control of a CPB pump, each of the individual blood pressures for the pattern of instantaneous blood pressure and heart rate and the time interval (heart rate) between each of the individual blood pressures are recorded. For control of a ventilator, each of the individual respiratory rates and tidal volumes for the pattern of instantaneous respiratory rate and tidal volumes and the time interval between each of the individual respiratory rates and tidal volumes are recorded.

The variable control parameter generated in the procedure of the invention depends on the flow of biological fluid being regulated. In the case of the CPB pump, a signal is generated corresponding in value to an individually-determined blood pressure for a period of time corresponding to the heart rate for the difference between the one individually-determined blood pressure and the next individually-determined blood pressure of the pattern. In the case of the ventilator, a signal is generated corresponding in value to an individually-determined respiratory rate and tidal volume.

In the present invention, the next step is to control the flow of biological fluid to the organ in accordance with the variable control parameter. In this way, the flow of biological fluid to the organ is effected in accordance with the pre-established pattern of variation and hence mimics the natural flow of the biological fluid to the organ.

The manner of control of the flow of biological fluid to the organ depends on the biological fluid and the organ concerned. For example, in the case of the control of a CPB pump, a control voltage is generated corresponding in magnitude to the generated signal from the variation pattern and the control voltage is applied to the pump to provide an output of blood from the pump of a pressure proportional to the magnitude of the signal for the period of time (peak-to-peak time interval). The steps of generating a signal, generating a control voltage and applying the control voltage to the pump then is repeated for each next individually-determined blood pressure of the pattern. Depending on the duration of the operation and the number of individual determinations in the pattern, it may be necessary to repeat these steps again for the pattern, reading either from the beginning or in the reverse direction. In this way, a pulsatile flow of blood from the pump is provided to the CPB patient which mimics normal pulsatile blood flow from the heart.

Similarly, for the control of ventilating gas from a ventilator, a control voltage is generated corresponding in magnitude to the generated signal from the variable pattern and the control voltage is applied to the ventilator device to provide an output of ventilating gas from the ventilator device of a respiratory rate proportional to the magnitude of the signal. The steps of generating a signal, generating a control voltage and applying the control voltage to the ventilation device are repeated for each next individually-determined respiratory rate of the pattern. In this way, a variable flow of ventilating gas from the ventilator device is provided which mimics normal breathing of healthy lungs.

As noted above, the present invention is applicable not only to control of a CPB pump or a mechanical ventilator but also to any other operation or device involving this control of a biological fluid to any organ. For example, the principles of the invention may be used in intra aortic balloon counterpulsation (IABC), the technique used to support patients, usually following CPB, when they are unable to maintain adequate cardiac output, until enough heart function has returned to permit its discontinuation.

The principles of the invention may be employed to improve hemodialysis by introducing variability to the pumping to provide improved diffusion across the dialysis membrane by promoting better mixing of blood and avoidance of areas of relatively stagnant flow and thereby decreasing dialysis time.

In addition, the present invention may be employed with extracorporeal membrane oxygenation (ECMO), which is a modification of CPB in which bypass is instituted to support the patient while giving the lungs a chance to heal. The patient is ventilated while on ECMO and if the therapy is successful, eventually weaned off ECMO and the ventilator. Computer control of the CPB pump in this situation has the potential to enhance organ perfusion, while computer controlled ventilation has the potential to activate lung healing and of improving gas exchange in order to facilitate earlier weaning from ECMO.

The present invention further may be employed in conjunction with right and left ventricular assist devices (RVAD and LVAD), which are occasionally used to support patients after CPB when they are unable to maintain adequate output without this type of support. Patients given such support are simultaneously being ventilated. Computer-controlled ventilation and computer-controlled RVAD and LVAD, as provided herein, may improve organ perfusion while computer-controlled ventilation may indirectly influence hemodynamic variability.

Another application of the principles of the present invention is in the perfusion of organs prior to transplantation.

BRIEF DESCRIPTION OF DRAWINGS

Referring to FIG. 14, the wiper of the 'VOLUME' control is buffered by amplifier U1D, and coupled to a non-inverting summing amplifier (U1C), whose output is routed back to the 'VOLUME' control's original destination (label 'VOL CTRL' is connected to FIG. 13 amplifier U5D). The 'VOLUME' output at U1D is also routed to the A/D converter channel 0 input (U2A), and the 'VOL POT MONITOR' (U2B), which allows optional monitoring of the Ohio 7000's 'VOLUME' control level before modulation is inserted (J1 on FIG. 2). The modulation reference signal from the D/A converter channel 0 output is buffered and scaled (I1A and U1B) and routed to the other input of the non-inverting summing amplifier (U1C), whose output is also routed to A/D converter channel 1 input (U2C), and to U2D —the 'VOL MONITOR' (J2 on FIG. 12), which allow optional monitoring of 'VOLUME' after modulation is inserted. Since the D/A converter's output is in a range between 0 and 5 volts, the modulation level only increases the 'VOLUME', hence the position of the ventilator's 'VOLUME' control sets the minimum or baseline level of 'VOLUME'.

DESCRIPTION OF PREFERRED EMBODIMENT

Figure 1:
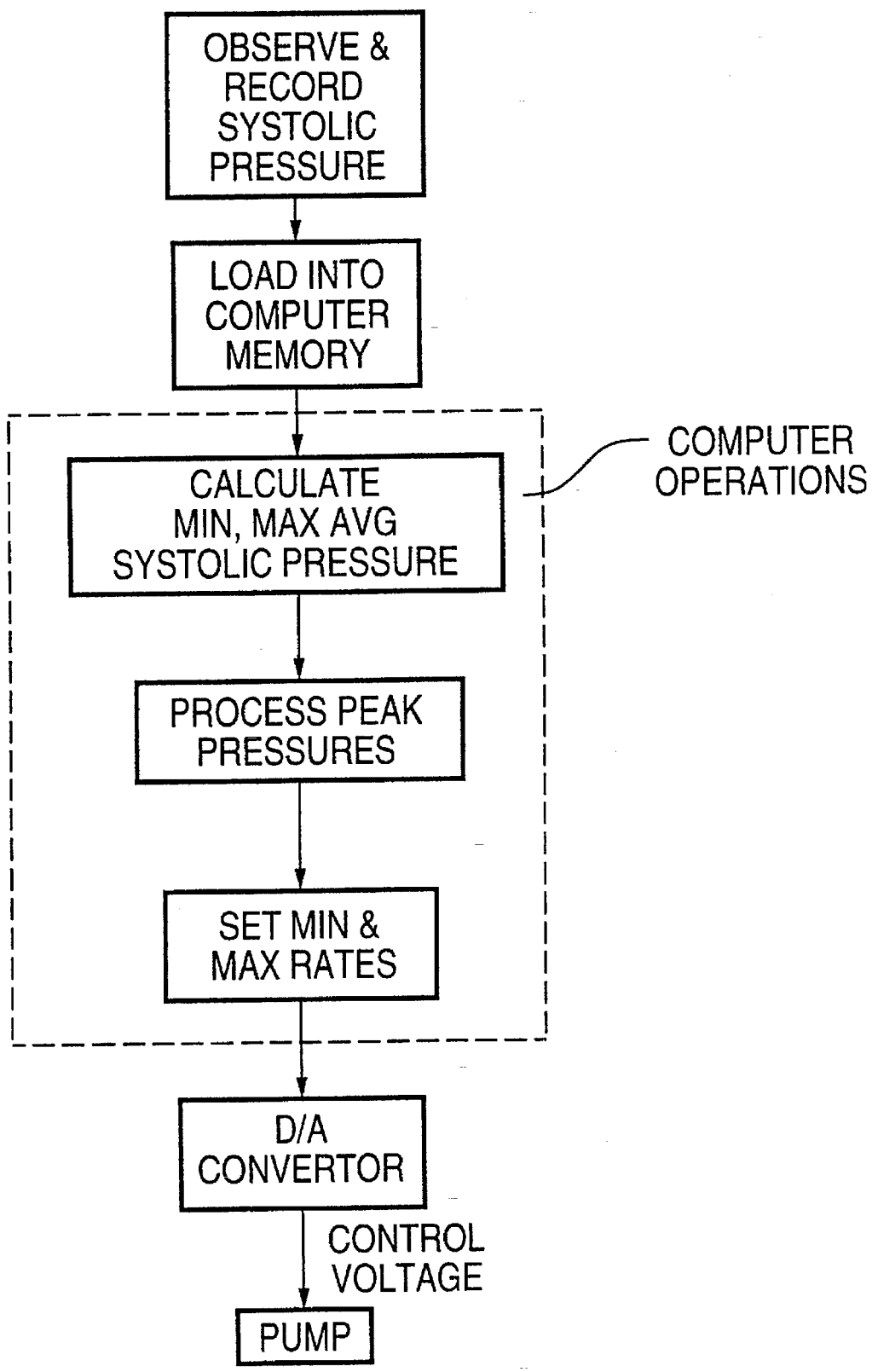
FIG. 1 is a flow diagram showing the various steps of the operation of a CPB pump in accordance with one embodiment of the invention.

In the following description of a preferred embodiment, there is description of the application of the present invention to control of a blood pump. However, it will be understood that the principles described with respect to such blood pump embodiment apply to other devices, including control of ventilators as described elsewhere. The steps involved are shown schematically in FIG. 1.

During a CPB procedure, an electrically-driven pump is used to maintain blood flow, as described above. Generally, a roller pump is employed for this function, in which a pair of diametrically opposed rotating arms engage a flexible tube through which blood is forced by the action of the arms engaging the flexible tube.

Figure 2:
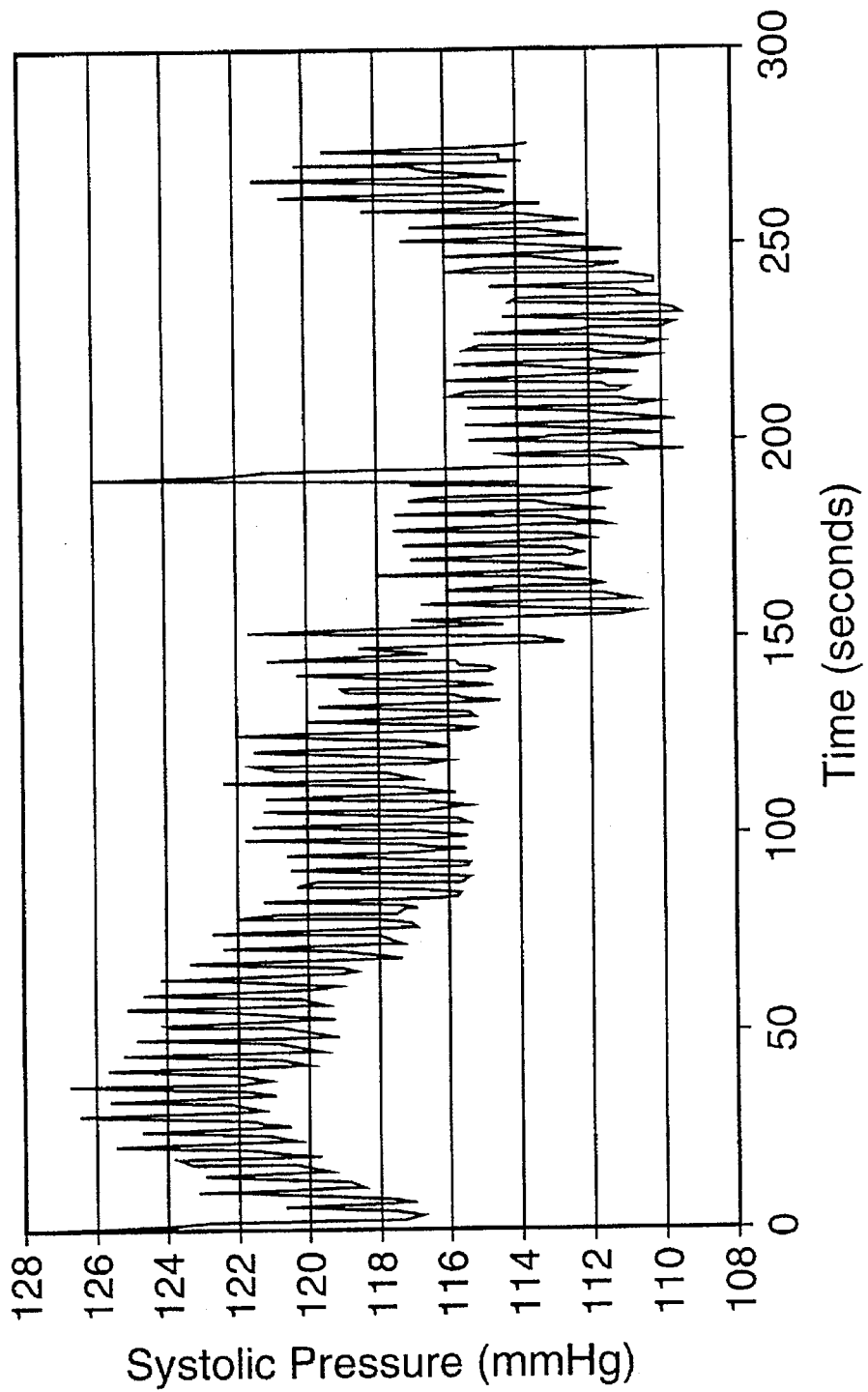
FIG. 2 shows a typical plot of natural variation of systolic blood pressure over time. In this instance, in a dog, data is captured to a data acquisition system from a dog. Following processing, these data are used as an input file for the computer controller used to vary roller pump head revolutions/min based on variability in beat-to-beat intervals and pressure.

An input file for a computer-controller for the pump first is established for the variation of systolic pressure with time for a typical animal, such as a human, a dog or a pig. A typical plot of the gross variation of systolic pressure in mm Hg over time is shown in FIG. 2.

This information, which may contain many thousands of observations of systolic pressure, is loaded into the computer memory and processed by peak height analysis. In this peak height analysis, the maximum, minimum average systolic pressures are determined and may be displayed, the minimum values are removed and the minimum, maximum and average of the remaining peak pressures is recalculated and, if desired, displayed. This information then determines the pulse pressure amplitude and beat-to-beat heart beat variation in the pattern.

Figure 3:
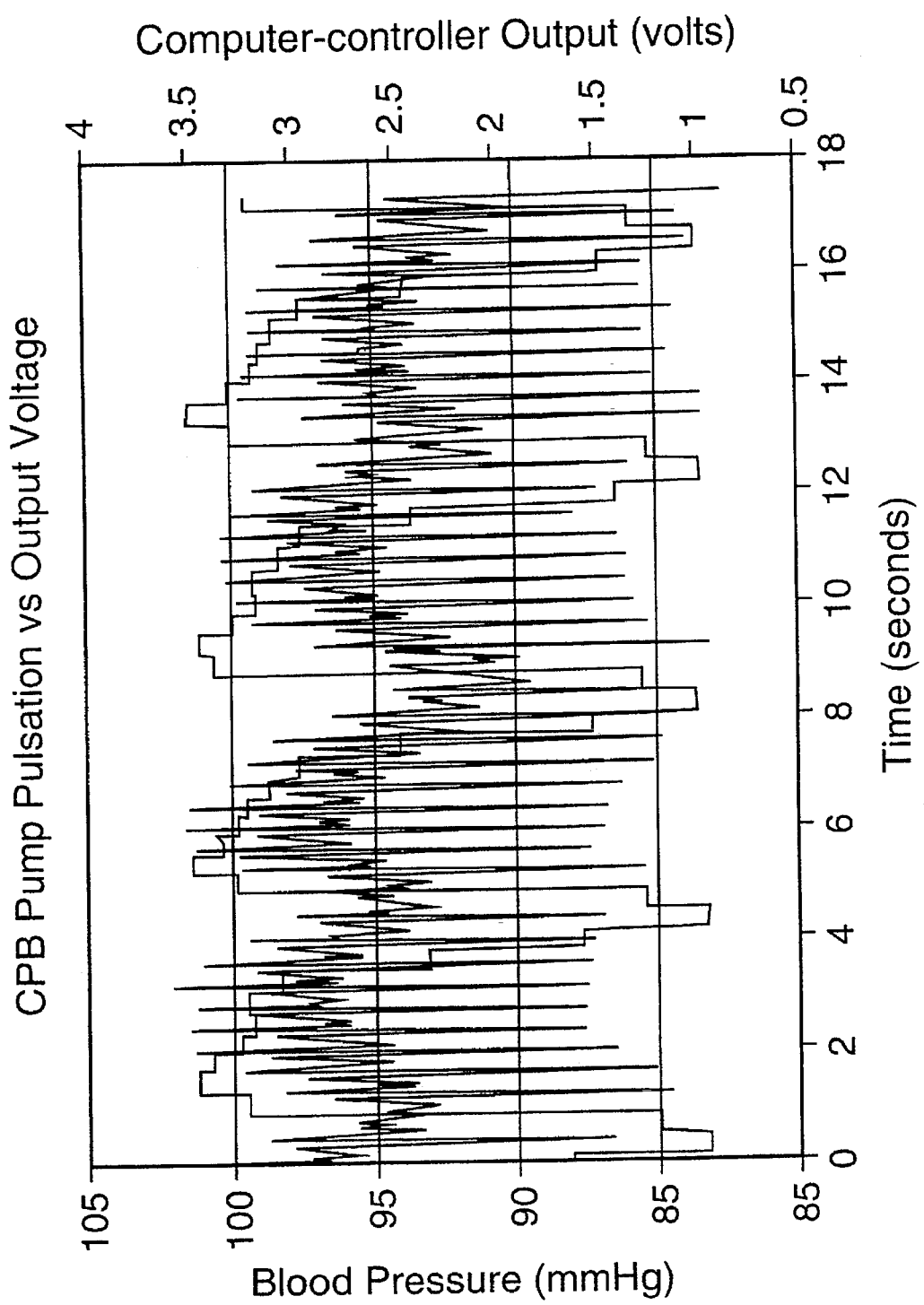
FIG. 3 shows a typical pump pulsation profile for a blood pump controlled in accordance with the invention superimposed upon a plot of peak-to-peak variations in blood pressure derived from a plot similar to that shown in FIG. 2.

The lowest and highest values of the pressure values from the peak-to-peak variation then are established and these values are used to set a minimum and maximum rate for the blood pump, respectively, which then determines the maximum amount of computer modulation. For example, a baseline pressure of 80 mm Hg with a 20 mm Hg variation may be established based on the input file, which then provides a peak pressure ranging from 80 to 100 mm Hg. The computer digital output signal corresponding in magnitude to a peak-to-peak value above the minimum is connected through a digital-to-analog (D/A) converter, which produces an analog voltage control signal to the blood pump to increase the blood pump rate. The computer generates a voltage on the D/A converter proportional to the peak pressure variations for a time proportional to the beat-to-beat interval. The voltage then is used to increase the rpm of the pump from the minimum or baseline setting. The data stored in memory is converted into time steps and relative amplitudes from 0 to 100%. For each time step, the D/A drive is held at the relative level until the next time step occurs. A typical pump pulsation profile superimposed upon a plot of peak-to-peak variations in blood pressure is shown in FIG. 3. As may be seen in FIG. 3, over a period of approximately 18 seconds, the computer-controller output varies between 1 and 3.5 volts. The changes in roller pump speed has resulted in escalations in blood pressure varying between 82 and 102 mm Hg. The data stored in memory is initially scanned in a forward direction for observations 1 to N. As necessary, the data is reverse scanned continuously from observations N−1 to 1 and then forwards from 2 to N. etc. until the program is terminated.

Figure 4:
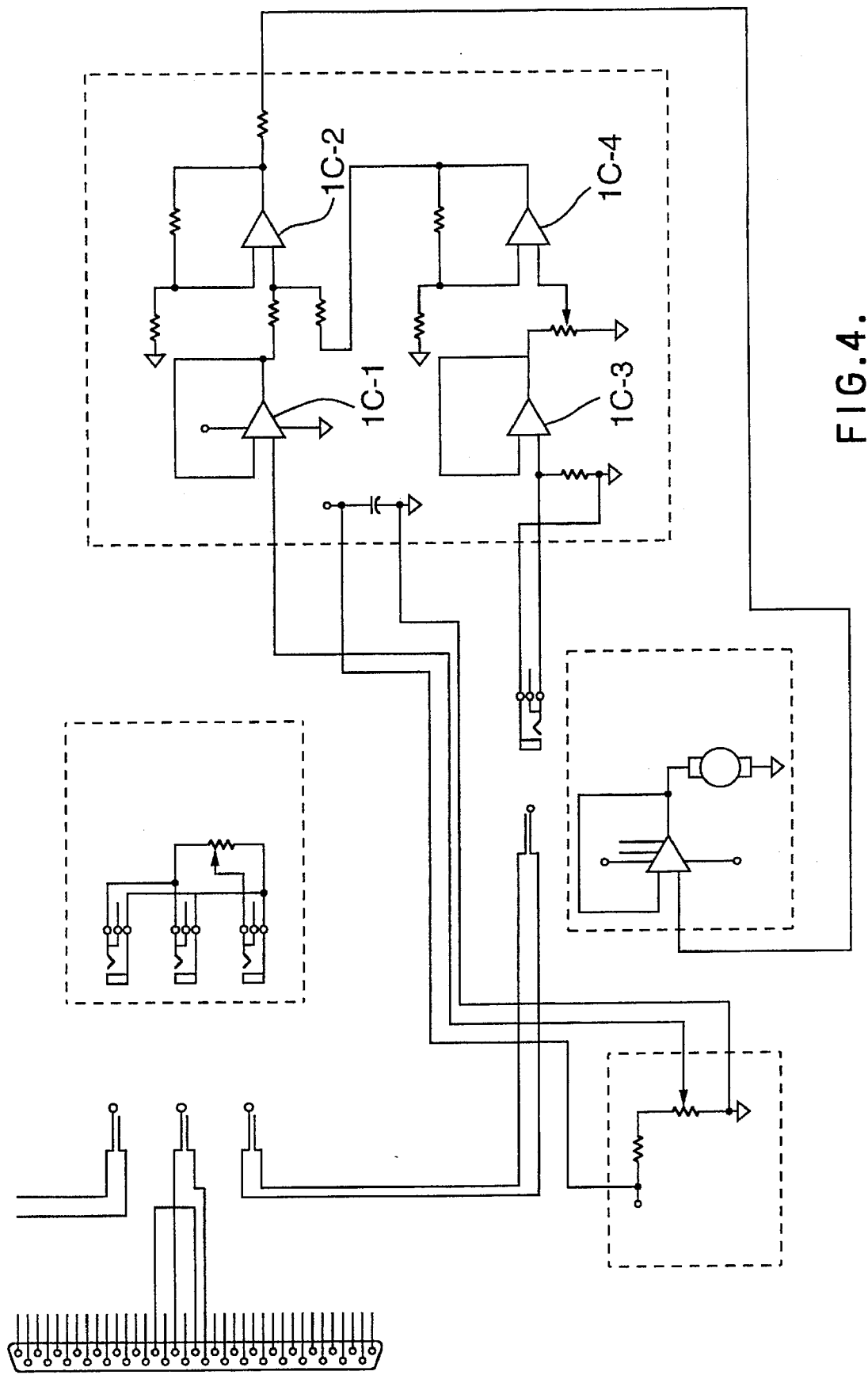
FIG. 4 shows typical circuitry for computer control of a blood pump motor according to the invention.
Figure 5:
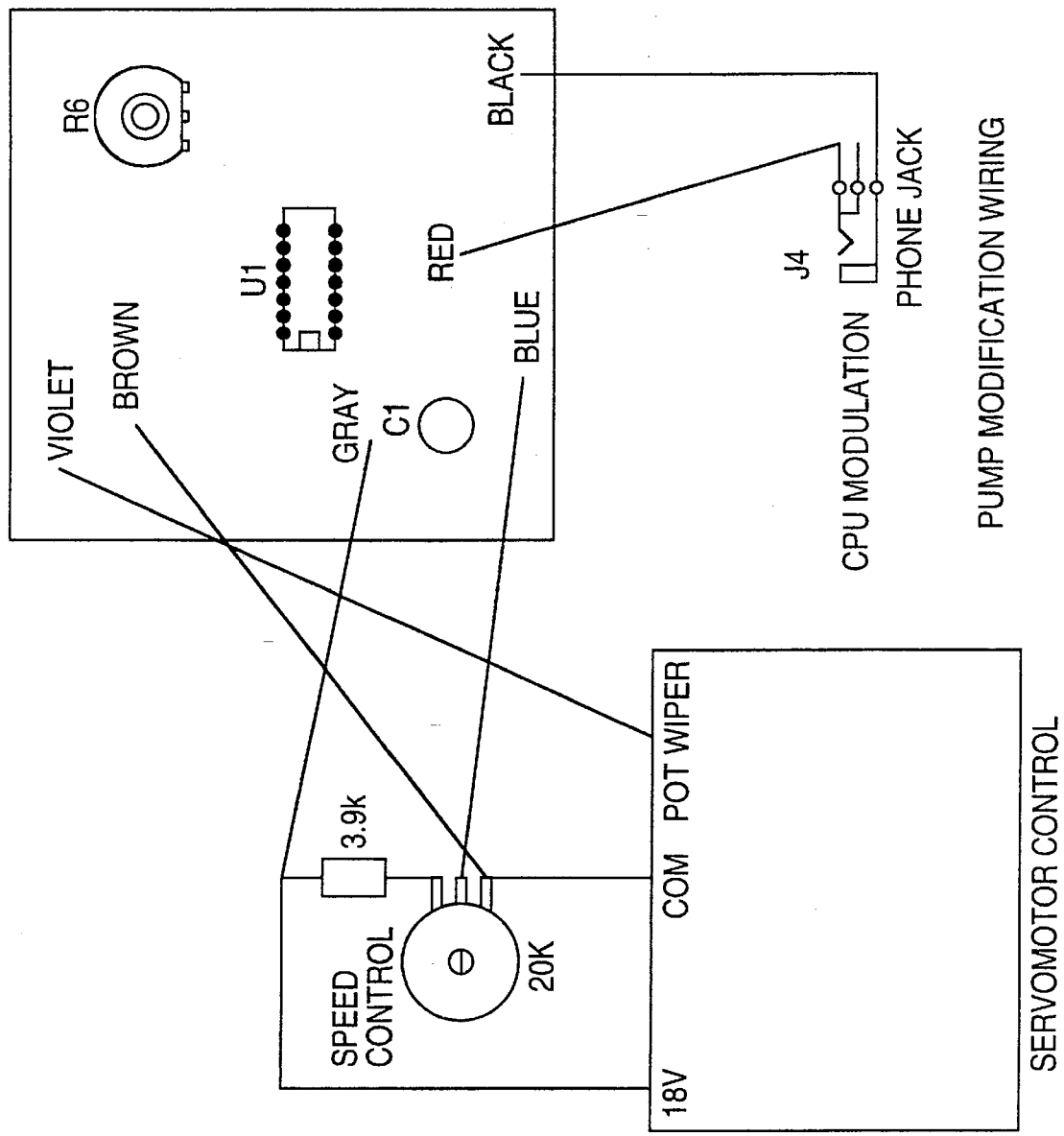
FIG. 5 shows a wiring diagram for a blood pump motor.

Any convenient form of the pump controller may be employed to receive the control signals from the computer and the corresponding voltage signals from the D/A converter. A typical circuitry is shown in FIG. 4 while a wiring diagram appears as FIG. 5. In this circuit, a non-inverting summing amplifier with input buffering is provided, power to operate the amplifier is from the roller pump rate controller. The signal from the original speed control is buffered by a buffer (IC-1), which is applied to one input of a summing amplifier (IC-2). The other input of the summing amplifier is received from the computer modulation signal received from the D/A converter via an external scaling box through buffer IC-3 and amplifier IC-4, which permits an increased voltage range, according to the desired multiple of the amplification, to be applied to the pump servo motor than provided by the D/A converter.

In this way, the roller pump revolutions/min are altered to recreate the pattern of spontaneous biologic variability in the heart function.

The computer operations described above may be effected on any convenient computer hardware programmed in any desired manner to effect the analysis described above to provide the blood pump control voltage. A program which may be employed, named Purfus, has the listing appearing in Table 1 below.

A configuration file, named Purfus Cfg, is necessary for the operation of Purfus program. This file contains a number corresponding to the base address of the D/A converter card:

| Decimal | Hex |
|---------|-------|
| 768 | 300 H |
| 784 | 310 H |
| 800 | 320 H |

Figure 6:
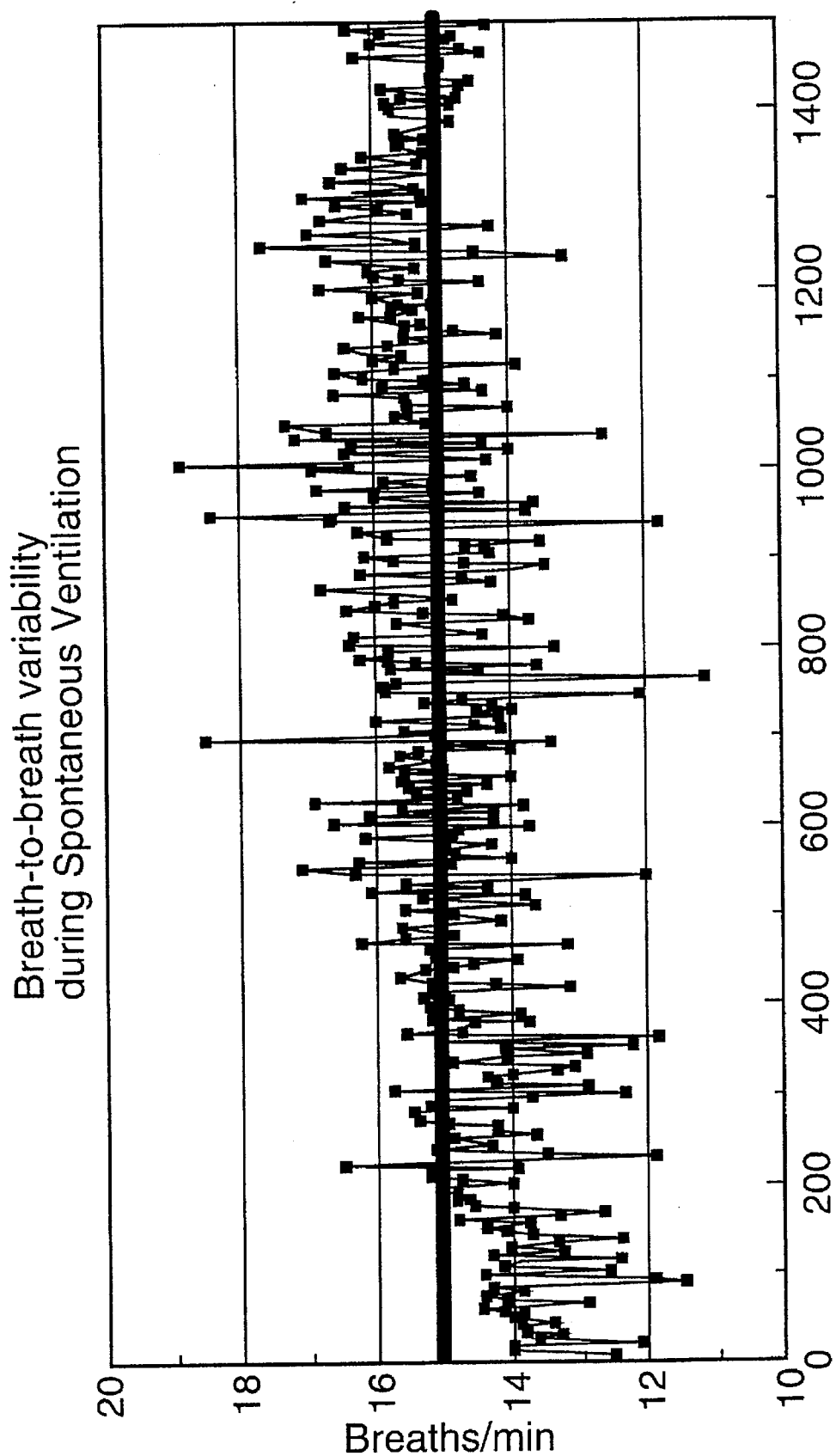
FIG. 6 shows the changes in respiratory rate (breaths/min) over time. Such data is used to create the input file for the ventilator computer controller. These data have a mean rate of 15 breaths/min.

Computer control of a ventilator to apply the principles of the invention thereto may be effected using the computer program shown in Table 2 below. This software allows the 'RATE' and the 'VOLUME' settings of the ventilator controls to be modulated independently via a data file, generated before hand and in a form such as appears in FIG. 6.

In order to implement computer control of the ventilator using the circuitry shown in FIGS. 11 to 17, a means of converting voltage to ventilation 'RATE' and 'VOLUME' is provided. A linear regression analysis of the ventilator's 'RATE' and 'VOLUME' potentiometers output voltage versus dial calibrations is performed ($R\hat{0}2 = 0.9996$). Functions are converted 'RATE' and 'VOLUME' into voltage, and vice-versa. By control loop scanning the A/D converter channel in the background using the high speed DMA facility, the current setting of the ventilator's 'RATE' control is acquired. If the modulation level for the current time step is greater than the baseline (set by the current setting of the ventilator's 'RATE' control), the D/A converter channel generates a voltage level, which is passed to the summing amplifier in the Ventilator Modulation Unit, necessary to increase the current baseline value of 'RATE' to the modulation level of 'RATE'. The output of the summing amplifier is then sampled by another A/D converter channel, converted into 'RATE', and displayed on the computer screen. The 'VOLUME' are updated in each 'loop' of the control program which executes every 400 milliseconds on a 'control' computer (a 4.77 MHz 8088 processor with a 8087).

EXAMPLES

Example 1

This Example illustrates the methods and materials used in ventilation experiments carried out on pigs.

Pig preparation:

Thirteen (13) pigs weighting 20 to 30 kg were studied. All pigs received atropine 0.6 mg and ketamine 10 mg/kg intramuscularly for induction of anesthesia. Once sedated, isoflurane in oxygen was administered by face mask. When airway reflexes had been obtunded, the pig was intubated with a 6.0 mm endotracheal tube. Mechanical ventilation was instituted with an Ohio 7000 anesthesia ventilator at 15 breaths/min with the minute ventilation adjusted to maintain the end-tidal $CO_2$ at 35 to 40 mm Hg. Isoflurane was administered at 2.0 percent end-tidal in oxygen during surgical preparation. Lactated Ringer's was infused IV at 10 ml/kg/hr during the experiment. Pancuronium bromide was administered IV intermittently for muscle relaxation.

The animal was turned supine and a cutdown performed in the groin. A double-lumen catheter was placed in the femoral artery for intermittent sampling of blood for arterial blood gases (ABG) and continuous recording of arterial pressure. A 7.5 Fr pulmonary artery catheter was inserted via the femoral vein and advanced with the balloon inflated until a pulmonary capillary wedge pressure (PCWP) was obtained. Pulmonary artery pressure was continuously recorded. Mixed venous blood was sampled from the distal end of the pulmonary artery catheter. Cardiac output (CO) was measured intermittently, by thermodilution, following 5 ml injection of room temperature saline (performed in triplicate). Following surgery, the animal was allowed to stabilize for 30 minutes and the isoflurane concentration was reduced to 1.5 percent end-tidal.

Baseline hemodynamic and respiratory measurements were then obtained. These included measurements of mean arterial pressure (MAP), mean pulmonary artery pressure (MPAP), PCWP, airway pressures at the proximal end of the endotracheal tube (all recorded to a Gould 2600 oscillograph and to an advanced CODAS data acquisition system), and CO. Gas measurements included arterial and mixed venous blood gases and end-expired gas sampled from the expiratory limb of the anesthesia circuit. These were measured using a Radiometer ABL3. Arterial and mixed venous oxygen content, oxygen saturation and hemoglobin concentration were measured with a Radiometer OSM3 set for porcine blood. All measurements were obtained in duplicate. Calculated indices included pulmonary vascular resistance (PVR), dead space ventilation (VD/VT) and shunt fraction (QS/QT).

Oleic Acid Lung Injury:

After the above measurements were obtained a Valsalva maneuver was done (mean airway pressure 30 cm $H_2O$ for 5 seconds). An infusion of oleic acid was started at 0.2 ml/kg/hr through the infusion port of the pulmonary artery catheter. At 5 min intervals the Valsalva maneuver was repeated and 1 min later an arterial blood gas obtained. The oleic acid infusion was continued until the $PaO_2$ decreased to $\leq 200$ mm Hg for 2 consecutive measurements. At this point the infusion was stopped and the volume infused noted. Following repeat hemodynamic and respiratory measurements as above, the animals were randomly allocated to one of two ventilatory modes; conventional IPPV with the respiratory rate (RR) fixed at 15 breaths/min with the minute ventilation (MV) changed to maintain $PaCO_2$ at $\leq 45$ mm Hg (control), or IPPV with a computer-controller with variable RR but with a mean of 15 breaths/min (computer). Again, MV was adjusted to maintain $PaCO_2$ at $\leq 45$ mm Hg. Ventilation continued with either the control or computer mode for the duration of the experiment. Every 30 minutes for 180 min, hemodynamic and respiratory data was obtained as above in duplicate. At 180 min, airway pressure data was acquired to the data acquisition system over a 2 min time period to sample approximately 30 consecutive breaths.

Figure 9:
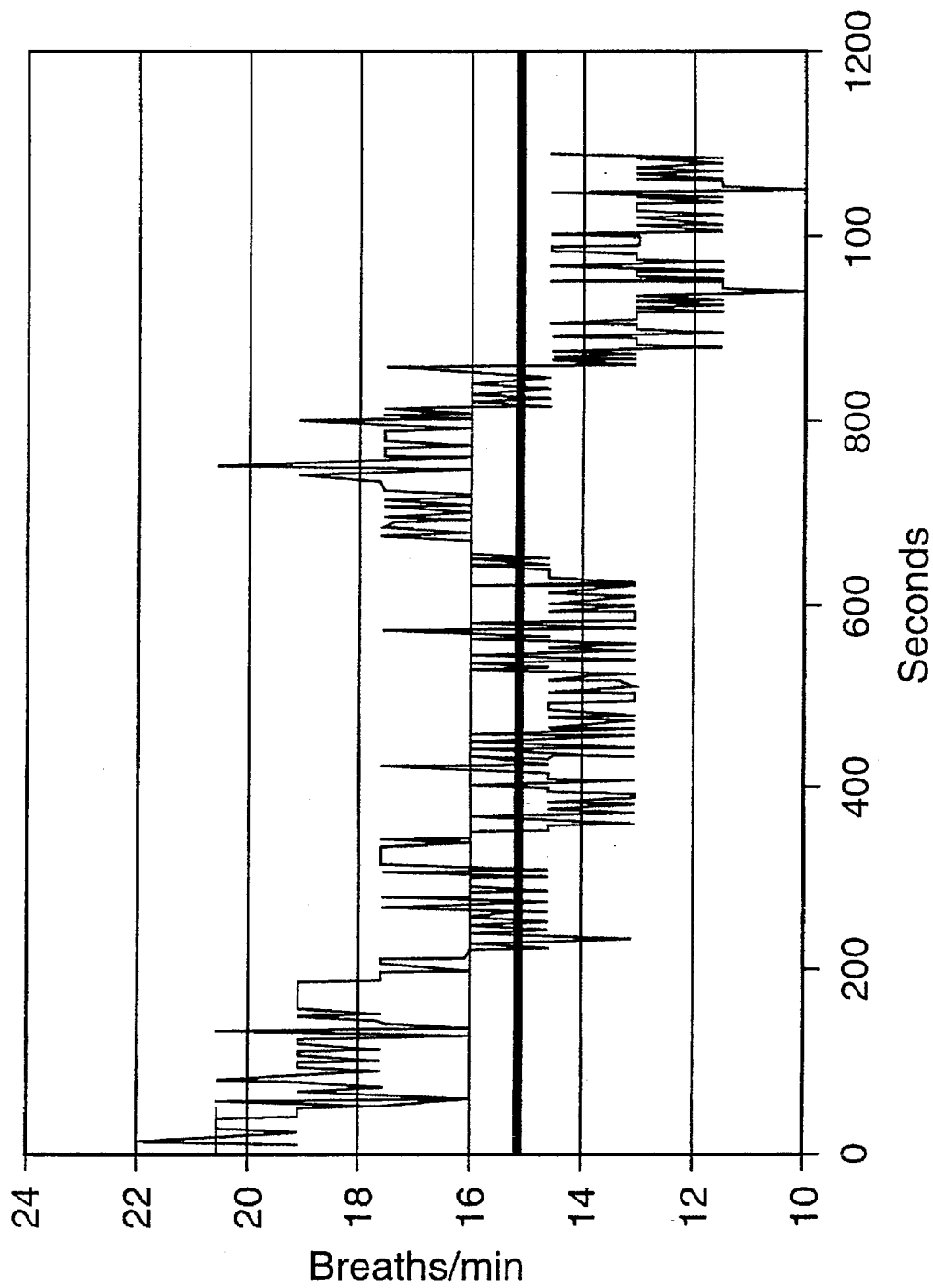
FIG. 9 is similar to FIG. 6 and shows the changes in respiratory rate (breathes/min) over time as well as the mean value.
Figure 10:
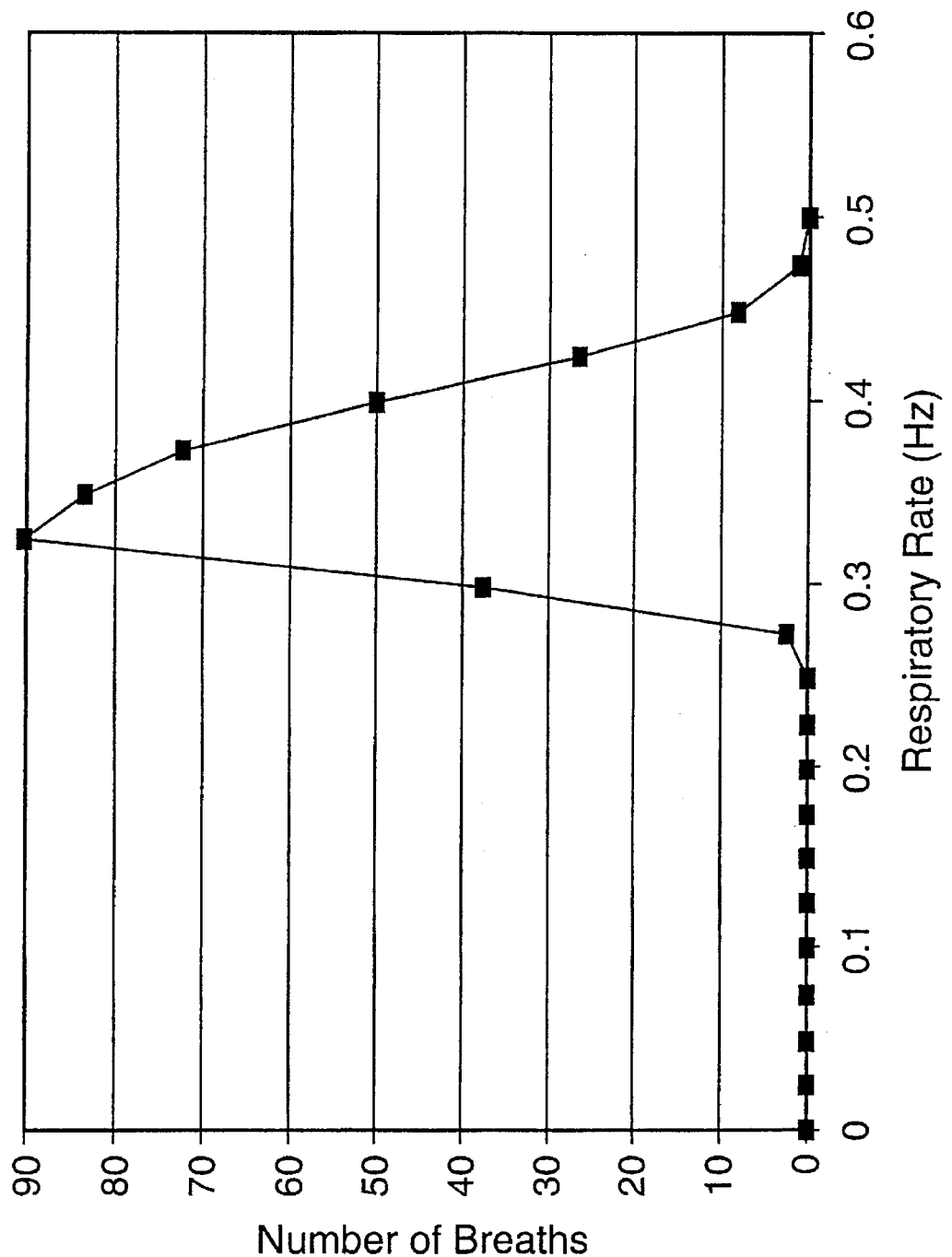
FIG. 10 shows a frequency vs respiratory rate plot devised from the graph of FIG. 9.
Figure 11:
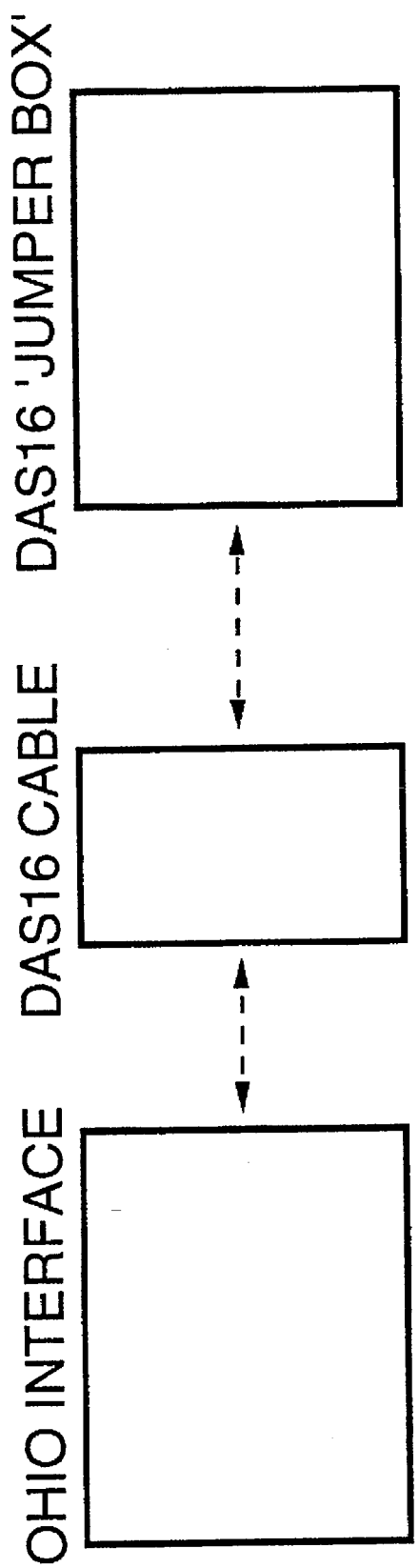
FIG. 11 is a block diagram showing the overall signal flow to the ventilator (Ohio 7000) used in the Examples described below. The 'Ohio Interface' module is connected to the Metrabyte DASH16 analog to digital (A/D) converter via bi-directional control lines via the 'DAS16 Cable' and 'DAS16 Jumper Box'.
Figure 12:
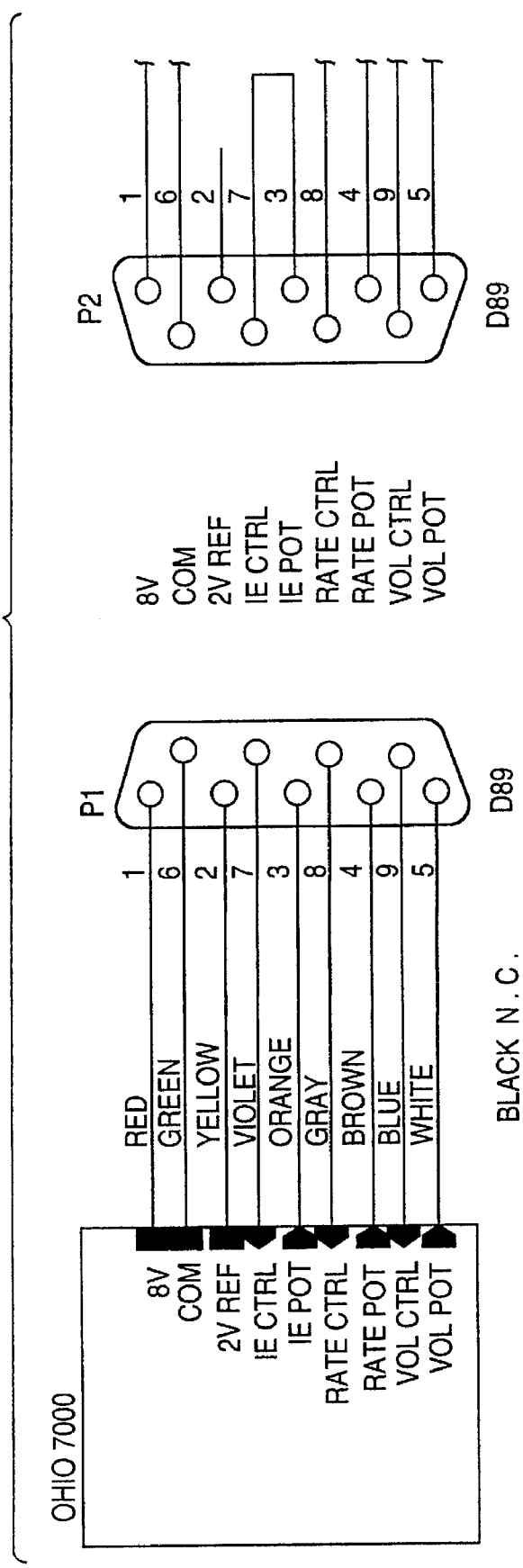
FIG. 12 is the internal wiring harness of the Ohio Interface Unit. Connector 'Pi' and module 'Ohio 7000' refer to the cable and modifications added to the Ohio 7000 Ventilator. This Figure shows all physical wiring connections of the electronic modules ('Volume Modulator' and 'Rate Modulator') to the switches and connectors. The Ohio 7000 supplies the power (8 V & COM). Connectors 'P2' and 'P3' are opposite gender. Experimental monitoring jacks ('J1' through 'J4') are for an external data acquisition system. Connector 'P3' interfaces to the Metrabyte model DASH16 A/D and digital to analog (D/A) converter. Switch S1 and S2 provide the ability to cancel 'RATE' or 'VOLUME' modulation individually ('manual' position) at any time.
Figure 12B:
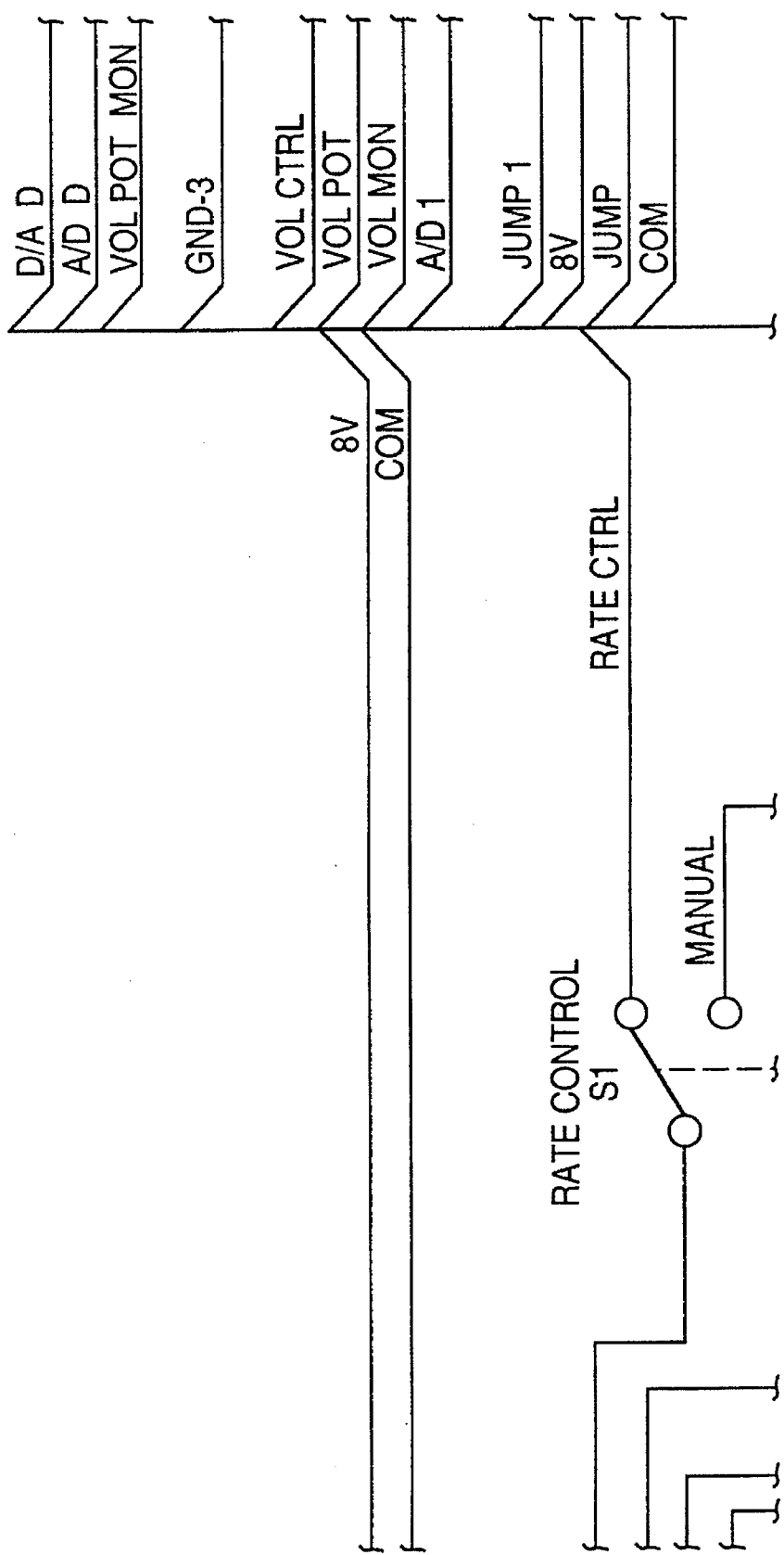
Figure 12C:
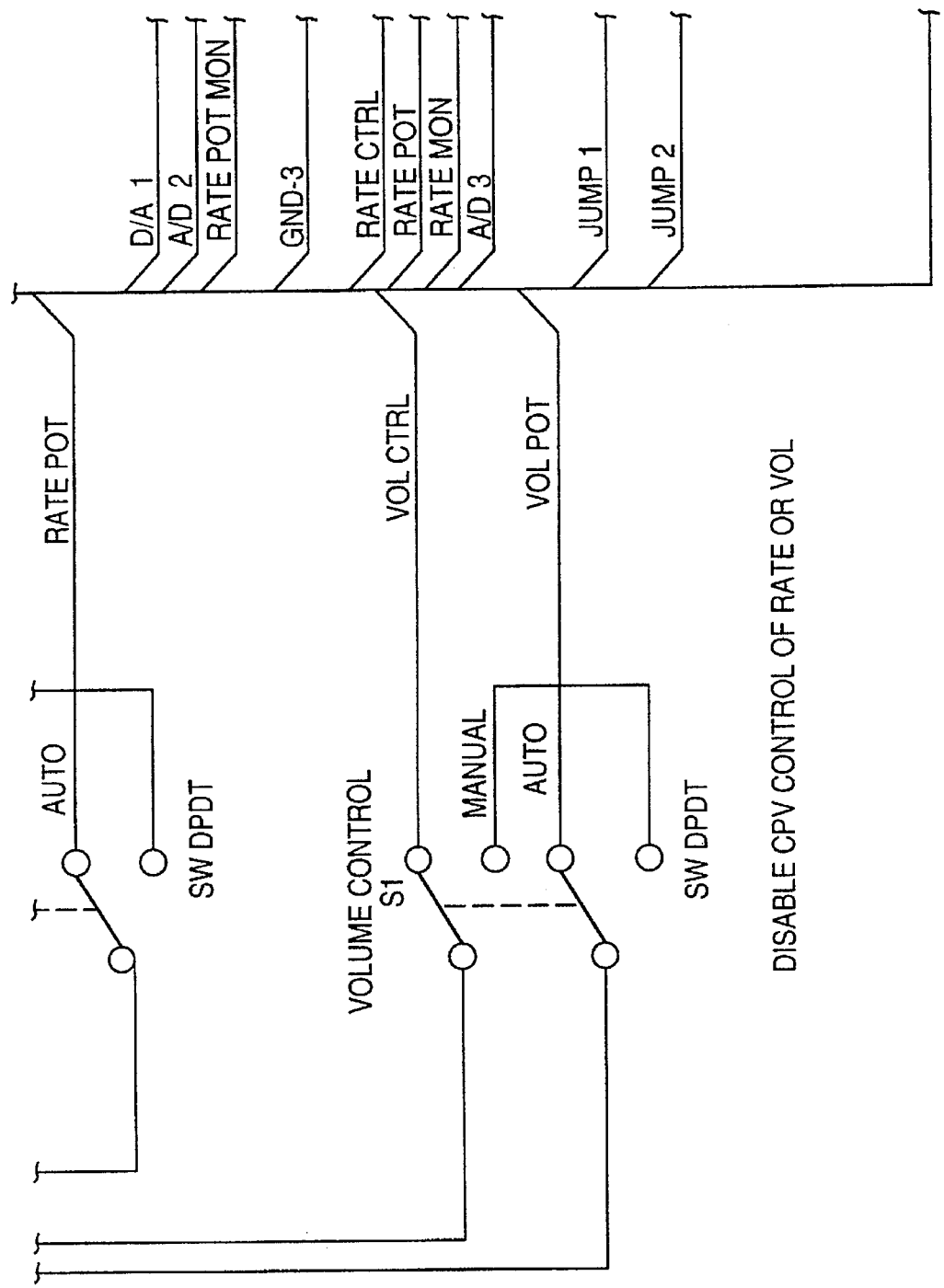
Figure 12D:
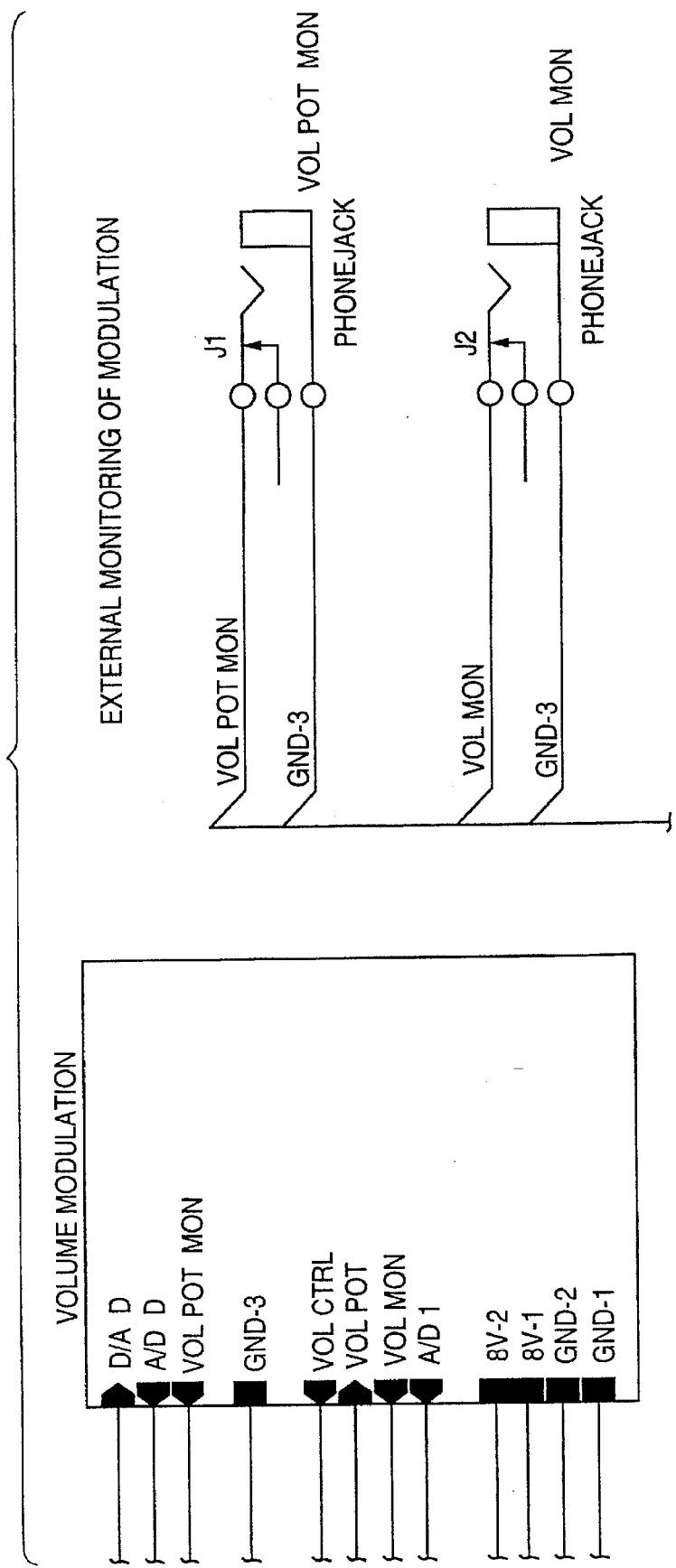
Figure 12E:
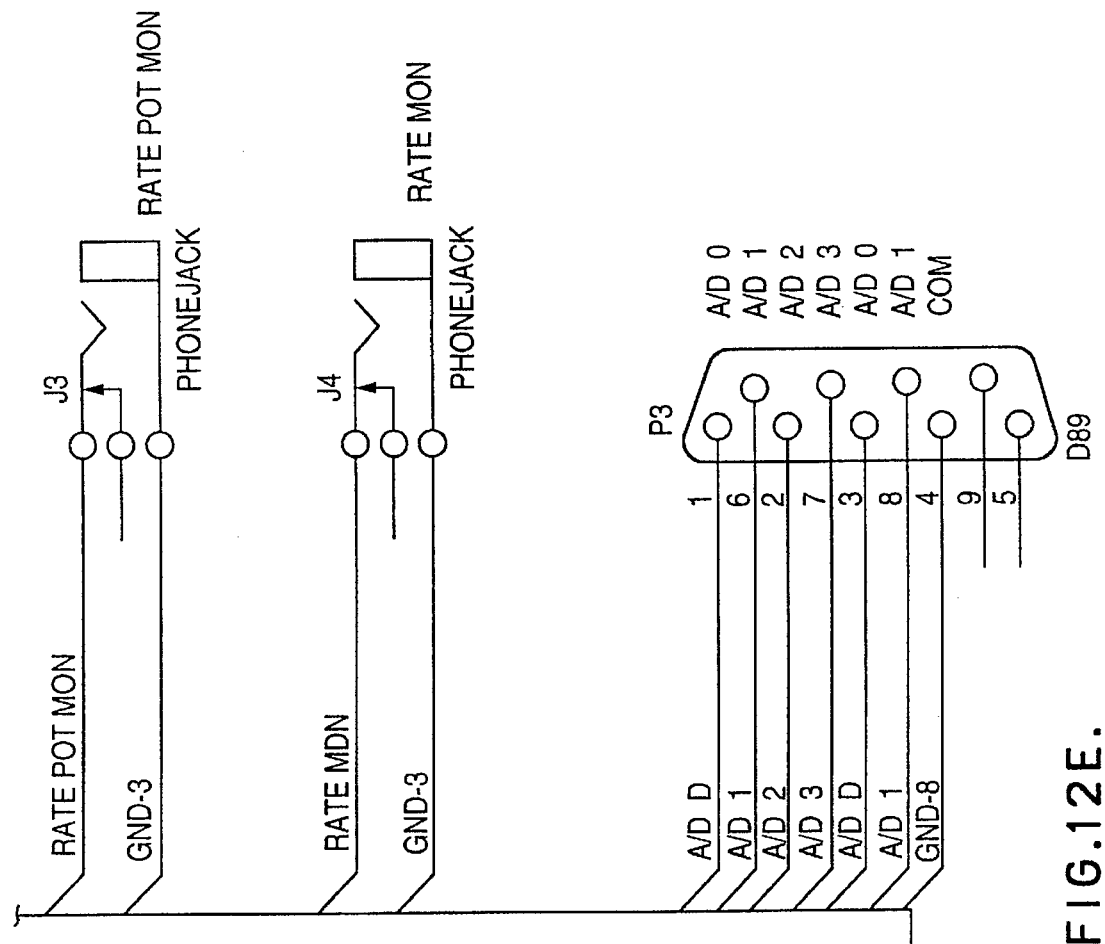
Figure 13:
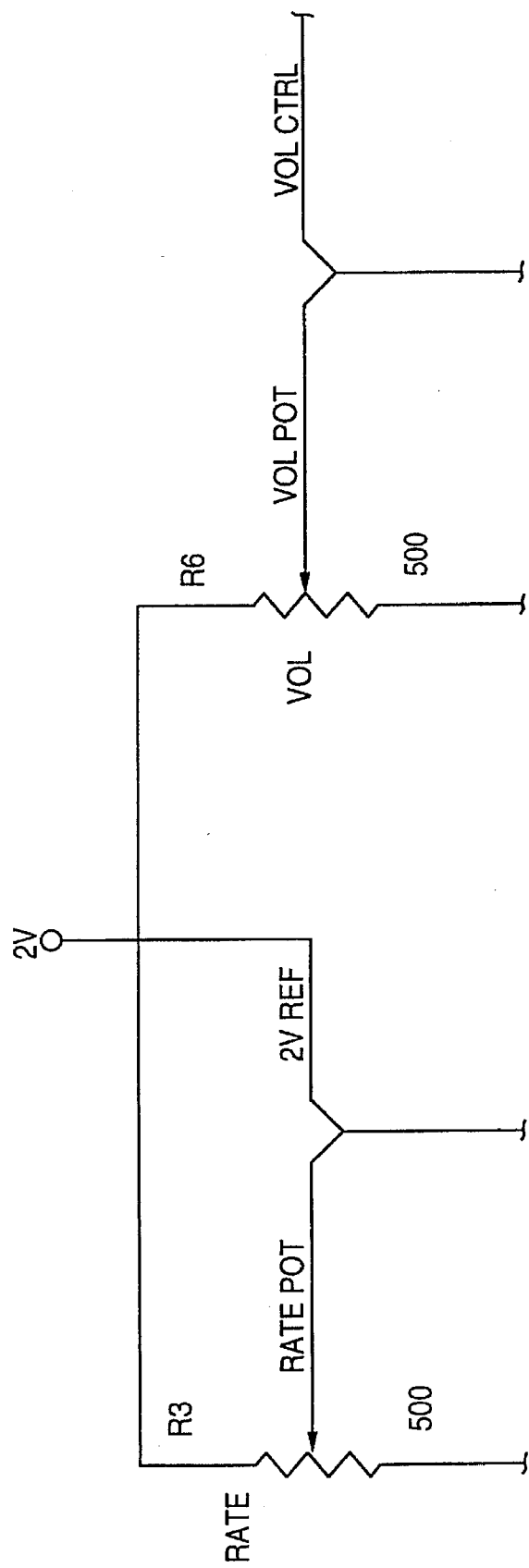
FIG. 13 displays an excerpt of the Ohio 7000 Ventilator control circuitry generated with an ohm meter and a photocopy of the service manual. Refer to the 'IE' ratio control R14. The control's wiper was originally connected to amplifier U22B. Modulation of the 'IE' control is introduced by inserting an external summing amplifier between the control and amplifier U22B (pins 3 and 7 of connector P4). Similarly, the 'RATE' and 'VOLUME' controls and their associated amplifiers (U22A and U5D) are routed to P4 pins 4 and 8, and 5 and 9 respectively. The 2 volt reference voltage for the 'RATE' and 'VOLUME' controls, as well as 8 volt supply and common are also routed to connector P4. Referring back to connector P2 in FIG. 12: external modulation of 'IE' was disabled (pins 3 and 7 jumpered), and the 2 volt reference (pin 2) was not required.
Figure 13B:
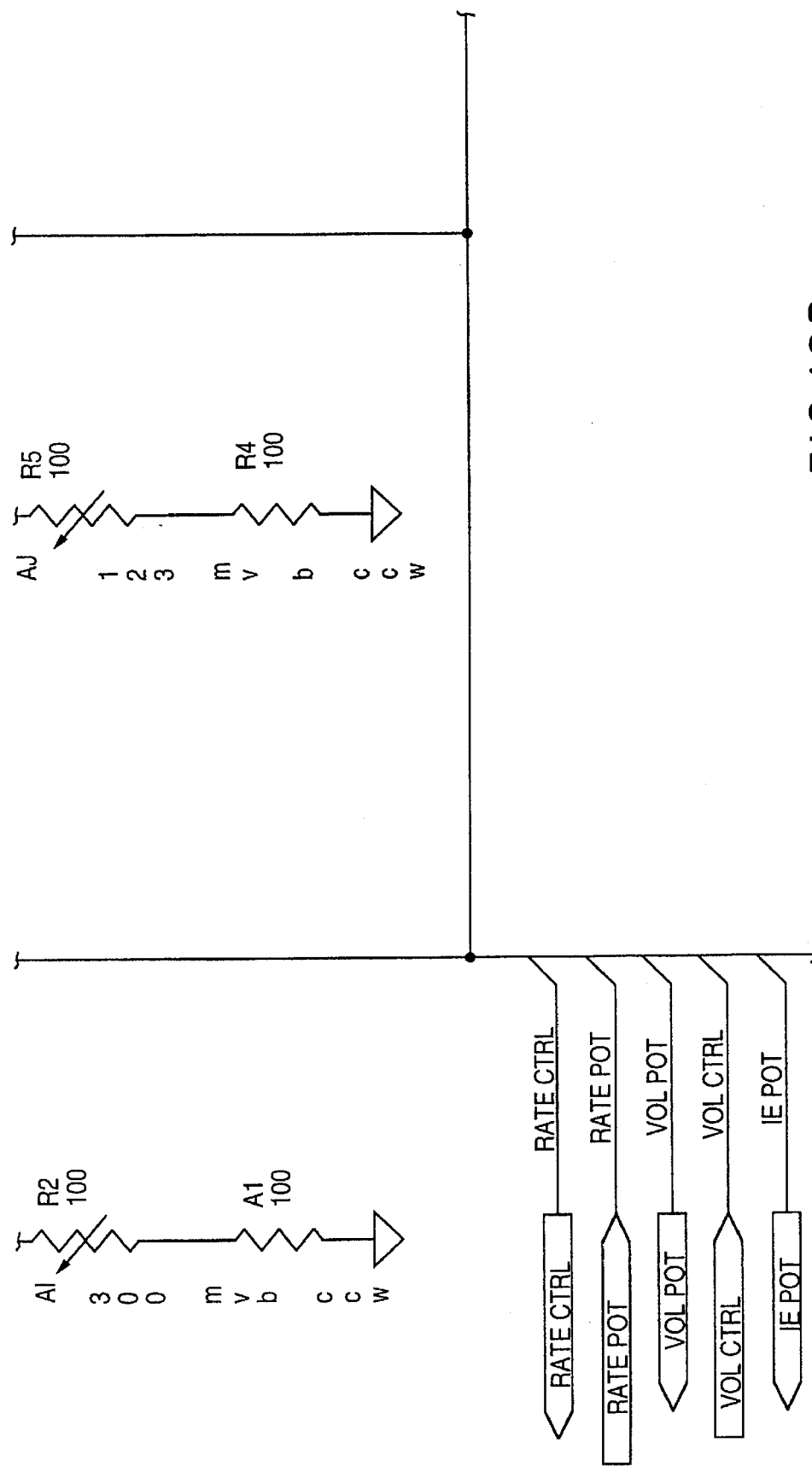
Figure 13C:
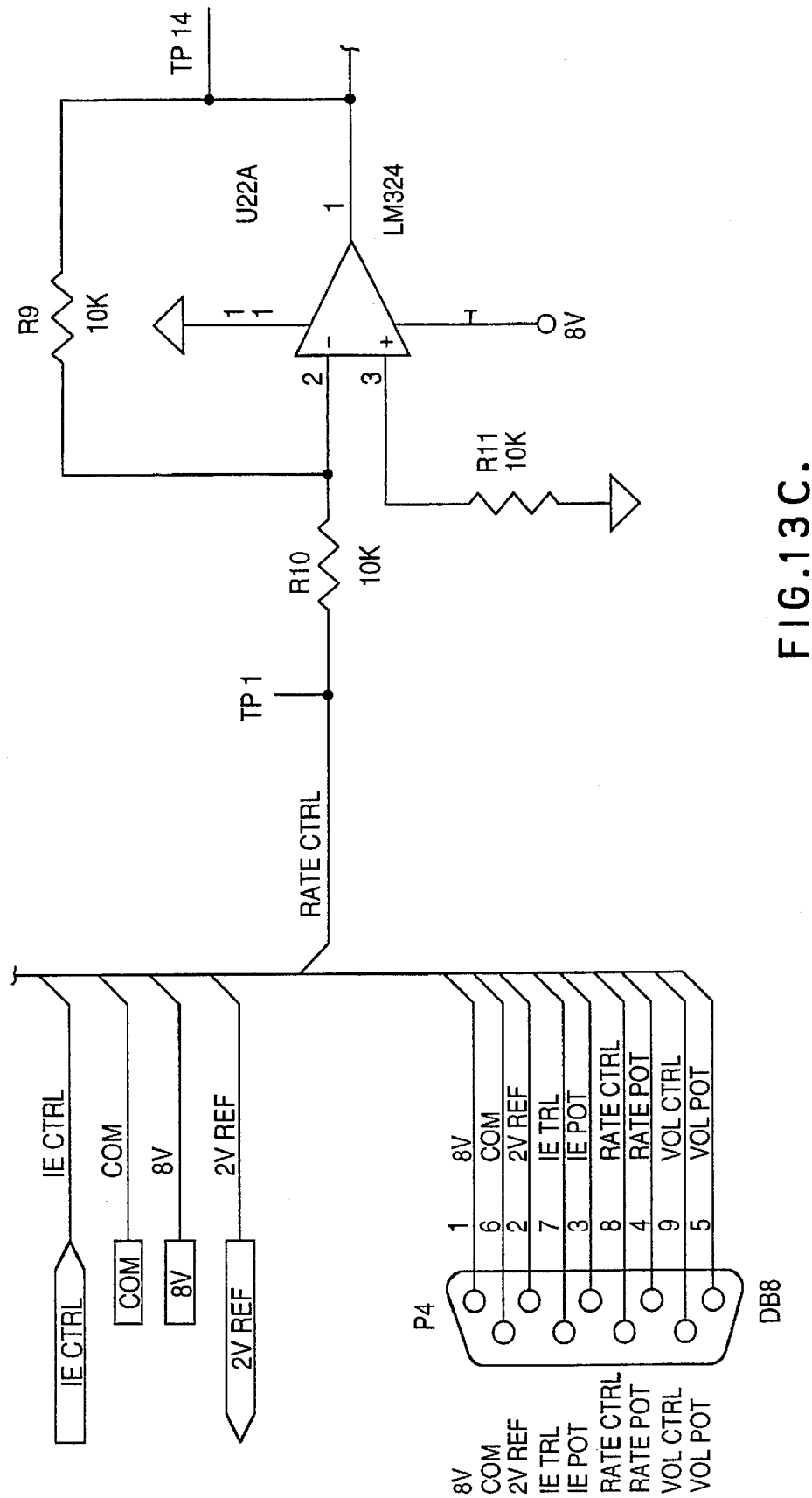
Figure 13D:
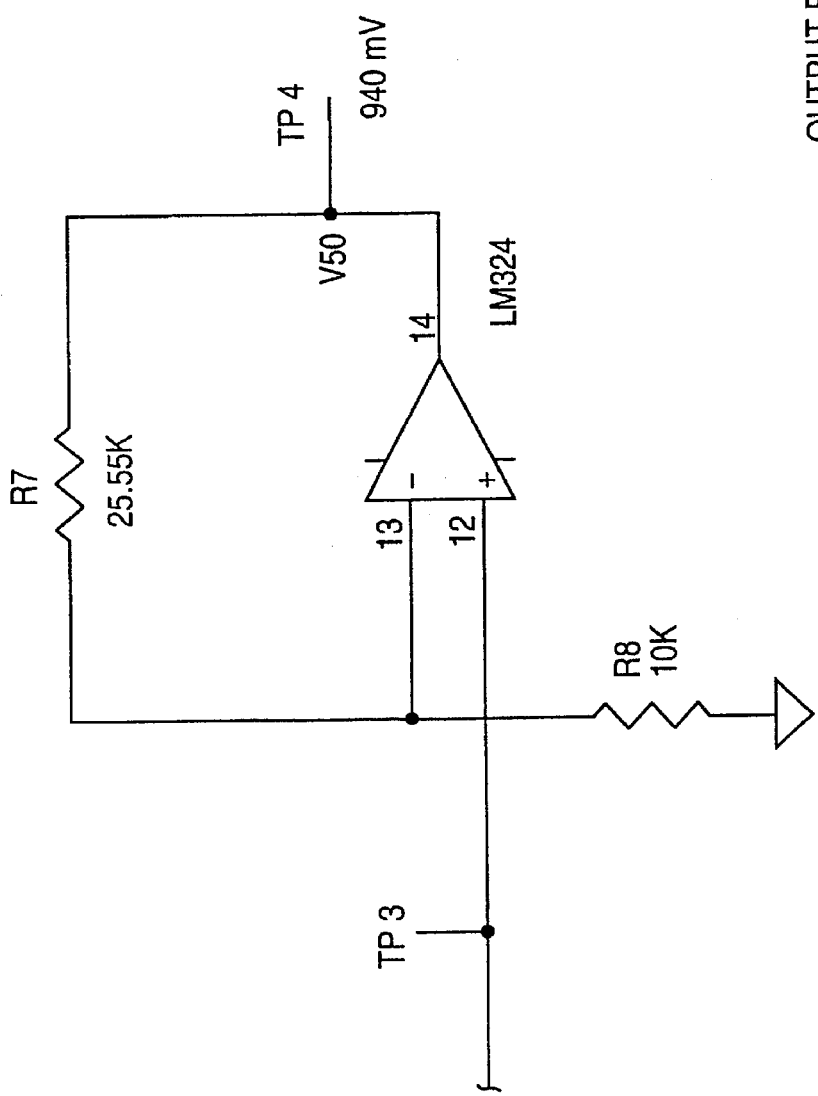
Figure 13E:
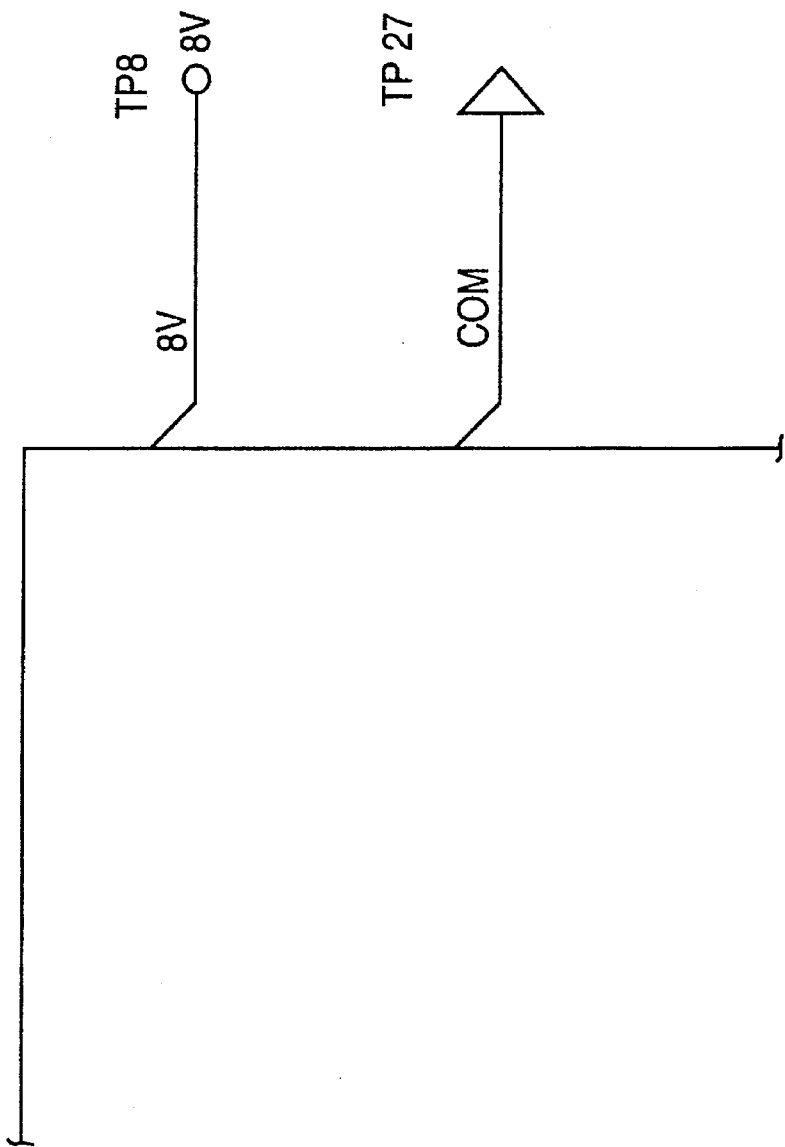
Figure 13F:
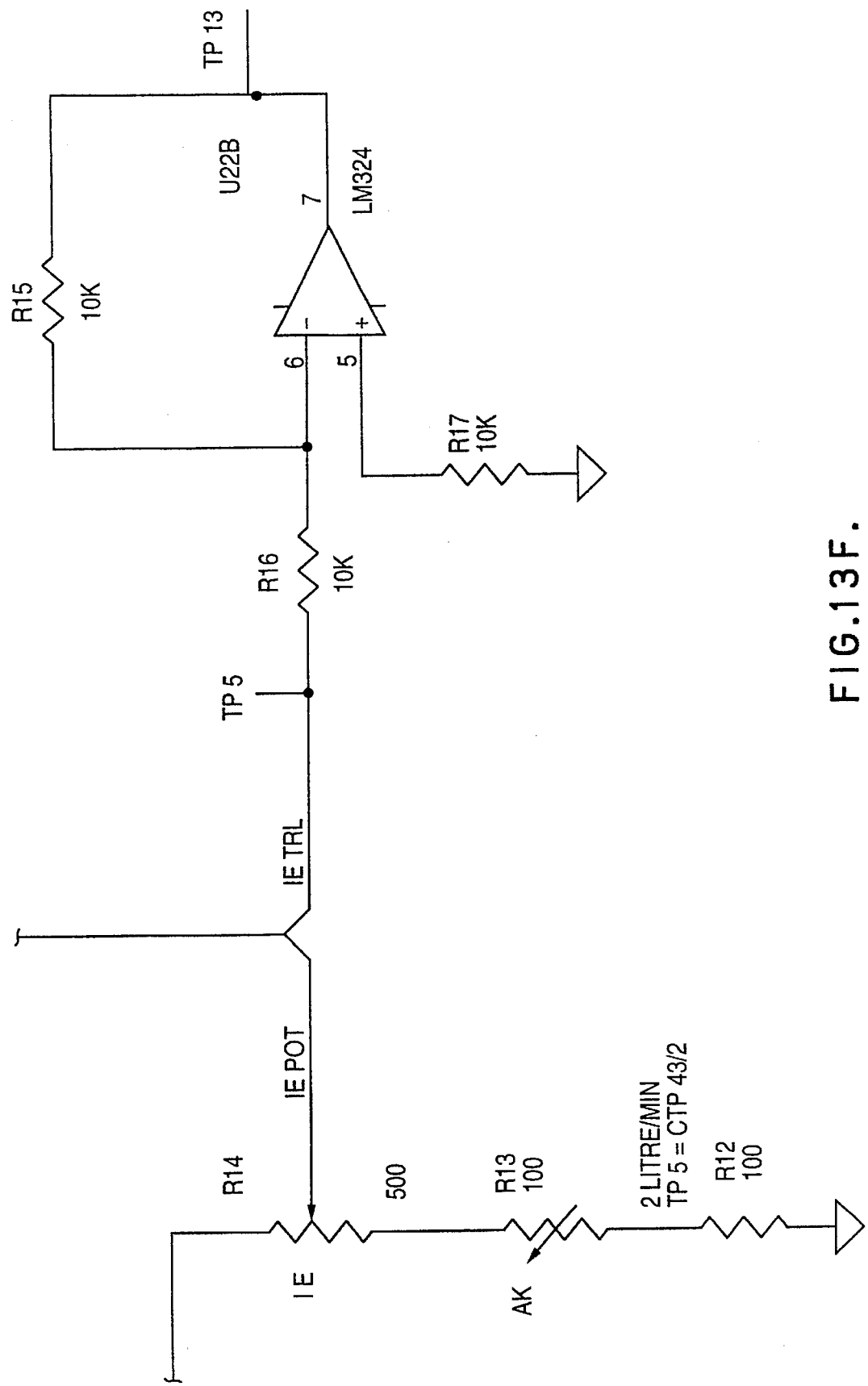
Figure 14A:
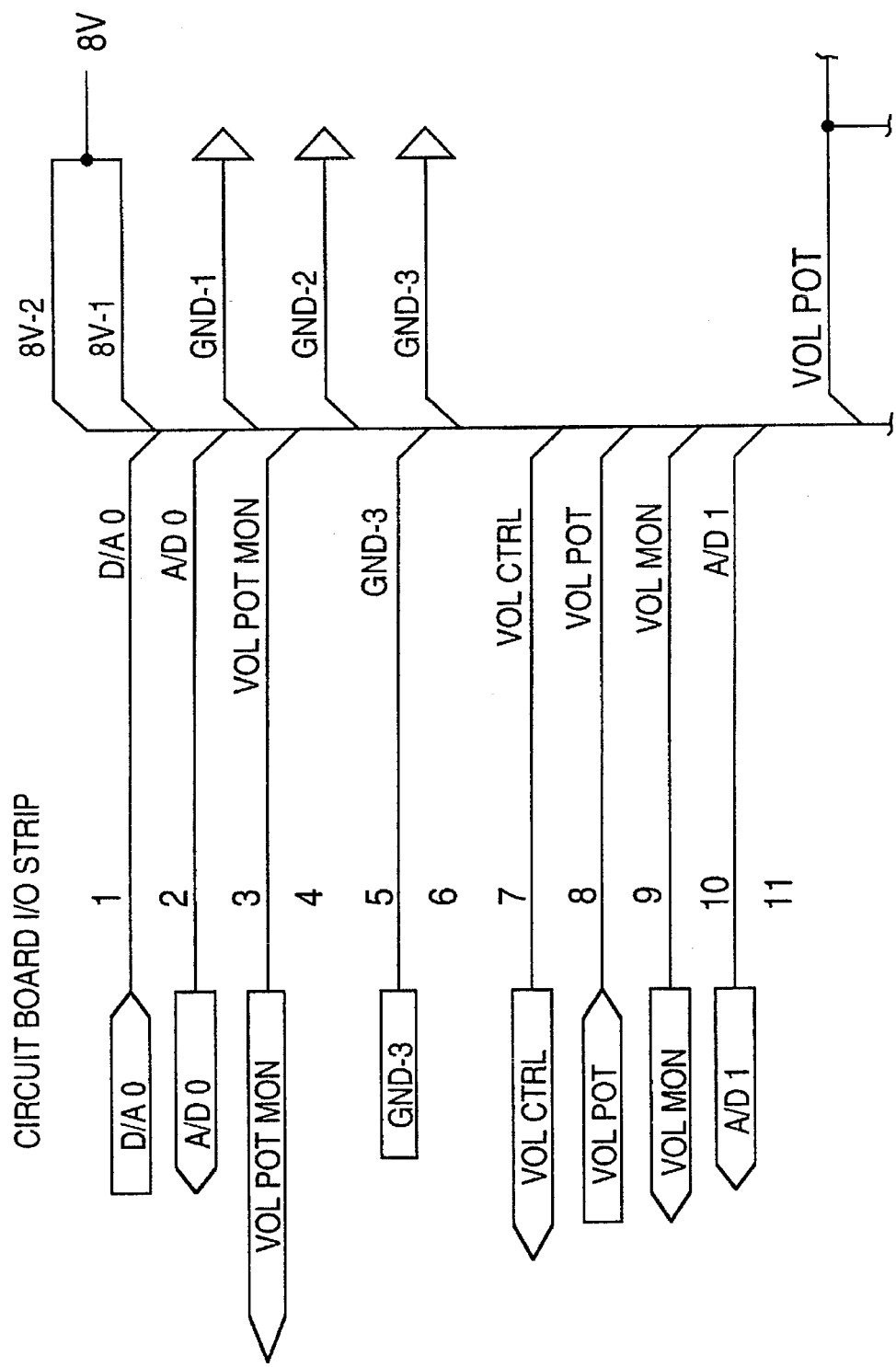
FIGS. 14 and 15 display the modulation control electronics for 'VOLUME' and 'RATE' respectively. The circuit boards are interchangeable.
Figure 14B:
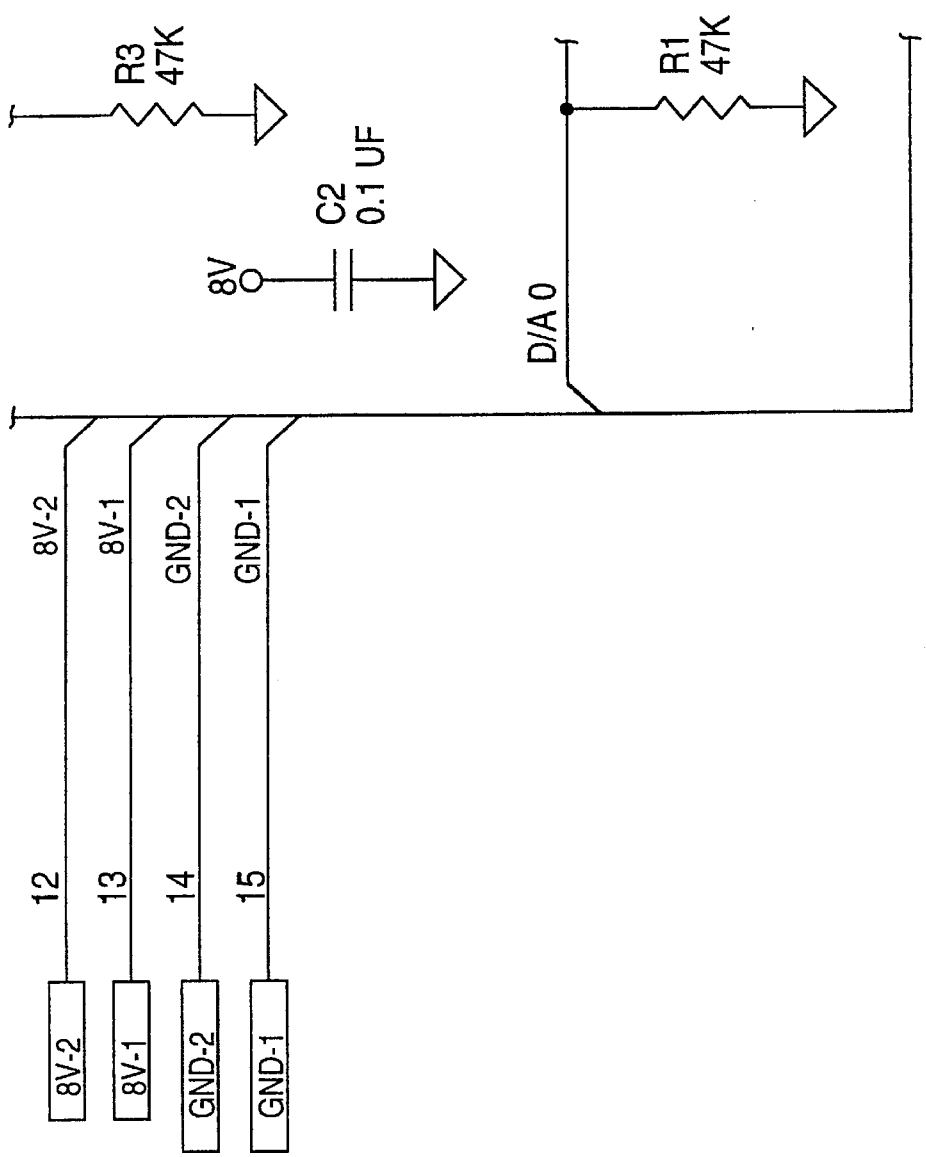
Figure 14C:
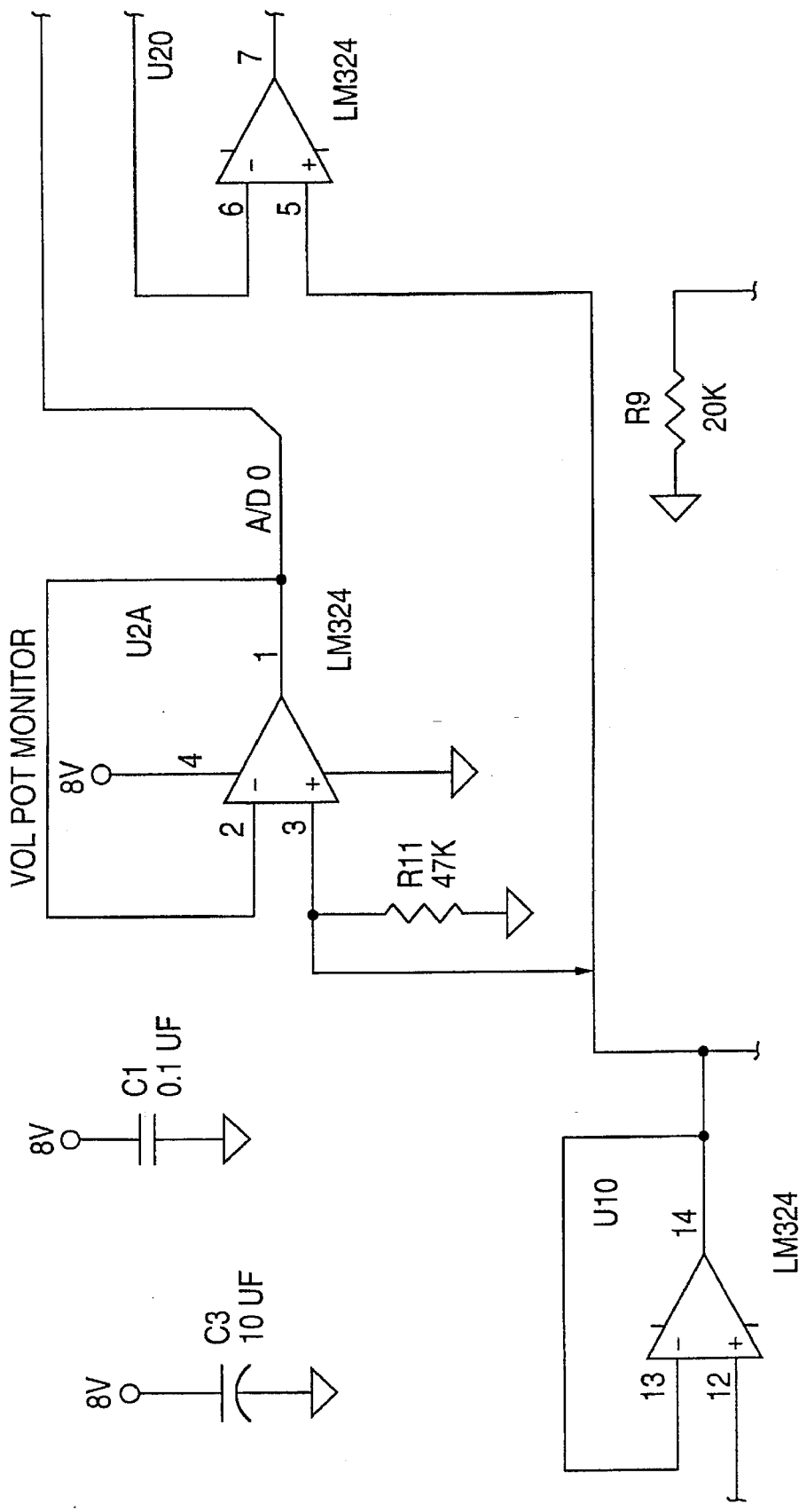
Figure 14D:
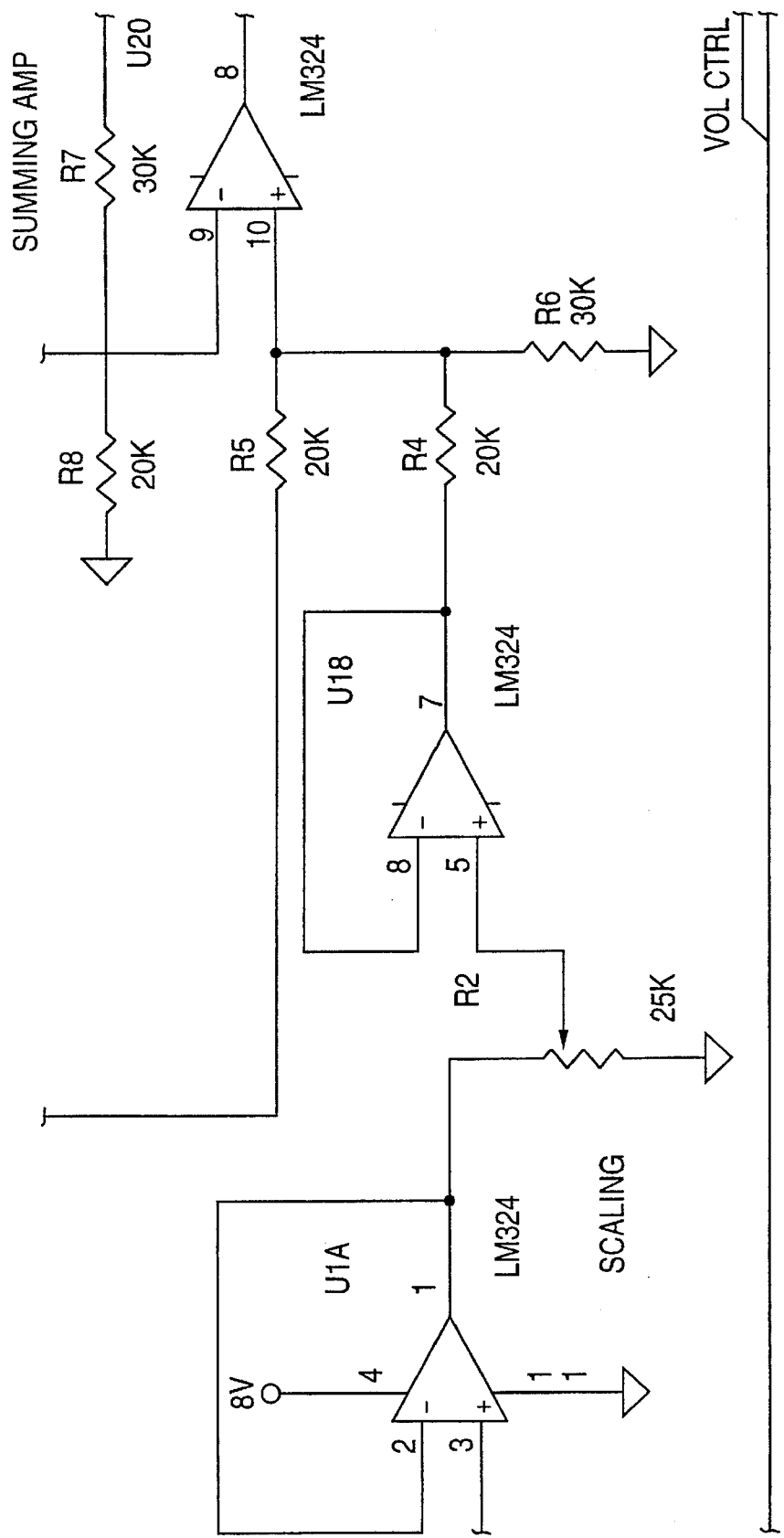
Figure 14E:
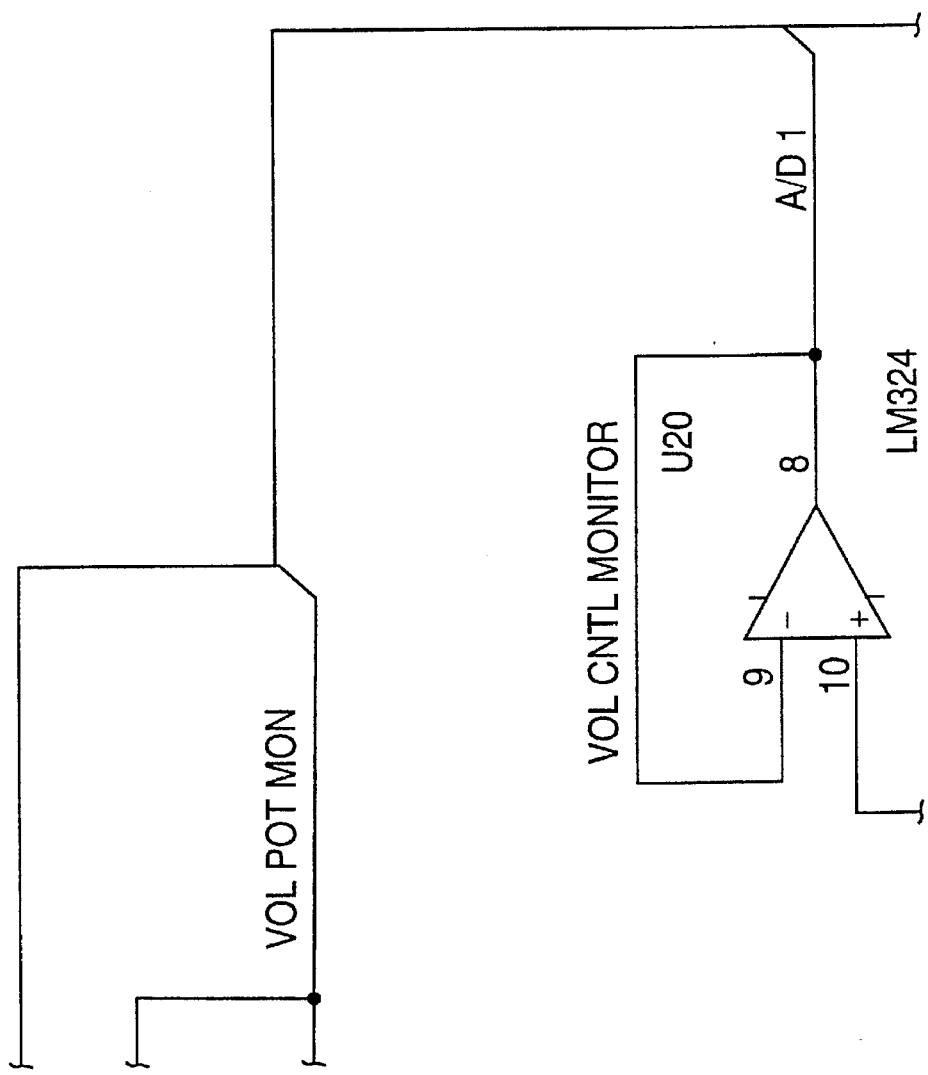
Figure 14F:
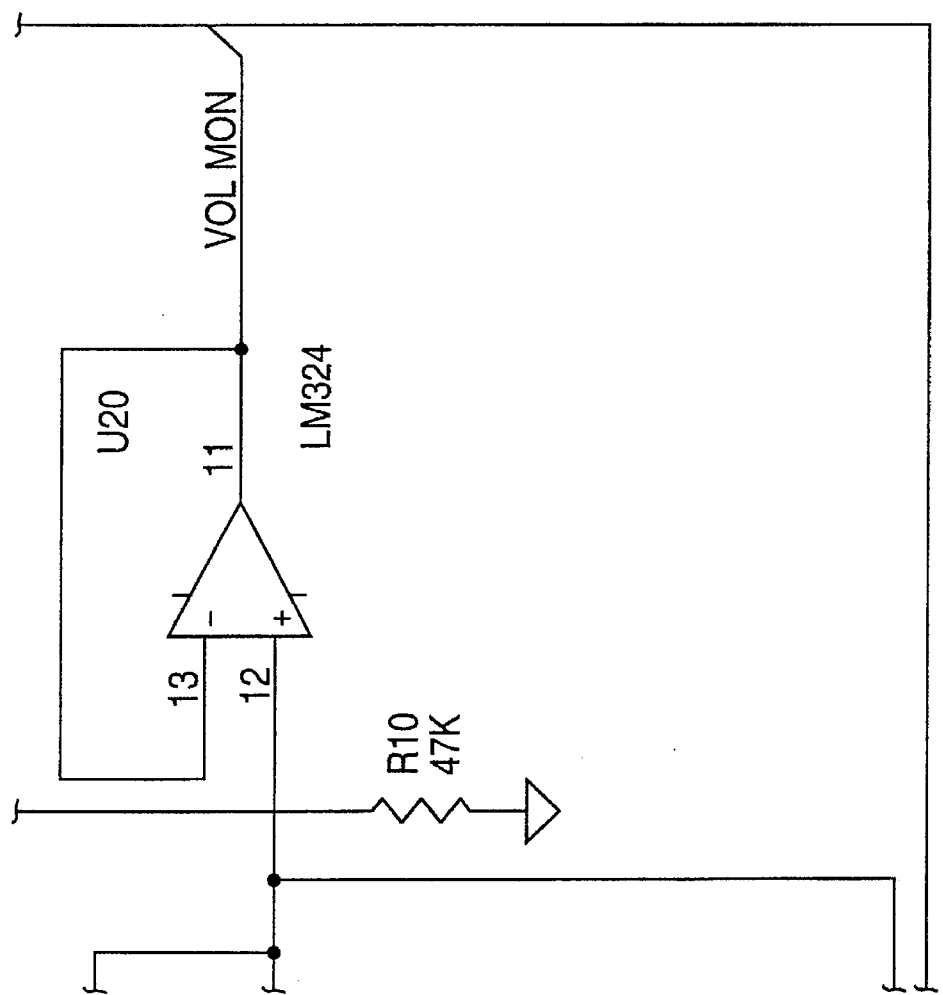
Figure 15A:
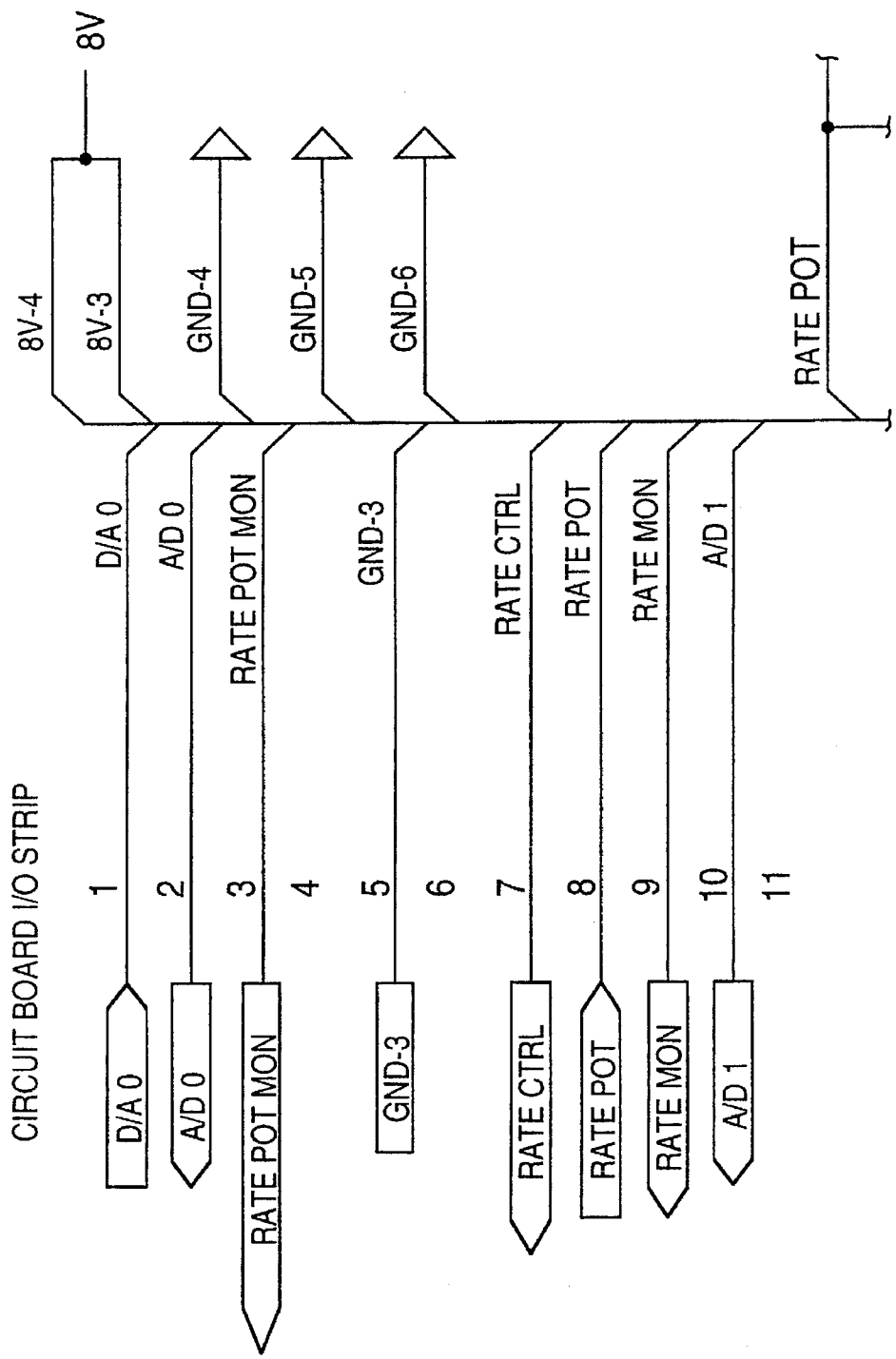
Figure 15B:
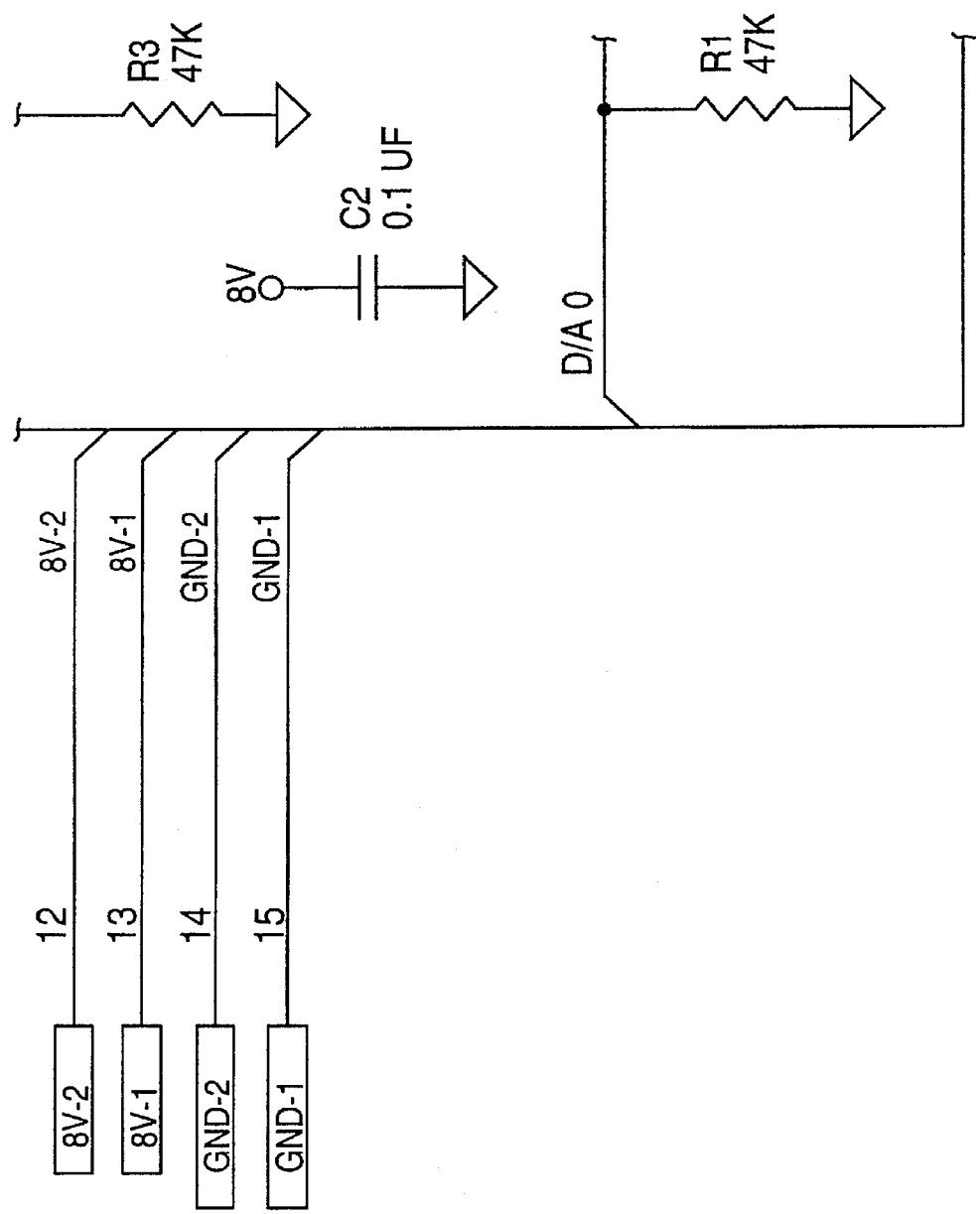
Figure 15C:
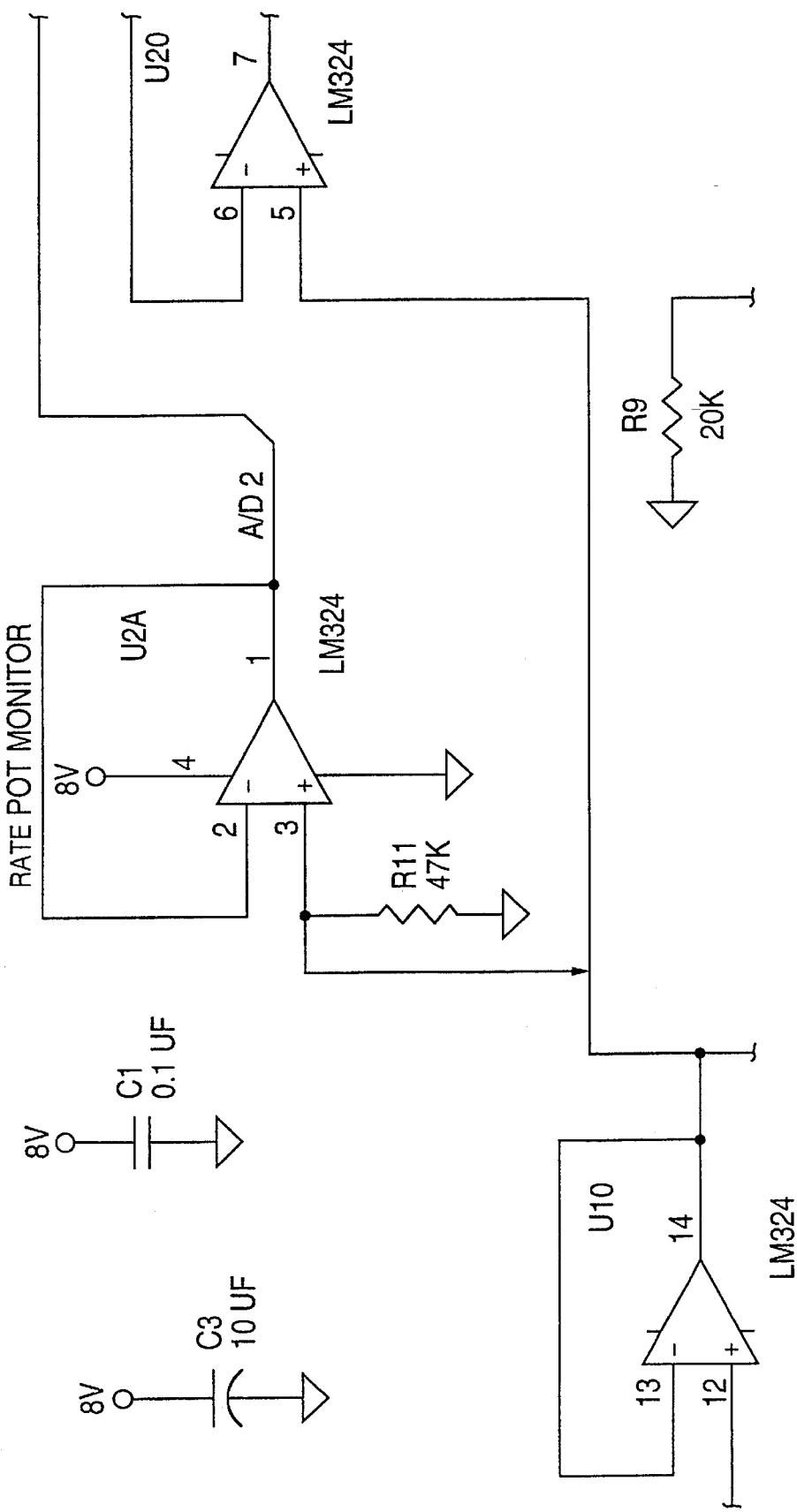
Figure 15D:
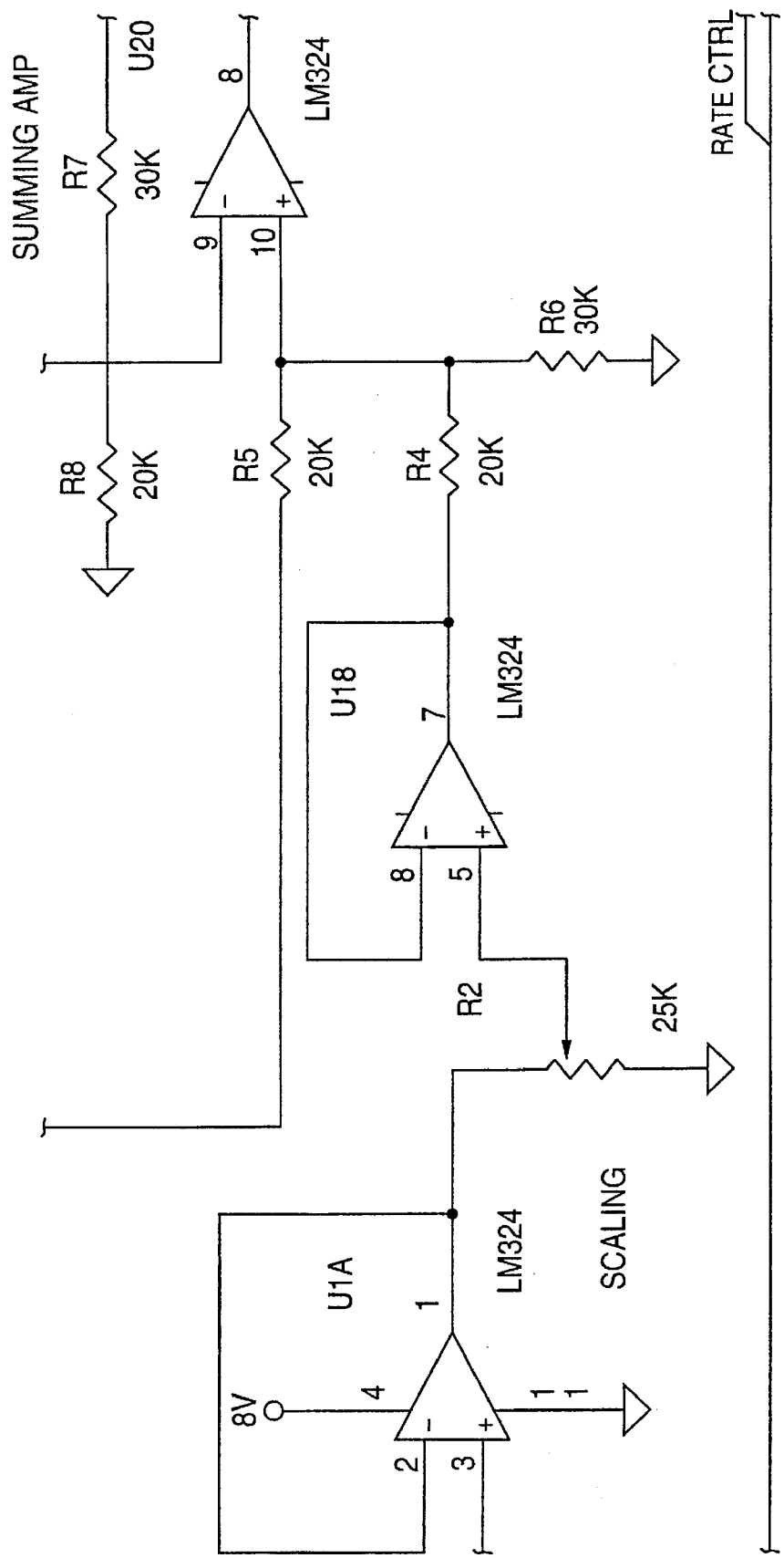
Figure 15E:
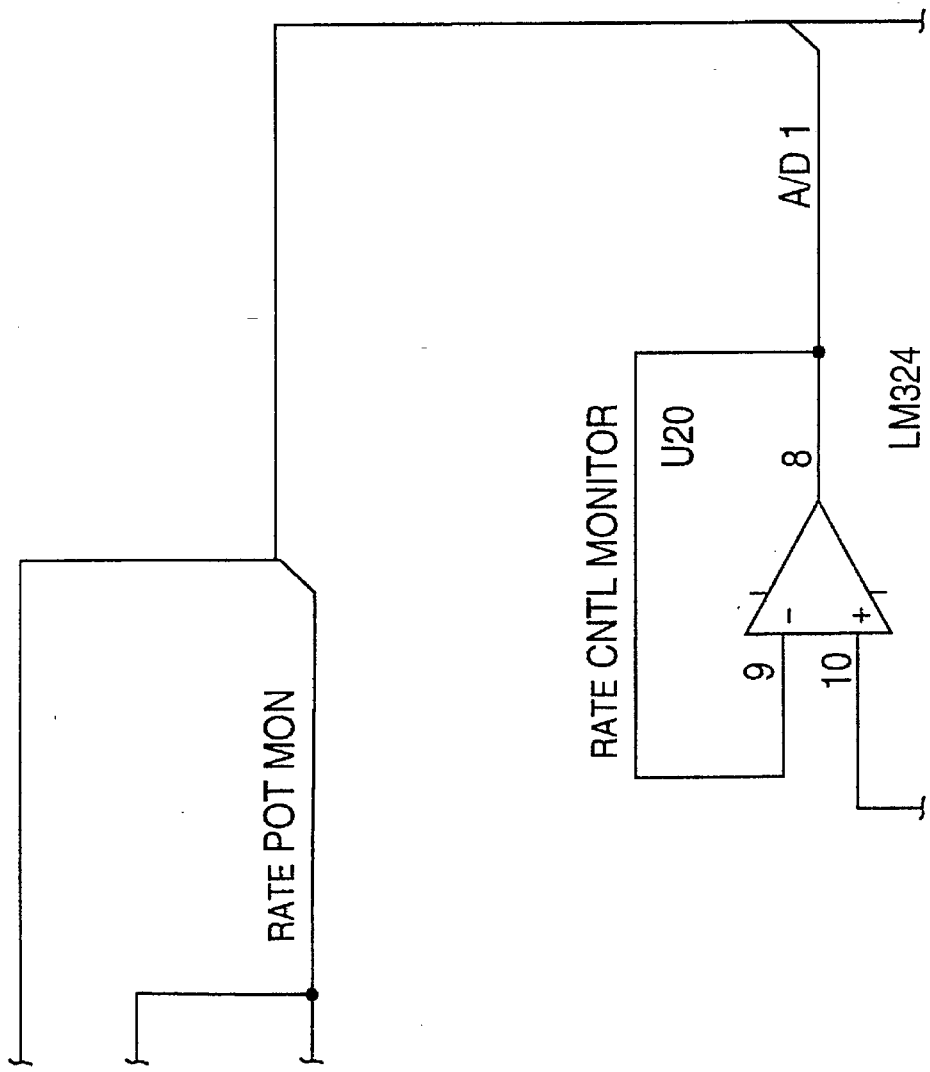
Figure 15F:
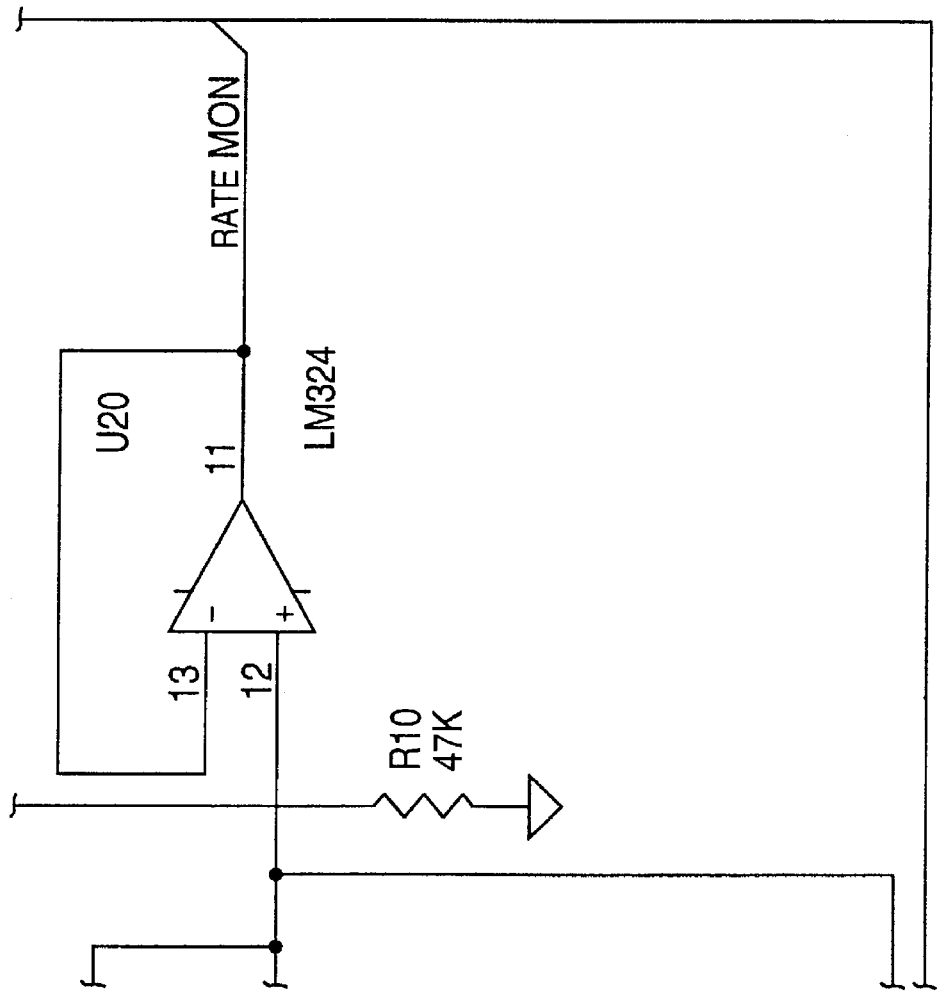
Figure 16:
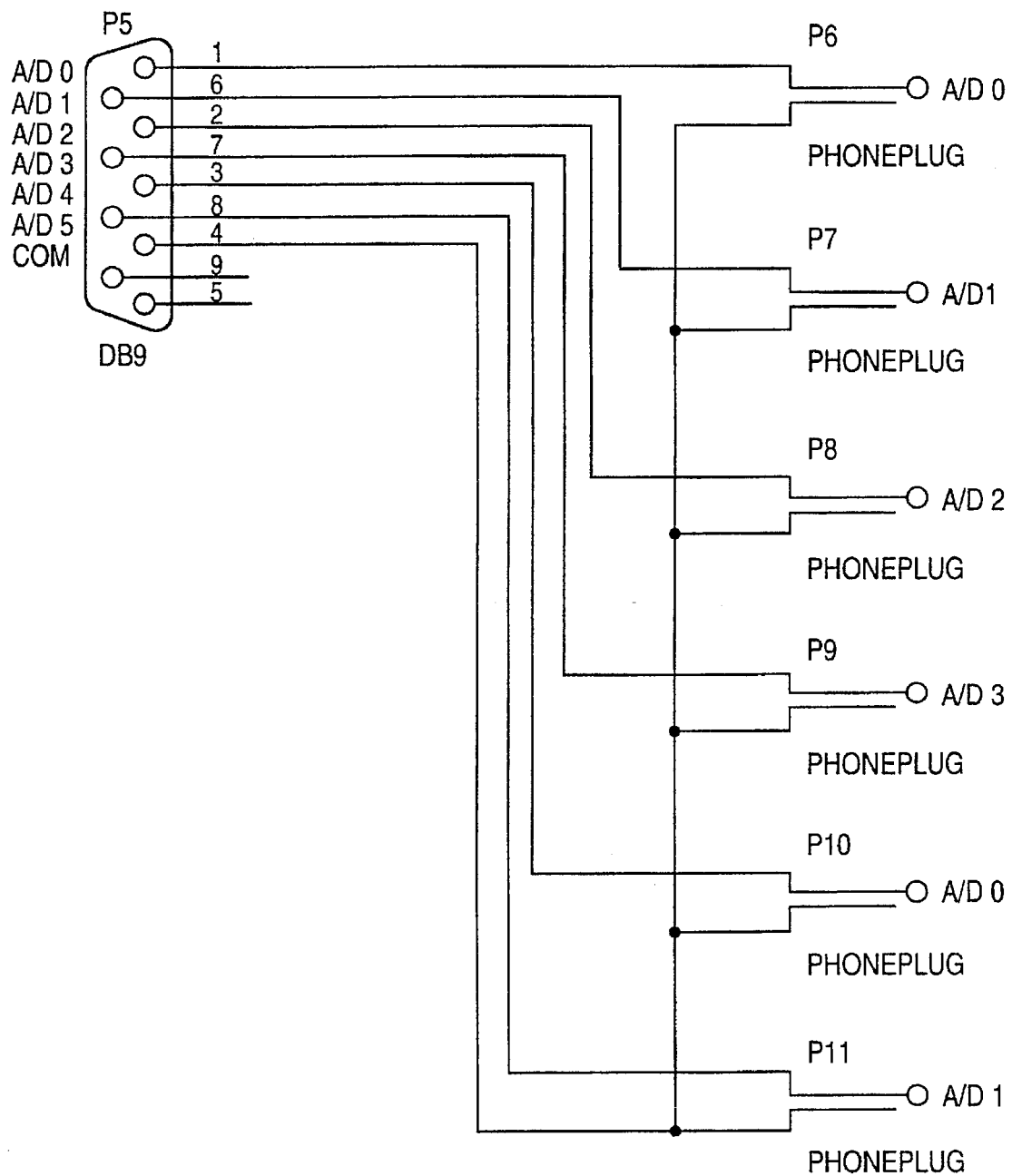
FIGS. 16 and 17 document (FIG. 6) the cable used to interface the Ohio Modulation Unit to the 'DAS16 Jumper Box' (FIG. 7), which is connected to the 37 pin connector on the Metrabyte DASH16 A/D and D/A converter.
Figure 17:
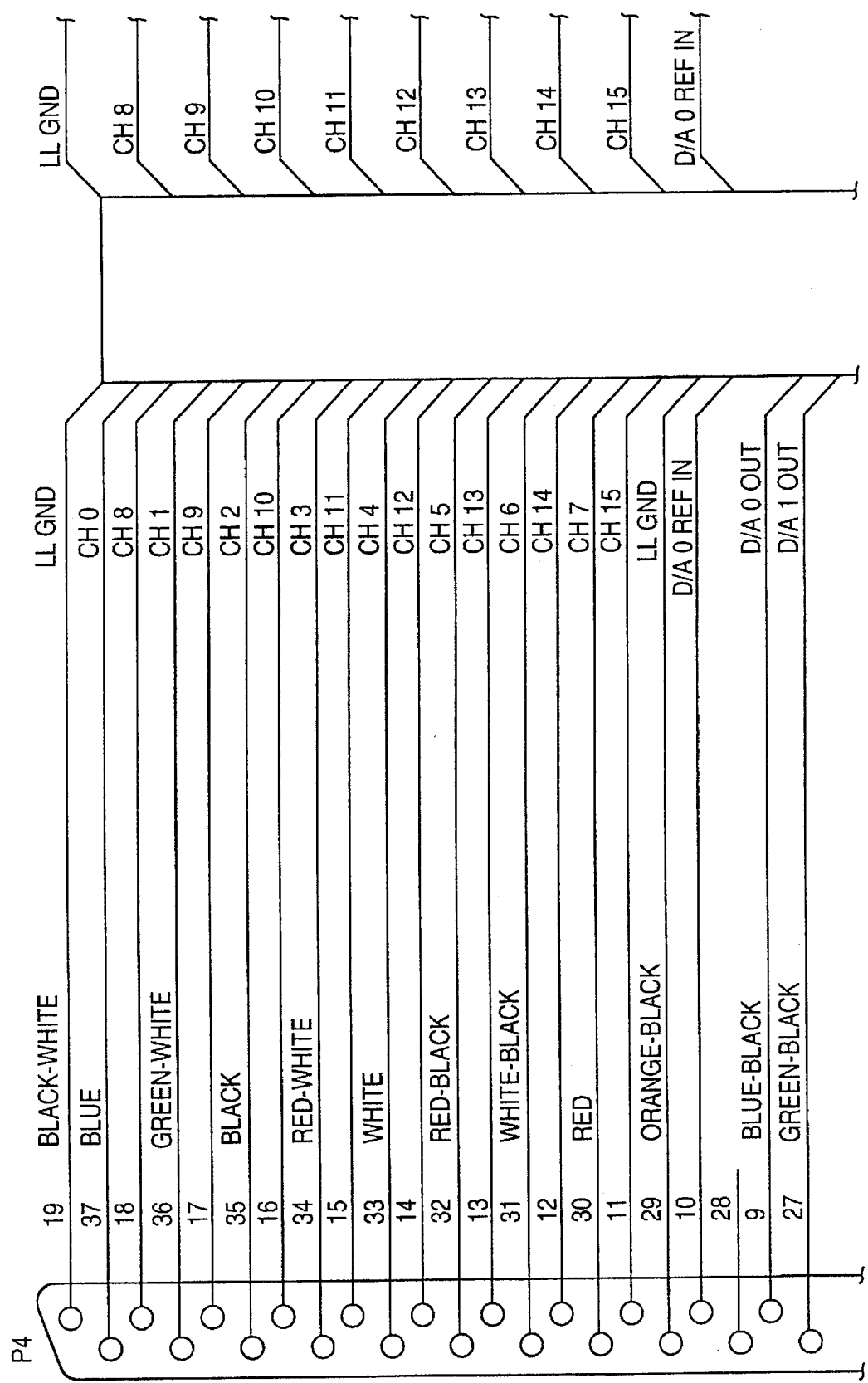
Figure 17B:
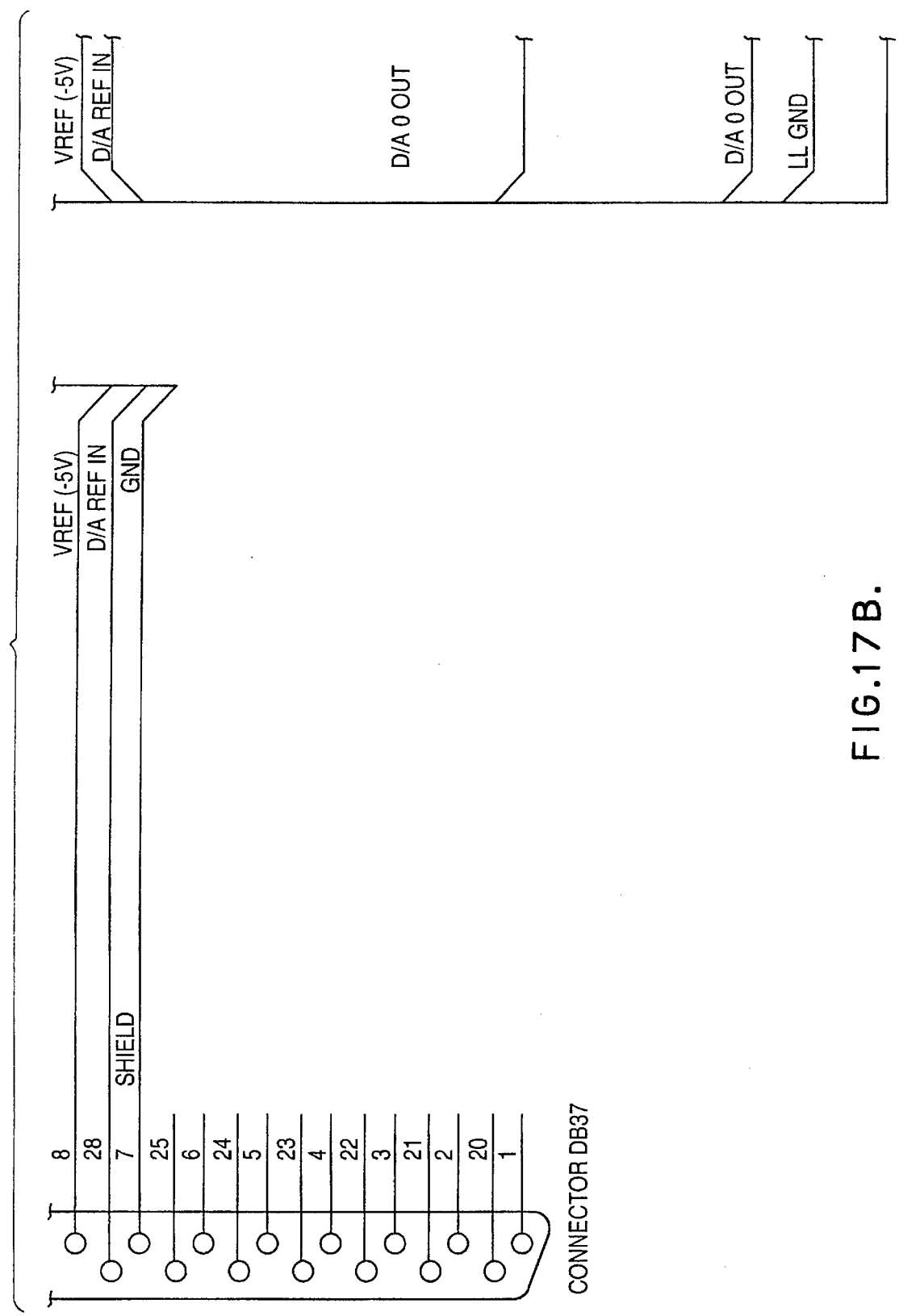

Computer-controlled Ventilation:

The ventilation used in this experiment was an Ohio 7000 having electronics as illustrated in FIGS. 11 to 17 described above. The computer-controller software (Table 8) allows the rate and volume settings of the ventilator controls to be modulated independently via a previously generated data file. Data from this modulation file is depicted graphically in FIG. 9. A frequency vs respiratory rate plot is shown in FIG. 10. The modulation file was generated from hemodynamic and respiratory excursions from an anesthetized dog. This information was captured by data acquisition, processed and scaled to produce breath-to-breath variability. Ventilatory variability can also be measured directly, stored and subsequently used to control the ventilation. Hardware was also developed to implement computer-control of the ventilator which necessitated converting voltage outputs from the breath-to-breath variability period to control ventilator respiratory rate and tidal volume, as seen in FIGS. 11 to 17. In this experimental configuration, only RR was changed. As there was employed a ventilator which functioned as a volume divider, change in the RR resulted in reciprocal changes in the TV. Functions were developed to convert ventilator rate and volume into voltage and vice versa.

Output to control RR was updated every 400 msec and changed accordingly based on the modulation data file. The computer ventilator RR was set to 10 breaths/min baseline and the modulation file programmed ventilation from 10 to 22 breaths/min with a mean value of 15 breaths/min.

Post-hot analysis:

The data file of airway pressures was processed to integrate the area under the pressure time curve to give mean airway pressure. Mean peak airway pressure was also calculated. Because of the variability in RR and TV in the computer-controlled ventilator group, a minimum of 25 breaths were analyzed in each experiment. At the end of each experiment, the animal was killed with a lethal dose of thiopental, and a sternotomy done to remove the lungs. The lungs were weighed wet and then suspended and aerated to commence drying. The following day, the lungs were placed in an oven to dry to a stable weight (±5 percent on consecutive days). The wet:dry lung weight ratio was calculated.

Statistical Analysis:

Multiple comparisons of data within and between groups was with repeated measures ANOVA. A p-value $\leq 0.05$ was considered significant for group x time interactions or differences between groups. Least squares means test matrices were generated for post-hoc comparisons. Bonferroni's correction was applied when multiple comparisons were examined within groups. Single comparisons between groups were by Student's t-test, $p \leq 0.05$ considered significant.

Example 2

This Example provides the results of the experimentation described in Example 1.

The computer-controlled ventilator varied respiration from 10 to 22 breaths/min (mean ±SD; 15.0±2.3). There were 369 RR and TV combinations over 1089 sec before the modulation file looped to repeat itself.

The demographic data from the experiments is shown in Table 3 below. There were 7 animals in the computer group and 6 in the control ventilator group. The animals in the two groups did not differ for weight or in the amount of oleic acid infused to induce the lung injury. The mean airway pressure did not differ between groups nor did the mean peak airway pressure. There was no difference between groups in the wet:dry lung weight ratio.

There was no difference between groups for blood or nasopharyngeal temperature (group x time interaction; p =0.1772 and 0.2665 respectively) (Table 4 below). A group effect was seen for baseline blood temperature of 0.6 degrees. In both groups, temperature increased significantly following lung injury. A marked difference was seen between groups for hemoglobin concentration (p =0.0014 group x time interaction). In both groups hemoglobin increased significantly following lung injury, but continued to increase in the control group. There was no interaction for pH between groups (p=0.2325) but there was a group effect with lower pH in the latter periods of the experiment in the control group.

Hemodynamic data is shown in Table 5 below. The MAP was stable between groups (group x time interaction; p=0.4429). In both groups MAP decreased significantly following lung injury. The MPAP showed an interaction (p =0.0198). In both groups the MPAP increased markedly following oleic acid. Baseline MPAP was significantly higher in the computer group then lower by 90 minutes. The PCWP was essentially identical between groups. No interaction was seen for PVR but a marked group effect was seen (p=0.0001). In both groups PVR increased dramatically with lung injury. The PVR was significantly higher from 90 min on in the control group. There was no difference between groups for cardiac output at any time period. In both, the CO decreased to about 60 percent of control and remained unchanged.

Respiratory gas data is shown in Table 6 below. End-expired $CO_2$ ($PeCO_2$) did not differ between groups. There was a significant increase in $PaCO_2$ following lung injury in both groups. This correlated to the significant increase in dead space ventilation (VD/VT) seen. Importantly, a significant group x time interaction was seen for $PaO_2$ (p=0.0448). A markedly significant group effect was seen as well (p=0.0001). This is evident from significantly greater $PaO_2$ at time periods 60–150 min after oleic acid infusion. Of note, at baseline and at Time 0, $PaO_2$ values are not significantly different. In both groups the shunt fraction (QS/QT) increased significantly following lung injury.

Example 3

This Example discusses the results obtained in the experiments described in the preceding Examples.

In these experiments described in Example 2, it has been demonstrated that oxygenation is improved by modifying mechanical ventilation to incorporate biologic variability. Through use of a computer-controller, variability in RR and TV resulted in significantly improved $PaO_2$ compared to standard IPPV with the same ventilator. This improvement in oxygenation was accomplished without an increase in mean airway or mean peak airway pressures.

No differences were seen between the two groups for amount of oleic acid administered to injure the lungs. The wet:dry lung weight ratios suggest a similar injury between the two groups. The two groups were very similar at baseline and following lung injury for PCWP, CO and PVR. Similar increases in shunt fraction and dead space ventilation were also seen for these two groups over the same time periods. Thus, the two groups appear not to differ prior to being randomized to control or computer-controlled ventilation.

Figure 8:
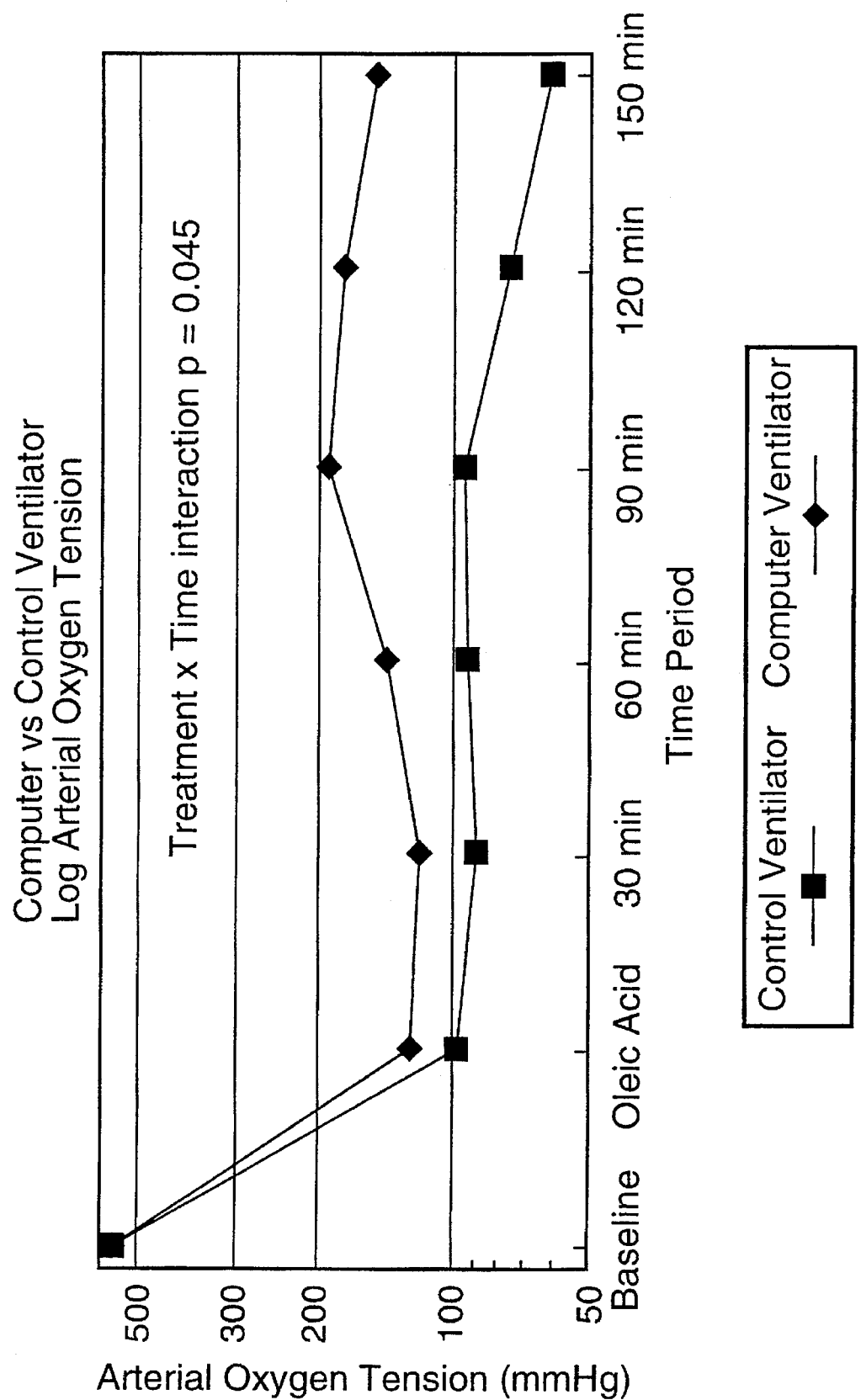
FIG. 8 shows a comparison of arterial oxygenation ($PaO_2$ in mm Hg) for computer-controlled vs. conventional mechanical ventilation in a porcine oleic acid lung injury model. Significantly greater $PaO_2$ is seen at the latter time periods in the experiment in animals ventilated with the computer-controlled ventilator (operation in accordance with the invention).

As configured for this study, the ventilator delivered 369 different RR and TV combinations with a mean RR of 15 breaths/min over 1089 sec (18.2 min). This is contrasted to a single RR of 15 breaths/min throughout the duration of the experiment in the control group. Some variability exists in the control group because MV was adjusted to attempt to maintain $PaCO_2 \leq 45$ mm Hg when VD/VT increased with lung injury. However, this entailed only a maximum of 6 changes in MV, over the course of any one experiment, when MV was changed if $PaCO_2$ was out-of-range, at the end of any 30 min measurement period. Thus, over a 30 min measurement period, RR and TV were essentially fixed in the control group but there were 369 ×30/18.2=608 different RR and TV combinations in the computer group. If, as Suki et al. (Nature, Vol. 368, April 1994, p. 615–618) suggest, airway recruitment is stochastic, then the probability of airway opening is dramatically improved using the computer-controlled ventilator. The experimental results provided herein indirectly suggest that this finding is so. Of greatest significance is that mean $PaO_2$ improved following lung injury in the computer group out to 150 min (FIG. 8) compared to an inexorable decline in $PaO_2$ in the control group. This improved $PaO_2$ was associated with significantly lower MPAP and PVR at identical PCWP in the computer group suggesting better ventilation/perfusion matching and lower pulmonary vascular resistance at similar cardiac outputs. The marked difference in hemoglobin concentration following lung injury is an independent marker that the two ventilatory modes differ. The increasing hemoglobin concentration in the control group suggests further accumulation of lung water. In the computer group, hemoglobin concentration remained essentially stable. This is especially so as the initial mean increase in hemoglobin concentration is identical in the two groups (26 percent). At Time 0, both groups were control mode ventilated. Only after Time 0, was computer ventilation initiated. Therefore, by inference, during the conduct of the experiment, lung water accumulation was less in the computer group with associated better oxygenation.

Example 4

This Example illustrates the materials and methods used to evaluate a CPB pump in dogs, using the computer control operation described above with reference to FIGS. 1 to 4.

Experimental Preparation:

Twelve mongrel dogs (21±3 kg) were studied. All animals were anesthetized with sodium thiopental (25 mg.kg$^{-1}$). The trachea was intubated and the animal ventilated with $O_2$. The minute ventilation was adjusted to maintain $PaCO_2$ at 35 to 40 mm Hg. The dog was positioned in a stereotactic head-frame in a modified sphinx position. Bipolar EEG electrodes were placed over the parietal hemisphere bilaterally and monitored by an Interspec Neurotrac® in raw EEG mode. Temperature was measured in the nasopharynx using a calibrated YSI tele-thermometer®. Anesthesia was maintained with isoflurane 1.3% end-tidal (1 MAC) during the surgical preparation. Following thoracotomy, the isoflurane was discontinued for a minimum of 30 min and the EEG made isoelectric with a bolus of thiopental. A continuous infusion of thiopental was initiated at 10 mg.kg$^{-1}$.hr$^{-1}$ to maintain the EEG isoelectric during CPB. Neuromuscular relaxation was achieved with pancuronium bromide.

A flow-directed catheter was advanced through the left femoral vein into the right atrium for central venous pressure (CVP) monitoring. A femoral artery catheter was advanced into the distal aorta for arterial pressure (MAP) monitoring. A double lumen (7.5 FR) catheter was inserted into the left brachial artery for intermittent blood withdrawal. The superior sagittal sinus (SSS) was exposed by trephine and the posterior one-third was cannulated non-occlusively by insertion of a 22-gauge intravenous catheter. Continuous cerebrospinal fluid pressure (CSFP) measurements were recorded by inserting a 22-gauge spinal needle into the cisterna magna with the use of a micromanipulator (Narishige®). A right thoracotomy was performed. The right atrium and proximal aorta were cannulated with a single stage 38 Fr atrial and Jostra®21 Fr or 24 Fr aortic cannula, respectively. Following the initiation of CPB, the left ventricle was vented by a cannula inserted through the right superior pulmonary vein and the proximal aorta was occluded with a Seldinger vascular clamp.

All blood pressures and the CSFP were measured by calibrated Abbott® transducers referenced to the intra-auricular line. Data were recorded continuously on paper by an oscillograph (recorder model 7754A®, Hewlett Packard) and intermittently on hard disk by an IBM PC-AT® computer based data acquisition system (Dataq Instruments®). The latter data are reported. Arterial and SSS blood gases were measured before and after each microsphere injection by an ABL-3 Acid-Base Laboratory (Radiometer®) at 37° C. and not corrected for temperature. Arterial and cerebral venous (SSS) oxygen content and hemoglobin were measured by Radiometer OSM-3 (specific for canine blood).

Cardiopulmonary bypass was conducted utilizing a Travenol® non-pulsatile roller pump with a Terumo Capiox E membrane oxygenator and a Bentley® arterial line filter (25 μm). The roller pump and oxygenator were primed with 2.5 to 3.01 of lactated Ringer's and 1 to 2 units (500 to 1000 ml) of canine whole blood in CPDA-1 solution. The blood was obtained 48 to 72 hours prior to the experiment from a donor animal and refrigerated at 4° C. The animal was systemically heparinized with 300–400 IU.kg$^{-1}$ of heparin (Organon: porcine intestine®) and additional doses as required, to give an activated clotting time (ACT)≧400 sec (Hemochron 400®). Throughout the experiment the animal had an intravenous infusion of lactated Ringer's at 200–250 ml.hr$^{-1}$ containing 25 mEq.l$^{-1}$ of $NaHCO_3$. This was done to maintain a stable hemoglobin concentration and acid-base state during the experiment (α-stat acid-base management). Norepinephrine (40 μg) was injected into the oxygenator coincident with initiating CPB to minimize the hemodynamic consequences. The animals were randomized to one of two groups: non-pulsatile bypass group; Group NP (n=6), or computer-controlled bypass group; Group CP.

Group CP (n=6). Following the initiation of CPB, cooling to 28° C. commenced immediately in both groups. Temperature was altered using a Travenol heat exchanger. In both groups of animals, the mean cerebral perfusion pressure (CPP; MAP—mean CSFP) was maintained at greater than 60 mm Hg. Hypothermic non-pulsatile CPB continued for 105 min in Group NP and for 15 min in Group CP while the computer-control was being established (see below) and then for 90 minutes with computer pulsation. At 105 min, rewarming was commenced. In both groups, rewarming to baseline temperature was over 30 min. At 45 min after the start of rewarming, cerebral blood flow (CBF) and blood gas samples were obtained.

In these experiments, for each animal in Group CP, by means of a data acquisition system, a 15 min data file of blood pressure was obtained following induction of anesthesia. Data from a typical modulation file is depicted graphically in FIG. 2. A typical output from the computer-controller roller pump relating computer voltage output and the changes in MAP are shown in FIG. 3. The data is processed by a computer programmed using Table 1.

Cerebral Blood Flow Measurements:

The radioactive microspheres, ultrasonicated in saline, were injected into the arterial cannula, approximately 1 meter proximal to the aortic root, after the $PaCO_2$ was stable between 35–40 mm Hg. If the $PaCO_2$ could not be stabilized in this range by adjusting the $O_2$ flow to the oxygenator, $CO_2$ was added with a Sechrist® mixer. Approximately $2.5 \times 10^6$ microspheres (15 μm diameter) were injected into the arterial cannula. This number of microspheres assured greater than 400 microspheres/sample for accurate blood flow measurement (Heymann et al., 1977). The randomly selected microspheres were labelled with $^{46}$Sc, $^{85}$Sr, $^{141}$Ce, $^{95}$Nb, or $^{113}$Sn (New England Nuclear). A Harvard pump® withdrew a reference blood sample for determination of organ blood flow (25 ml) from the brachial artery (Compugamma®) after being weighed. The counts/min were converted to regional CBF in ml.g$^{-1}$.min$^{-1}$ with the use of standard equations.

Total CBF (tCBF) was determined by summing weighted flows to all brain regions and dividing by total brain weight. Similarly, cerebral hemispheric CBF (hCBF) and brain stem CBF (bsCBF) were determined by the summation of weighted flows to the cerebral hemispheres and brain stem, respectively. The CPP was measured as (MAP—mean CSFP) and cerebral metabolic rate for $O_2$ ($CMRO_2$) as hCBF ×(Art—SSS $O_2$ content) in ml $O_2$.g$^{-1}$.min$^{-1}$.

Statistical Analyses:

Changes over time for blood gas and hemodynamic variables were evaluated by analysis of variance (ANOVA)

Example 5

This Example describes the results obtained using the materials and methods described in Example 4.

Temperatures and hemodynamic data are shown in Table 7 below. The temperature did not differ between groups for either the period of hypothermia or following rewarming. In all instances, the nasopharyngeal temperature was able to be increased to 35° C. within the 30 min time frame without exceeding a temperature gradient of 8° C. between the heat exchanger and the nasopharyngeal measurement sites. The MAP remained stable over the two temperatures in both groups. A difference in MAP was seen between groups with MAP being greater at both temperatures in Group CP but there was no group x time interaction (p=0.0904). In both groups the CSFP increased with rewarming. The CPP was stable over time, within groups, with no group x time interaction (p=0.771).

The blood gas and blood $O_2$ content data are shown in Table 8 below. Both groups had similar hemoglobin concentrations during CPB and similar pH and $PaCO_2$. A significant group by time interaction was observed for SSS $O_2$ content (p=0.0005), SSS $O_2$ (p=0.003), and art-SSS $O_2$ content difference (p=0.011). In all instances Group CP remained more stable. In Group NP, there was a significant decrease in SSS $O_2$ content and SSS $O_2$ with rewarming, and an increase in the art-SSS $O_2$ content difference.

The regional CBF and $CMRO_2$ data are shown in Table 8. In both groups regional CBF increased with rewarming. There was no difference between groups for CBF in any region. Flow:metabolic coupling decreased with rewarming in Group NP. There was no difference in $CMRO_2$ between groups. In both groups $CMRO_2$ increased with rewarming.

Example 6

This Example discusses the results obtained in Example 5.

Figure 7:
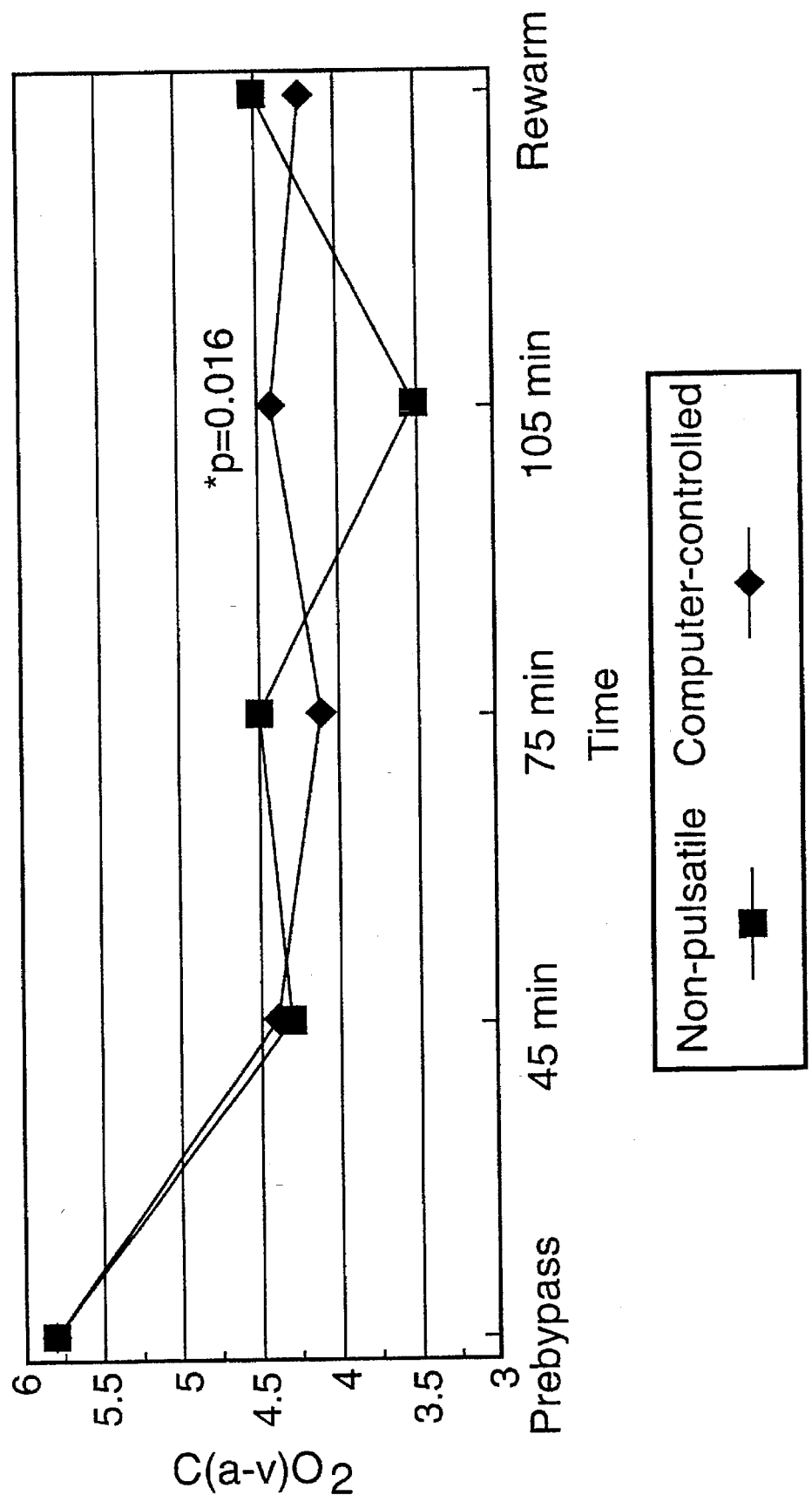
FIG. 7 shows the arterial minus superior sagittal sinus (cerebral venous) oxygen content difference during CPB with computer-controlled and conventional roller pump bypass in dogs (n=6 both groups). The oxygen content difference is stable during conduct of CPB in the computer-controlled group (operation in accordance with the invention). In the control group (conventional roller pump), increased oxygen extraction occurs during the period of rewarming compared to the hypothermic period of CPB immediately before. Such changes in oxygen content difference with rewarming are associated with cognitive impairment following CPB in man.

Use of computer-controlled CPB roller pump according to the invention, which restores inherent biologic variability, as described in Examples 4 and 5, prevents cerebral deoxygenation during rewarming. The SSS $O_2$, SSS $O_2$ content, and the art-SSS $O_2$ content difference were all stable following rewarming in Group CP. In contrast, in Group NP, the SSS $O_2$ and SSS $O_2$ content decreased and the art-SSS $O_2$ content difference increased with rewarming suggesting cerebral deoxygenation with conventional non-pulsatile CPB (Table 8, FIG. 7). This experimental group had CPB managed similarly to that of patients in a study by Croughwell et al. (Ann. Thorac. Surg. 1994; 58:1702–1708) (α-stat acid-base management, use of arterial line filter and membrane oxygenator, and a similar duration of CPB). In all instances, the cerebral deoxygenation was not as severe as that seen by Croughwell et al. However, the changes seen were similar to those in the clinical scenario, and the more important observation is that computer-controlled CPB prevented these changes with rewarming.

The differences between the two groups does not appear to be a consequence of changes in CBF with computer-controlled CPB. It is of interest that the $O_2$ content difference was lower during hypothermia in Group NP than in Group CP and became greater with rewarming. This may suggest that there was a difference in distribution of CBF during CPB between the two groups given no difference in tCBF. If so, this finding could imply two flow pathways with CPB (a shunt and a parenchymal flow pathway). The use of computer-controlled CPB which restored inherent biologic rhythms would appear to provide better parenchymal flow, resulting in a greater oxygen content difference during the hypothermic bypass period and an ability for recruitment of the capillary bed in proportion to the requirements of increased metabolic demand with rewarming. With non-pulsatile bypass, the lower $O_2$ content difference at similar tCBF suggests a greater shunt flow, during the period of hypothermia. With rewarming, parenchymal blood flow appears inadequate to meet the increased metabolic demands of the tissue which results in increased extraction of oxygen and an increased $O_2$ content difference, lowered SSS $O_2$ and $O_2$ saturation. These results suggest that the greater deoxygenation seen with conventional CPB may be a consequence of capillary closure to parenchymal beds due to non-pulsatile bypass.

Non-pulsatile perfusion has been demonstrated to increase tissue water and alter vascular properties in other tissues such as the lung. These effects of the abnormal pulsation are unaltered by hypothermia, anesthesia or use of arterial filters. Hence these presumed neural protective interventions may not be helpful and may account for lack of clinical correlates of improved neurologic outcome with their institution. The improvements seen with computer-controlled pulsatile flow provides strong indirect evidence that the microembolic theory inadequately explains why the brain is damaged during CPB.

The better cerebral oxygenation occurring with computer-controlled CPB is not likely due to any change in the microembolic load presented to the brain. Pulsation, per se, should not alter the microembolic load, and the CBF was identical in the two groups, at both temperatures suggesting another mechanism independent of microemboli being the causative reason for the difference between groups. Microemboli are felt to be the leading candidates to explain the neurologic and neuropsychologic damage following CPB. The microemboli theory cannot effectively explain the reason for the increased $O_2$ extraction seen on rewarming. An explanation of parallel flow pathways during CPB (one shunt pathway and one parenchymal flow pathway) which is a consequence of the monotonous regular non-pulsatile blood flow with resultant cerebral capillary bed closure can explain why neural damage occurs despite strategies to decrease cerebral blood flow and thereby decrease the embolic load to the brain. Computer-controlled pulsation creates a more physiologic flow state with improved cerebral oxygenation following rewarming.

SUMMARY OF DISCLOSURE

In summary of this disclosure, the present invention provides computer control of the operation of a cardiopulmonary bypass pump, a lung ventilator or other device which provides simulation of in vivo variability of flow of a biologic fluid to an organ. Modifications are possible within the scope of this invention.

28
Table 1
Program Listing for Blood Pump Control
```
{$A+,B-,D+,E+,F-,I+,L+,N+,O-,R+,S+,V+}
{$M 16384,0,655360}
{Program to control the RPM of a perfusion pump by a variation
derived from a file generated by Codas of a pressure recording -
before heart bypass has occurred.
Input file is format commented in LoadPeakRates.  The Peak
pressure and the heart rate period are the only columns used.
The minimum of the Peak pressure is removed from each observation
to generate a list of Peak Pressure variations from minimum to
maximum.
The Peak Pressure variations from 0 to max are scaled from 0 to
5 volts and sent out the D/A channel 0 output.  External scaling
is used to establish the RPM variation associated with 5 volts
output.
The period each pressure variation is held at the output is
related to the heart rate period.
The data is scanned forwards and then backwards continuously
until a key is struck.
}
Program Purfus;
Uses Crt, Dos;

Const
 MAXBUF = 8000; {maximum # of 3 sets of data points to be loaded}
Type
 datbuf = array[1..MAXBUF] of single;
 datdef = ^datbuf;
 statdef = array[1..3] of single;
Var
 peak, mean, period : datdef;
 peakstat, meanstat, periodstat : statdef; {stats of data loaded}
BaseAddr : word;

{Driver for Das16 D/A channel 0 = BaseAddr + 4, + 5}
```

```
                                  29
Procedure D2A0Out( x : integer);
var
 LowByte, HighByte : integer;
begin
 LowByte : = (xAND $F) * 16;
 HighByte : = xDIV 16;
 port[BaseAddr + 4] : = LowByte;
 port[BaseAddr + 5] : = HighByte; {output not upddated
                                   until High byte sent}
end; { D2A0Out }

Procedure GetHeap;

Procedure Bye;
begin
 writeln('Sorry, not enough memory available for heap!');
 halt(1);
end; { Bye } begin { GetHeap }
 if MaxAvail < SizeOf(datbuf) then Bye;
 GetMem(peak, SizeOf(datbuf));
 if MaxAvail < SizeOf(datbuf) then Bye;
 GetMem(mean, SizeOf(datbuf));
 if MaxAvail < SizeOf(datbuf) then Bye;
 GetMem(period, SizeOf(datbuf));
end; { GetHeap }

Procedure FreeHeap;
begin
 FreeMem(peak, SizeOf(datbuf));
 FreeMem(mean, SizeOf(datbuf));
 FreeMem(period, SizeOf(datbuf));
end; { FreeHeap }
Function FileExist(fn : string) : boolean;
var
```

```
                                  30
 fp : text;
begin
 Assign(fp, fn);
 {$i} Reset(fp); {$i+}
 if IoResult <> 0 then
  FileExist : = false
 else
 begin
  Close(fp);
  FileExist : = true;
 end;
end; { FileExist }

Function init : boolean; {test input file & init D/A BaseAddr}
var
 P : PathStr;
 D : DirStr;
 N : NameStr;
 E : ExtStr;
 fp : Text;

begin
 if (ParamCount = 0) or (FileExist(ParamStr(1)) = false) then
 begin
  init : false;
  exit;
 end;

{ Load D/A Configuration file }
 P : = ParamStr(0); { full pathname to program running }
 FSplit(P, D, N, E);
 Assign(fp, D + N + '.cfg');
 {$i-} Reset(fp); {$i +}
 if IoResult < > 0 then {file missing, create a default one} begin
```

31

```
ReWrite(fp);
BaseAddr : = 784;
writeln(fp, BaseAddr); (* Al's machine D/A uses & H310 base
address *)
end
else
  readln(fp, BaseAddr);
close(fp);
D2A0Out(0);   { send a 0 to D/A to init }
init : = true;
end; { init }
{              Sample File Format
"Data file: C:\CODAS\MUTCH3"
"Source channel: 6"
"Engineering units: mm Hg"
"Sample ra""te of cha""nnel:"  160
"Cycle type: Peak to Valley"
"Cycles pe""r average""": "1
"Valley"," Peak"," Mean"," Sec"," S/N Vly"," S/N Pk"
9.660E+01, 1.335E+02, 1.157E+02, 1.5625E-01, 5.500000E+01,
3.000000E+01
9.635E+01, 1.334E+02, 1.171E+02, 1.4375E-01, 1.160000E+02,
9.300000E+01
}

Procedure LoadPeakRates(fn : string; Var numgot : integer);
var
  fp : text;
  t : string;
  i : integer;
  valley : single;
Function GetReal : single; { Codas file contains[,] so string
bang it}
var
  ierr : integer;
  tmp : string;
```

32

```
x : single;
begin
 while t[1] = ' ' do Delete(t, 1, 1); {leading delete []'s}
 if t[Length(t)] < > ',' then t : = t + ','; {force[,] at end of
 str} tmp : = Copy(t, 1, Pos(',', t) - 1);
 Val(tmp, x, ierr);
 if ierr < > 0 then
 begin
  writeln('an error occurred converting [', tmp, ']');
  Close(fp);
  halt(1);
 end;

Delete(t, 1, Pos(',', t));  {remove value converted from str}
 GetReal : = x;
end; { GetReal } begin { LoadPeakRates }
 Assign(fp, fn);
 {$i-} Reset(fp); {$i+}
 if IoResult < > 0 then halt(1);   { file existed previously} i : = 0;  { init line counter }
 numgot : = 0;

while (not Eof(fp)) and (numgot < MAXBUF) do
 begin
  inc(i);
  readln(fp, t);

if i < 10 then    { list header while loading file }
  begin
   while Pos('"', t) > 0 do  { delete ["]'s for easy reading }
    Delete(t, Pos('"', t), 1);
```

```
                              33
 writeln(t);
end
else
begin
 inc(numgot);
 if numgot < = 10 then writeln(t); { list 1st 10 lines }
 valley : = GetReal;
 peak"[numgot] : = GetReal;
 mean"[numgot] : = GetReal;
 period"[numgot] : = GetReal;
{  writeln(valley:13:-4, peak"[numgot]:13:-4,
    mean"[numgot]:13:-4, period"[numgot]:13:-4);   } end;
end;  { while not eof }

Close(fp);

if numgot = MAXBUF then
  writeln('***data buffer only contains first ', MAXBUF,
    ' file entries ***');
end; { LoadPeakRates}

Function Min(x, y : single) : single;
begin
 if x < y then
  Min : = x
 else
  Min : = y;
end;  { Min }

Function Max(x, y : single) : single;
begin
 if x > y then
  Max : = x
 else
```

```
  Max : = y;
end;  { Max }

Procedure CalStat(Var col : datdef; Var stat : statdef;n :
integer);
{ Generaric calculate min, max, and avg of one column }
var
 i : integer;
begin
 stat[1] : = col^[1];   { init min }
 stat[2] : = col^[1];   { init max }
 stat[3] : = 0;         { init summation } for i : = 1 to n do
 begin
  stat[1] : = Min(stat[1], col^[i]);
  stat[2] : = Max(stat[2], col^[1]);
  stat[3] : = stat[3] + col^[1];
 end;
 stat[3] : = stat[3] / Int(n);
end;  { CalStat }

Procedure GetStats(n : integer); { cal min, max, & avg of data
loaded }
var
 i : integer;
begin
 if n < 2 then exit;  { nothing to do }
CalStat(peak, peakstat, n);
CalStat(mean, meanstat, n);
CalStat(period, periodstat, n);

{ report }
 writeln;
 writeln(' ':15, 'Peak':15, 'Mean':15, 'Period:15);
 writeln('Min':15, peakstat[1]:15:3, meanstat[1]:15:3,
```

35

```
  periodstat[1]:15:3, periodstat[1]:15:5);
  writeln('Max':15, peakstat[2]:15:3, meanstat[2]:15:3,
  periodstat[2]:15:5);
  writeln('Avg':15, peakstat [3]:15:3, meanstat[3]:15:3,
  periodstat[3]:15:5);
  writeln;
end; { GetStats }

Procedure RemoveMinFromPeak(n : integer);
var
  i : integer;
begin
  for i : = 1 to n do
    peak^[i] : = peak^[i] - peakstat[1]; { remove min from peak
    column }
  peakstat[2] : = peakstat[2] - peakstat[1];
  peakstat[1] : = 0;
end: { RemoveMinFromPeak }

Procedure Pause(seconds : single);
Type
  timerec = record
          hr, min, sec, hund : word;
          end;
var
  tnow, tend : timerec;
  t1, t2 : longint;

Function Time2Long( time : timerec) : longint;
var
  t : longint;
  hr, min, sec, hund : longint;
begin
  hr : = time.hr;
  min : = time.min;
  sec : = time.sec;
```

36

```
  hund : = time.hund;
  t : = hund + sec * 100 + min * 100 * 60 + hr * 100 * 60 * 60;
  Time2Long : = t;
end;   { Time2Long } begin   { Pause }
  with tend do GetTime(hr, min, sec, hund); { Get Current Time }

{ add seconds passed in to tend to know stop time }
  with tend do
begin
  hund : = hund + Round(Frac(seconds) * 100.0);
  sec : = sec + Trunc(Int(seconds));

if hund > 99 then
begin
  hund : = hund - 100;
  sec : = sec + 1;
end;

while sec > 59 do
begin
  sec : = 60;
  min : = min + 1;
end;

while min > 59 do
begin
  min : = - 60;
  hr : = hr + 1;
end;

while hr > 23 do
  hr : = hr - 24;

end;   { with tend }
```

```
                              37
t2 : = Time2Long(tend);

repeat
 with tnow do GetTime(hr, min, sec, hund);  {Get Time now } tnow
 t1 : = Time2Long(tnow);
until t1 > = t2;
end;  { Pause }

Procedure ListWithPause(n : integer);
var
 i, d2a : integer;
begin
 for i : = 1 to n do
begin
 d2a : = Round(peak^[i] / peakstat[2] * 4095.0);
 writeln(i:5, peak^[i]:10:1, period^[i]:10:4, d2a:10);
 Pause(period^[i]);
end;  { for i : = }
end;  { ListWithPause }

Procedure SendToD2A(n : integer);
var
 i, d2a : integer;
 up, done, first : boolean;
 ch : char;

begin
 done : = false;
 first : = true; { flag for 1st pass }
 up : = true  { scan data upwwards first }
 i : =    { data pointer } while Not Done do
begin
 if (up) and (i = n) then up : = false;  { Up or Down }
 if (Not up) and (i = 1) then up : = true;
```

```
                                        38
  if first then   { 1st pass only }
     first : = false else    { normal data pointer incr/dec }
  begin
   if up then
     Inc(i)
  else
     Dec(i);
  end;

d2a : = Round(peak^[i] / peakstat[2] * 4095.0);
  D2A0Out(d2a);
  Pause(period^[i]);

if Key Pressed then
  begin
    ch : = ReadKey;
    if ch = Chr(27) then done : = true;
   end;
  end;   { while not Done }
  end;   { SendToD2A } var
 n : integer;
 ch : char;

begin   { Main }
 if not init then
 begin
 writeln('Purfus filename.exc');
 halt(1);
end;

ClrScr;
 GetHeap;
```

39

```
TextBackGround(1);
TextColor(7);

writeln('loading ', ParamStr(1));
LoadPeakRates(ParamStr(1), n);
writeln('Loaded ',n, ' data points');
GetStats(n);
RemoveMinFromPeak(n);   { remove min value from Peak column }
GetStats(n);

writeln('Press any key to continue');
ch : = ReadKey;

ClrScr;
writeln('**** Calibration ****');
writeln;
writeln('Set the Pump Rate to desired Blood Pressure');
writeln('Press any key to continue');
ch : = ReadKey;
writeln;

writeln('Adjust the Variability Level Control to 0 (CCW) Now!');
writeln('Press any key to continue');
ch : = ReadKey;
writeln;

writeln('Set the Variability Level Control to desired MAX Peak
Blood Pressure');
D2A0Out(4095);  { set D/A output to 5 volts }
writeln('Press any key to continue');
ch : = ReadKey;
D2A0Out(0);   { set D/A output to 0 volts }
writeln;

writeln('About to start Pump Control Loop');
writeln('Press any key to continue');
```

```
                              40
 ch : = ReadKey;
 writeln;
 writeln('Press ESC to terminate Control of Pump Rate');

{ ListWithPause(n); }
  SendToD2A(n);

D2A0Out(0);   { reset D/A to 0 on exit }
 FreeHeap;
 TextBackGround(0);
 TextColor(7);
end.
```

Vent.Bas - Main of Ventilator Control        TABLE 2

```
'$Title:'Vent.Bas - Main of Ventilator Control' $LineSize:112'

'Vent.Bas
'Chris McLennan
'Oct 11/93

'MenuSys.Bas
DECLARE SUB GetConfig ()
DECLARE SUB Init ()
DECLARE SUB MainMenu ()
DECLARE SUB SetConfig (Mode AS INTEGER)
DECLARE SUB TestGrModes ()

'DasLib.Bas
DECLARE SUB InitDas16 ()

'VentLib.Bas
DECLARE SUB InitVentLib ()

'$INCLUDE: 'DasLib.Bi1'
'---------- DasLib.Bi1 ----------

'Das16 Common Area

'Das16 Parameters MUST be in common

CONST A2dBuffSize = 2000

DIM Dio(4) AS INTEGER
 DIM A2dBuff(2000) AS INTEGER
 DIM A2dChNum(2000) AS INTEGER COMMON Dio() AS INTEGER, Md AS INTEGER, Flag AS INTEGER
 COMMON BiPolar AS INTEGER, DasChan AS INTEGER, VoltFS AS SINGLE
 COMMON A2dBuff() AS INTEGER          'Buffer for DasMode4
 COMMON A2dChNum() AS INTEGER         'Buffer for A/D channel info 'for Mode 5 & 6, Quick Basic manages the Data Segment '$DYNAMIC
 'Dynamic Common is dimensioned AFTER the COMMON specification CONST A2dBuf2Size = 2000
 COMMON A2dBuf2() AS INTEGER        'Buffer for A/D data

'$STATIC

'---------- End DasLib.Bi1 ----------
```

```
Vent.Bas - Main of Ventilator Control                                    PAGE   2
                                                                         21 Nov 93
                                                                         14:48:59
                                                Microsoft (R) QuickBASIC Compiler Version 4.50

'$INCLUDE: 'MenuSys.Bi1'
    '---------- MenuSys.Bi1----------

' Constants for best available screen mode
    CONST VGA = 12
    CONST MCGA = 13
    CONST EGA256 = 9
    CONST EGA64 = 8
    CONST MONO = 10
    CONST HERC = 3
    CONST CGA = 1

' User-defined type to hold information about the mode
    TYPE Config
        Scrn     AS INTEGER
        Colors   AS INTEGER
        Atribs   AS INTEGER
        XPix     AS INTEGER
        YPix     AS INTEGER
        TCOL     AS INTEGER
        TROW     AS INTEGER
    END TYPE '*****Graphics Modes
    COMMON VC AS Config, InitRows AS INTEGER, BestMode AS INTEGER, Available AS STRING '*****Menu system
    '$DYNAMIC
    COMMON PopBuf() AS INTEGER, CurPath$, ForGnd AS INTEGER, Bakgnd AS INTEGER
    '$STATIC '---------- End MenuSys.Bi1----------

'$INCLUDE: 'VentLib.Bi1'
    '---------- VentLib.Bi1 ----------

'VentLib Dynamic Common declaration

TYPE VentDat           'Structure to hold modulation data
        Time AS SINGLE
        Mode AS STRING * 1
        Modulation AS SINGLE
    END TYPE CONST VentArrSize = 2000

COMMON VentArrNum AS INTEGER      '# of items loaded in VentArr()
    COMMON VentDatFn$                 'Data File loaded '$DYNAMIC
    'Dynamic Common is dimensioned AFTER the COMMON specification
```

Vent.Bas - Main of Ventilator Control

```
                                                              PAGE   3
                                                              21 Nov 93
                                                              14:48:59
                                    Microsoft (R) QuickBASIC Compiler Version 4.50

COMMON VentArr() AS VentDat      'Buffer for Ventilator modulation data

'$STATIC

'---------- End VentLib.Bi1 ----------

'$INCLUDE: 'DasLib.BI2'
'---------- DasLib.BI2 ----------
   DIM A2dBuf2(A2dBuf2Size) AS INTEGER
'---------- End DasLib.BI2 ----------

'$INCLUDE: 'MenuSys.BI2'
'---------- MenuSys.BI2----------
   DIM PopBuf(2002, 1) AS INTEGER   'PopUp Buffer
'---------- End MenuSys.BI2----------

'$INCLUDE: 'VentLib.BI2'
'---------- VentLib.BI2 ----------
   DIM VentArr(VentArrSize) AS VentDat   'Buffer for Ventilator modulation data
'---------- End VentLib.BI2 ----------

InitDas16                        'General Reset of Das16
   InitVentLib                      'Clear Commons 'Determine Graphic Card
   GetConfig
   VC.Scrn = BestMode
   SetConfig VC.Scrn                'loads record VC with graphic mode parameters ' TestGrModes Init
   MainMenu
   COLOR 7, 0
   END 43933 Bytes Available
41609 Bytes Free 0 Warning Error(s)
    0 Severe  Error(s)
```

44

DasLib.Bas - Das16 Library                                                                 PAGE   1
                                                                                          21 Nov 93
                                                                                          14:49:00
                                                        Microsoft (R) QuickBASIC Compiler Version 4.50

```
'$Title:'DasLib.Bas - Das16 Library' $LineSize:112'
'DasLib

'Das16 Library Interface
'Oct 2/93
'Chris McLernan

'MenuSys.Bas
DECLARE FUNCTION Exist! (FileName$)

DECLARE SUB DAS16 (MODE%, BYVAL dummy%, Flag%)

DECLARE SUB DasMode0 ()
DECLARE SUB DasMode1 (ChLow AS INTEGER, ChHigh AS INTEGER)
DECLARE SUB DasMode2 (NextCh AS INTEGER, ChLow AS INTEGER, ChHigh AS INTEGER)
DECLARE SUB DasMode3 (A2dData AS INTEGER, A2dCh AS INTEGER)
DECLARE SUB DasMode4 (NumPts AS INTEGER)
DECLARE SUB DasMode5 (NumPts AS INTEGER, Cycle AS INTEGER)
DECLARE SUB DasMode6 (NumPts AS INTEGER, Cycle AS INTEGER)
DECLARE SUB DasMode7 ()
DECLARE SUB DasMode8 (Op AS INTEGER, Status AS INTEGER, Count AS INTEGER)
DECLARE SUB DasMode9 (NumPts AS INTEGER, StartPt AS INTEGER)
DECLARE SUB DasMode15 (D2aCh AS INTEGER, D2aData AS INTEGER)
DECLARE SUB DasMode16 (D2aDat0 AS INTEGER, D2aDat1 AS INTEGER)
DECLARE SUB DasMode17 (Rate!)
DECLARE SUB DasError (code AS INTEGER)

DECLARE FUNCTION A2dToVolt! (A2dVal AS INTEGER)
DECLARE FUNCTION IntToReal! (x AS INTEGER)
DECLARE FUNCTION RealToInt% (x!)
DECLARE FUNCTION VoltToD2a% (volt!)

'$INCLUDE: 'DasLib.Bi1'
'---------- DasLib.Bi1 ----------

'Das16 Common Area

'Das16 Parameters MUST be in common

CONST A2dBuffSize = 2000

DIM Dio(4) AS INTEGER
DIM A2dBuff(2000) AS INTEGER
DIM A2dChNum(2000) AS INTEGER COMMON Dio() AS INTEGER, Md AS INTEGER, Flag AS INTEGER
COMMON BiPolar AS INTEGER, DasChan AS INTEGER, VoltFS AS SINGLE
COMMON A2dBuff() AS INTEGER              'Buffer for DasMode4
COMMON A2dChNum() AS INTEGER             'Buffer for A/D channel info 'for Mode 5 & 6, Quick Basic manages the Data Segment
```

DasLib.Bas - Das16 Library                                                    PAGE   2
                                                                              21 Nov 93
                                                                              14:49:00
                                          Microsoft (R) QuickBASIC Compiler Version 4.50

```
'$DYNAMIC
'Dynamic Common is dimensioned AFTER the COMMON specification

CONST A2dBuf2Size = 2000
COMMON A2dBuf2() AS INTEGER        'Buffer for A/D data

'$STATIC

'---------- End DasLib.Bi1 ----------

'$INCLUDE: 'DasLib.Bi2'
'---------- DasLib.Bi2 ----------
 DIM A2dBuf2(A2dBuf2Size) AS INTEGER
'---------- End DasLib.Bi2 ----------

'$Page $SubTitle:'FUNCTION A2dToVolt'
```

DasLib.Bas - Das16 Library
FUNCTION A2dToVolt

PAGE 3
21 Nov 93
14:49:00
Microsoft (R) QuickBASIC Compiler Version 4.50

```
FUNCTION A2dToVolt (A2dVal AS INTEGER)

'Returns A2d value converted into voltage

SHARED BiPolar AS INTEGER, VoltFS AS SINGLE

IF BiPolar THEN
    A2dToVolt = A2dVal / 2048! * VoltFS
  ELSE
    A2dToVolt = A2dVal / 4096! * VoltFS
  END IF

END FUNCTION

'$Page $SubTitle:'SUB DasError'
```

47

```
DasLib.Bas - Das16 Library
SUB DasError                                                           PAGE   4
                                                                       21 Nov 93
                                                                       14:49:00
                                          Microsoft (R) QuickBASIC Compiler Version 4.50

SUB DasError (code AS INTEGER)
    SELECT CASE code
        CASE 0
            PRINT "OK"
        CASE 1
            PRINT "Driver not initialized"
        CASE 2
            PRINT "Mode number out of range"
        CASE 3
            PRINT "Base Address out of range"
        CASE 4
            PRINT "Interrupt Level out of range"
        CASE 5
            PRINT "DMA Level out of range"
        CASE 6
            PRINT "Differential Mux scan limits out of range"
        CASE 7
            PRINT "Single Ended Mux scan limits out of range"
        CASE 8
            PRINT "Error Code 8?"
        CASE 9
            PRINT "A/D Timeout Error - hardware - no EOC"
        CASE 10
            PRINT "Counter division ratio 0 or 1 in mode 17"
        CASE 11
            PRINT "Number of conversions <= 0 in modes 4,5, or 6"
        CASE 12
            PRINT "Counter configuration # out of range in mode 10"
        CASE 13
            PRINT "Digital output data out of range in mode 13"
        CASE 14
            PRINT "D/A data out of range in modes 15 or 16"
        CASE 15
            PRINT "D/A channel # out of range"
        CASE 16
            PRINT "Counter read operation not 0 or 1 in mode 12"
        CASE 17
            PRINT "Start conversion negative # in mode 9"
        CASE 18
            PRINT "Word count 0 or negative in mode 9"
        CASE 19
            PRINT "Trigger mode not 0 or 1 in modes 4,5, or 6"
        CASE 20
            PRINT "DMA / Interrupt operation already active in modes 5 or 6"
        CASE 21
            PRINT "DMA page wrap around in mode 6"
        CASE 22
            PRINT "Hardware failure or installation error [Base Address?]"
        CASE 23
            PRINT "Trigger channel inconsistent with configuration [mode 19]"
        CASE 24
            PRINT "Trigger data out of range [mode 19]"
        CASE 25
```

DasLib.Bas - Das16 Library
SUB DasError

PAGE 5
21 Nov 93
14:49:00
Microsoft (R) QuickBASIC Compiler Version 4.50

```
        PRINT "Slope data not 0 or 1 [mode 19]"
    END SELECT

END SUB

'$Page $SubTitle:'SUB DasMode0'
```

49

DasLib.Bas - Das16 Library　　　　　　　　　　　　　　　　　　　　　　　　　PAGE   6
SUB DasMode0　　　　　　　　　　　　　　　　　　　　　　　　　　　　　　　　　21 Nov 93
　　　　　　　　　　　　　　　　　　　　　　　　　　　　　　　　　　　　　　　14:49:00
　　　　　　　　　　　　　　　　　　　　　　　　　Microsoft (R) QuickBASIC Compiler Version 4.50

```
SUB DasMode0

'INIT DAS16 DRIVER
    'Use NEW format file Das16Adr.Cfg for Card Initialization SHARED Dio() AS INTEGER, Md AS INTEGER, Flag AS INTEGER
    SHARED BiPolar AS INTEGER, DasChan AS INTEGER, VoltFS AS SINGLE DIM fp AS INTEGER, Status AS INTEGER IF NOT Exist("Das16Adr.Cfg") THEN
      CLS
      PRINT "Das16 Configuration file [Das16Adr.Cfg] not found"
      END
    END IF OPEN "Das16Adr.Cfg" FOR INPUT AS #1
    INPUT #1, Dio(0)            'get base I/O address
    INPUT #1, Dio(1)            'interrupt level
    INPUT #1, Dio(2)            'D.M.A. level
    INPUT #1, VoltFS            'Voltage Range
    CLOSE #1

Flag = 0                    'error variable
    Md = 0                      'mode 0 - initialize
    CALL DAS16(Md, VARPTR(Dio(0)), Flag)
    IF Flag <> 0 THEN
      DasError (Flag)
      END
    END IF '---- Find DASH-16 operating configurations ----
    'read status register at base address + 8
    Status = INP(Dio(0) + 8)

IF (Status AND &H40) = &H40 THEN       ' BIPOLAR OR UNIPOLAR
      BiPolar = 0
    ELSE
      BiPolar = -1
    END IF IF (Status AND &H20) = &H20 THEN
      DasChan = 16
    ELSE
      DasChan = 8               ' # CHANNELS
    END IF

END SUB

'$Page $SubTitle:'SUB DasMode1'
```

```
DasLib.Bas - Das16 Library                                               PAGE    7
SUB DasMode1                                                            21 Nov 93
                                                                         14:49:00
                                         Microsoft (R) QuickBASIC Compiler Version 4.50

SUB DasMode1 (ChLow AS INTEGER, ChHigh AS INTEGER)

'SET MULTIPLEXER SCAN LIMITS

SHARED Dio() AS INTEGER, Md AS INTEGER, Flag AS INTEGER

IF ChLow > ChHigh THEN SWAP ChLow, ChHigh

Dio(0) = ChLow     'LOW LIMIT
  Dio(1) = ChHigh    'HIGH LIMIT
  Md = 1
  CALL DAS16(Md, VARPTR(Dio(0)), Flag)

IF Flag <> 0 THEN
    DasError (Flag)
    END
  END IF

END SUB

'$Page $SubTitle:'SUB DasMode15'
```

```
-DasLib.Bas - Das16 Library                                              PAGE   8
 SUB DasMode15                                                          21 Nov 93
                                                                        14:49:00
                                       Microsoft (R) QuickBASIC Compiler Version 4.50

SUB DasMode15 (D2aCh AS INTEGER, D2aData AS INTEGER)

'Output Data to one D/A Channel

'If the -5vRev is connected to the D/A Ref In on the DB 37,
   'an output from 0 to 5V is generated.

SHARED Dio() AS INTEGER, Md AS INTEGER, Flag AS INTEGER

Dio(0) = D2aCh      'Channel #[0..1] to send to
   Dio(1) = D2aData    'Data to send [0..4095]
   Md = 15
   CALL DAS16(Md, VARPTR(Dio(0)), Flag)
   IF Flag <> 0 THEN
     DasError (Flag)
     END
   END IF
 END SUB '$Page $SubTitle:'SUB DasMode16'
```

```
DasLib.Bas - Das16 Library
SUB DasMode16                                                           PAGE   9
                                                                        21 Nov 93
                                                                        14:49:00
                                     Microsoft (R) QuickBASIC Compiler Version 4.50

SUB DasMode16 (D2aDat0 AS INTEGER, D2aDat1 AS INTEGER)

'Output Data to both D/A Channels

'If the -5vRev is connected to the D/A Ref In on the DB 37,
  'an output from 0 to 5V is generated.

SHARED Dio() AS INTEGER, Md AS INTEGER, Flag AS INTEGER

Dio(0) = D2aDat0   'Channel 0
  Dio(1) = D2aDat1   'Channel 1
  Md = 16
  CALL DAS16(Md, VARPTR(Dio(0)), Flag)
  IF Flag <> 0 THEN
    DasError (Flag)
    END
  END IF

END SUB

'$Page $SubTitle:'SUB DasMode17'
```

53

```
DasLib.Bas - Das16 Library                                              PAGE  10
SUB DasMode17                                                           21 Nov 93
                                                                        14:49:00
                                        Microsoft (R) QuickBASIC Compiler Version 4.50

SUB DasMode17 (Rate)

'COMPUTE SCAN RATE PER CHANNEL FOR A/D
 '
 ' HZ = 1,000,000 / ( N1 * N2 )
 '
 '   WHERE  2 < N1 & N2 > 65535
 '
 SHARED Dio() AS INTEGER, Md AS INTEGER, Flag AS INTEGER DIM NextCh AS INTEGER, ChLow AS INTEGER, ChHigh AS INTEGER
 DIM Sr, HzMin, HzMax, Prod, Seed1, Seed2, NumCh AS INTEGER 'DETERMINE # CHANNELS IN USE
 NextCh = 0
 ChLow = 0
 ChHigh = 0
 CALL DasMode2(NextCh, ChLow, ChHigh)
 NumCh = ChHigh - ChLow + 1        ' NUMCH 'CAL SCAN RATE PER CHANNEL
 Sr = Rate * NumCh 'FIX RATE OVERFLOWS
 HzMax = 1000000! / 4
 HzMin = 1000000! / (65535! * 65535!)
 IF Sr > HzMax THEN Sr = HzMax
 IF Sr < HzMin THEN Sr = HzMin 'TRICKY ROUTINE
 '
 Prod = 1000000! / Sr       'PROD = N1 * N2
 Seed1 = 2                  'STARTING VALUE OF SEED1

DO
    IF Prod / Seed1 <= 65535 THEN EXIT DO       'SEED2 WILL BE VALID

Seed1 = INT(Seed1 * 2)                      'DOUBLE NEXT GUESS FOR SEED1
    IF Seed1 > 65535 THEN Seed1 = 65535         '& TEST FOR OVERFLOW
 LOOP Seed2 = INT(Prod / Seed1)

'CALL DASH16
 Md = 17

Dio(0) = RealToInt(Seed1)
 Dio(1) = RealToInt(Seed2)

'PRINT Dio(0), Dio(1), 1000000 / (Seed1 * Seed2)

CALL DAS16(Md, VARPTR(Dio(0)), Flag)
 IF Flag <> 0 THEN
   DasError (Flag)
```

```
DasLib.Bas - Das16 Library                                                    PAGE  11
SUB DasMode17                                                                21 Nov 93
                                                                             14:49:00
                                             Microsoft (R) QuickBASIC Compiler Version 4.50

END
   END IF
END SUB

'$Page $SubTitle:'SUB DasMode2'
```

```
DasLib.Bas - Das16 Library                                              PAGE 12
SUB DasMode2                                                            21 Nov 93
                                                                        14:49:00
                                        Microsoft (R) QuickBASIC Compiler Version 4.50

SUB DasMode2 (NextCh AS INTEGER, ChLow AS INTEGER, ChHigh AS INTEGER)
  'READ CURRENT MULTIPLEXER ADDRESS AND SCAN LIMITS SHARED Dio() AS INTEGER, Md AS INTEGER, Flag AS INTEGER Md = 2
  CALL DAS16(Md, VARPTR(Dio(0)), Flag)
  IF Flag <> 0 THEN
    DasError (Flag)
    END
  END IF NextCh = Dio(0)     'NEXT CHANNEL TO CONVERT
  ChLow = Dio(1)      'LOWER SCAN LIMIT
  ChHigh = Dio(2)     'UPPER SCAN LIMIT
END SUB '$Page  $SubTitle:'SUB DasMode3'
```

```
DasLib.Bas - Das16 Library                                              PAGE  13
SUB DasMode3                                                         21 Nov 93
                                                                     14:49:00
                                         Microsoft (R) QuickBASIC Compiler Version 4.50

SUB DasMode3 (A2dData AS INTEGER, A2dCh AS INTEGER)

'Do one A/D conversion and increment Mux

SHARED Dio() AS INTEGER, Md AS INTEGER, Flag AS INTEGER

Md = 3
  CALL DAS16(Md, VARPTR(Dio(0)), Flag)
  IF Flag <> 0 THEN
    DasError (Flag)
    END
  END IF A2dData = Dio(0)   'A/D data
  A2dCh = Dio(1)     'A/D Channel
END SUB '$Page $SubTitle:'SUB DasMode4'
```

DasLib.Bas - Das16 Library
SUB DasMode4

```
SUB DasMode4 (NumPts AS INTEGER)

'Do NumPts A/D conversions directly to array A2dBuff()

SHARED Dio() AS INTEGER, Md AS INTEGER, Flag AS INTEGER
  SHARED A2dBuff() AS INTEGER IF NumPts > A2dBuffSize THEN NumPts = A2dBuffSize Dio(0) = NumPts              '# pts to convert
  Dio(1) = VARPTR(A2dBuff(0))  'output array location
  Dio(2) = 1                   'trigger source, 1=timer, 0=external on IP0
  'Note: If the timer is used as a trigger source then holding input IP0
  '      low will delay starting conversions.
  Md = 4
  CALL DAS16(Md, VARPTR(Dio(0)), Flag)
  IF Flag <> 0 THEN
    DasError (Flag)
    END
  END IF
END SUB '$Page $SubTitle:'SUB DasMode5'
```

DasLib.Bas - Das16 Library
SUB DasMode5

PAGE 15
21 Nov 93
14:49:00
Microsoft (R) QuickBASIC Compiler Version 4.50

```
SUB DasMode5 (NumPts AS INTEGER, Cycle AS INTEGER)

'Do NumPts A/D conversions and transfer to memory on INTERRUPT

'This uses Dynamically allocated A2dBuf2 in common data segment
  'This runs in the background
  'Data is accessed by DasMode9

'Cycle = 0 for One Scan and finish
  '      = 1 for Continuous Scanning --> DasMode7 to stop SHARED Dio() AS INTEGER, Md AS INTEGER, Flag AS INTEGER
  SHARED A2dBuf2() AS INTEGER IF NumPts > A2dBuf2Size THEN NumPts = A2dBuf2Size Dio(0) = NumPts                '# pts to convert
  Dio(1) = VARSEG(A2dBuf2(0))    'output array location
  Dio(2) = 1                     'trigger source, 1=timer, 0=external on IP0
  'Note: If the timer is used as a trigger source then holding input IP0
  '      low will delay starting conversions.
  Dio(3) = Cycle                 '0 = One shot and finish
                                 '1 = Continuous Scanning - Mode7 to stop
  Md = 5
  CALL DAS16(Md, VARPTR(Dio(0)), Flag)
  IF Flag <> 0 THEN
    DasError (Flag)
    DasMode7
    END
  END IF

END SUB

'$Page $SubTitle:'SUB DasMode6'
```

59

```
DasLib.Bas - Das16 Library                                                    PAGE  16
SUB DasMode6                                                                  21 Nov 93
                                                                              14:49:00
                                                Microsoft (R) QuickBASIC Compiler Version 4.50

SUB DasMode6 (NumPts AS INTEGER, Cycle AS INTEGER)

'Do NumPts A/D conversions and transfer to memory via DMA

'This uses Dynamically allocated A2dBuf2 in common data segment
  'This runs in the background
  'Data is accessed by DasMode9

'Cycle = 0 for One Scan and finish
  '      = 1 for Continuous Scanning --> DasMode7 to stop SHARED Dio() AS INTEGER, Md AS INTEGER, Flag AS INTEGER
  SHARED A2dBuf2() AS INTEGER IF NumPts > A2dBuf2Size THEN NumPts = A2dBuf2Size Dio(0) = NumPts              '# pts to convert
  Dio(1) = VARSEG(A2dBuf2(0))  'output array location
  Dio(2) = 1                   'trigger source, 1=timer, 0=external on IP0
  'Note: If the timer is used as a trigger source then holding input IP0
  '      low will delay starting conversions.
  Dio(3) = Cycle               '0 = One shot and finish
                               '1 = Continuous Scanning - Mode7 to stop
  Md = 6
  CALL DAS16(Md, VARPTR(Dio(0)), Flag)
  IF Flag <> 0 THEN
    DasError (Flag)
    DasMode7
    END
  END IF

END SUB

'$Page  $SubTitle:'SUB DasMode7'
```

```
DasLib.Bas - Das16 Library                                              PAGE  17
SUB DasMode7                                                          21 Nov 93
                                                                       14:49:00
                                      Microsoft (R) QuickBASIC Compiler Version 4.50

SUB DasMode7
  'DISABLE DMA/INTERRUPT OPERATION OF A/D

SHARED Dio() AS INTEGER, Md AS INTEGER, Flag AS INTEGER

Md = 7
  CALL DAS16(Md, VARPTR(Dio(0)), Flag)
  IF Flag <> 0 THEN
    DasError (Flag)
    END
  END IF

END SUB

'$Page $SubTitle:'SUB DasMode8'
```

DasLib.Bas - Das16 Library
SUB DasMode8

PAGE 18
21 Nov 93
14:49:00
Microsoft (R) QuickBASIC Compiler Version 4.50

```
SUB DasMode8 (Op AS INTEGER, Status AS INTEGER, Count AS INTEGER)

'allows monitor of mode 5,6,18, or 20 Background operation

'Op = 0 none
  '   = 1 Mode 6  [DMA]
  '   = 2 Mode 5  [Interrupt]
  '   = 3 Mode 18 [Interrupt]
  '   = 4 Mode 20 [Interrupt]

'Status = 0 if Done or 1 in Active

'Count = Current word count [# conversions so far]
  '      = 0 to (Num Chan * pts per chan) - 1
  ' ex   = 4 channels @ 200 pts per channel = [0..799]
  '      = seems to indicate the current conversion - which is not yet done.

SHARED Dio() AS INTEGER, Md AS INTEGER, Flag AS INTEGER

Md = 8
  CALL DAS16(Md, VARPTR(Dio(0)), Flag)
  IF Flag <> 0 THEN
    DasError (Flag)
    END
  END IF Op = Dio(0)         'Operation type
  Status = Dio(1)     'Status of Operation
  Count = Dio(2)      'Current word count

END SUB

'$Page $SubTitle:'SUB DasMode9'
```

```
DasLib.Bas - Das16 Library                                              PAGE  19
SUB DasMode9                                                          21 Nov 93
                                                                       14:49:00
                                         Microsoft (R) QuickBASIC Compiler Version 4.50

SUB DasMode9 (NumPts AS INTEGER, StartPt AS INTEGER)

'Transfer Data from A2dBuf2() to A2dBuff() [from memory to array]
  'Channel information transferred into A2dChNum()
  'StartPt is starting conversion # - usually zero SHARED Dio() AS INTEGER, Md AS INTEGER, Flag AS INTEGER
  SHARED A2dBuf2() AS INTEGER              'input area
  SHARED A2dBuff() AS INTEGER              'output area for data
  SHARED A2dChNum() AS INTEGER             'output area for channel #'s IF NumPts > A2dBuf2Size THEN NumPts = A2dBuf2Size Dio(0) = NumPts                  '# pts to convert
  Dio(1) = VARSEG(A2dBuf2(0))      'input array location
  Dio(2) = StartPt                 'start transferring at conversion StartPt
  Dio(3) = VARPTR(A2dBuff(StartPt))  'Destination of Data to transfer
  Dio(4) = VARPTR(A2dChNum(StartPt)) 'Destination of chan # Data to transfer
  Md = 9
  CALL DAS16(Md, VARPTR(Dio(0)), Flag)
  IF Flag <> 0 THEN
    DasError (Flag)
    DasMode7
    END
  END IF

END SUB

'$Page $SubTitle:'FUNCTION IntToReal'
```

63

DasLib.Bas - Das16 Library  
FUNCTION IntToReal

PAGE 20
21 Nov 93
14:49:00
Microsoft (R) QuickBASIC Compiler Version 4.50

```
FUNCTION IntToReal (x AS INTEGER)

'CONVERT SIGNED INTEGER TO REAL   [-32768 <==> 32767]

IF x >= 0 THEN
     IntToReal = x
   ELSE
     IntToReal = x + 65536
   END IF

END FUNCTION

'$Page $SubTitle:'FUNCTION RealToInt%'
```

64

DasLib.Bas - Das16 Library  
FUNCTION RealToIntX

PAGE 21  
21 Nov 93  
14:49:00  
Microsoft (R) QuickBASIC Compiler Version 4.50

```
FUNCTION RealToIntX (x)
    'CONVERT REAL TO SIGNED INTEGER  [-32768 <==> 32767]

IF x <= 32767 THEN
        RealToIntX = x
    ELSE
        RealToIntX = x - 65536
    END IF
END FUNCTION '$Page  $SubTitle:'FUNCTION VoltToD2aX'
```

```
DasLib.Bas - Das16 Library                                                    PAGE  22
FUNCTION VoltToD2aX                                                          21 Nov 93
                                                                              14:49:00
                                           Microsoft (R) QuickBASIC Compiler Version 4.50

FUNCTION VoltToD2aX (volt)

'Calculates D/A value from a voltage from 0 to 5V
   'Assumes Das16 5V Reference in use
   'Returns Integer between 0 & 4095

DIM x x = volt / 5! * 4096!

IF x < 0 THEN x = 0
   IF x > 4095 THEN x = 4095
   VoltToD2aX = CINT(x)

END FUNCTION

43949 Bytes Available
37723 Bytes Free

0 Warning Error(s)
    0 Severe  Error(s)
```

66

MenuSys.Bas - QBasic PopDown Menu System                                      PAGE   1
                                                                              21 Nov 93
                                                                              14:49:03
                                                    Microsoft (R) QuickBASIC Compiler Version 4.50

'$Title:'MenuSys.Bas - QBasic PopDown Menu System'  $LineSize:112'

' MenuSys.Bas
'
' Skeleton for PopDown Menu System for QBasic
' Video Mode is detected ' Chris McLennan Mar 28/93

'******User Interface
DECLARE FUNCTION CenterStr$ (s$, length AS INTEGER)
DECLARE FUNCTION Exist! (FileName$)
DECLARE FUNCTION FUse$ (x AS SINGLE, wide AS INTEGER, dec AS INTEGER)
DECLARE FUNCTION LPad$ (s$, length AS INTEGER)
DECLARE FUNCTION Max (x AS SINGLE, y AS SINGLE)
DECLARE FUNCTION Min (x AS SINGLE, y AS SINGLE)
DECLARE FUNCTION RPad$ (s$, length AS INTEGER)
DECLARE FUNCTION StrTok$ (Srce$, Delim$)

DECLARE SUB AboutBox ()
DECLARE SUB BoxIt (x1 AS INTEGER, y1 AS INTEGER, x2 AS INTEGER, y2 AS INTEGER)
DECLARE SUB BrList (txt$(), NumLin AS INTEGER)
DECLARE SUB Init ()
DECLARE SUB MainMenu ()
DECLARE SUB MenuBar (Item$(), NumLin AS INTEGER, Choice AS INTEGER, Ky$, x AS INTEGER, Redraw AS INTEGER)
DECLARE SUB MenuExec (cmd AS INTEGER, Done AS INTEGER, RtnCode AS INTEGER)
DECLARE SUB MsgBox (txt$(), NumLin AS INTEGER, Ky$, RestoreScrn AS INTEGER, Pause AS INTEGER)
DECLARE SUB Pop (x1 AS INTEGER, y1 AS INTEGER, x2 AS INTEGER, y2 AS INTEGER)
DECLARE SUB PopUpList (Item$(), NumLin AS INTEGER, Choice AS INTEGER, Ky$, SaveScrn AS INTEGER, Center AS INTEGER)
DECLARE SUB SelectFile (FileName$)
DECLARE SUB SelectNewPath ()
DECLARE SUB UnPop ()

'Graphic Mode Detection
DECLARE SUB GetConfig ()
DECLARE SUB SetConfig (mode AS INTEGER)
DECLARE SUB TestGrModes ()

'VentLib.Bas
DECLARE SUB BrPrnData ()
DECLARE SUB Demo ()
DECLARE SUB LoadVentDatPrn ()
DECLARE SUB InitDas16 ()
DECLARE SUB LoopTest ()
DECLARE SUB LoopTest5 ()
DECLARE SUB LoopTest6 ()
DECLARE SUB OhioFn ()
DECLARE SUB PlotVentDat ()
DECLARE SUB VentLoop ()

MenuSys.Bas - QBasic PopDown Menu System

PAGE 2
21 Nov 93
14:49:03
Microsoft (R) QuickBASIC Compiler Version 4.50

```
'$INCLUDE: 'DasLib.Bi1'
'---------- DasLib.Bi1 ----------

'Das16 Common Area

'Das16 Parameters MUST be in common

CONST A2dBuffSize = 2000

DIM Dio(4) AS INTEGER
    DIM A2dBuff(2000) AS INTEGER
    DIM A2dChNum(2000) AS INTEGER COMMON Dio() AS INTEGER, Md AS INTEGER, Flag AS INTEGER
    COMMON BiPolar AS INTEGER, DasChan AS INTEGER, VoltFS AS SINGLE
    COMMON A2dBuff() AS INTEGER          'Buffer for DasMode4
    COMMON A2dChNum() AS INTEGER         'Buffer for A/D channel info 'for Mode 5 & 6, Quick Basic manages the Data Segment '$DYNAMIC
    'Dynamic Common is dimensioned AFTER the COMMON specification CONST A2dBuf2Size = 2000
    COMMON A2dBuf2() AS INTEGER          'Buffer for A/D data

'$STATIC

'---------- End DasLib.Bi1 ----------

'$INCLUDE: 'MenuSys.Bi1'
'---------- MenuSys.Bi1----------

' Constants for best available screen mode
CONST VGA = 12
CONST MCGA = 13
CONST EGA256 = 9
CONST EGA64 = 8
CONST MONO = 10
CONST HERC = 3
CONST CGA = 1

' User-defined type to hold information about the mode
TYPE Config
    Scrn    AS INTEGER
    Colors  AS INTEGER
    Atribs  AS INTEGER
    XPix    AS INTEGER
    YPix    AS INTEGER
    TCOL    AS INTEGER
    TROW    AS INTEGER
END TYPE
```

MenuSys.Bas - QBasic PopDown Menu System    68                          PAGE   3
                                                                        21 Nov 93
                                                                        14:49:03
                                    Microsoft (R) QuickBASIC Compiler Version 4.50

```
'*****Graphics Modes
COMMON VC AS Config, InitRows AS INTEGER, BestMode AS INTEGER, Available AS STRING '****Menu system
'$DYNAMIC
COMMON PopBuf() AS INTEGER, CurPath$, ForGnd AS INTEGER, Bakgnd AS INTEGER
'$STATIC '---------- End MenuSys.Bi1-----------

'$INCLUDE: 'DasLib.Bi2!'
'---------- DasLib.Bi2 ----------
DIM A2dBuf2(A2dBuf2Size) AS INTEGER
'---------- End DasLib.Bi2 ----------

'$INCLUDE: 'MenuSys.Bi2'
'---------- MenuSys.Bi2-----------
DIM PopBuf(2002, 1) AS INTEGER    'PopUp Buffer
'---------- End MenuSys.Bi2-----------

CONST PgmVersion = 1.09

' Menu Data

MainMenuData:
    DATA "File"
    DATA "Demos"
    DATA ""

PullDownMenuData:
    DATA "About",           1003
    DATA "Select path..",   1002
    DATA "Open..",          1004
    DATA "Import PRN..",    1010
    DATA "Browse Data",     1011
    DATA "Plot Data",       1012
    DATA "Dos Shell",       1001
    DATA "Quit",            1000
    DATA "",-1

DATA "Init",            2000
    DATA "Demo",            2001
    DATA "OhioFn",          2002
    DATA "LoopTest",        2003
    DATA "LoopTest5",       2004
    DATA "LoopTest6",       2005
```

MenuSys.Bas - QBasic PopDown Menu System

```
    DATA "VentLoop",    2006
    DATA "",-1

' Error trap to make screen independent
VideoErr:
  SELECT CASE BestMode    ' Fall through until something works
    CASE VGA
      BestMode = MCGA
      Available = "12BD"
    CASE MCGA
      BestMode = EGA256
      Available = "12789"
    CASE EGA256
      BestMode = CGA
      Available = "12"
    CASE CGA
      BestMode = MONO
      Available = "A"
    CASE MONO
      BestMode = HERC
      Available = "3"
    CASE ELSE
      PRINT "Sorry. Graphics not available. Need MsHerc.Com?"
      END
  END SELECT
  RESUME ' Trap to detect 64K EGA
EGAErr:
  BestMode = EGA64
  Available = "12789"
  RESUME NEXT ' Trap to determine initial number of rows so they can be restored
RowErr:
  IF InitRows = 50 THEN
    InitRows = 43
    RESUME
  ELSE
    InitRows = 25
    RESUME NEXT
  END IF '$Page $SubTitle:'SUB AboutBox'
```

```
MenuSys.Bas - QBasic PopDown Menu System                              PAGE   5
SUB AboutBox                                                          21 Nov 93
                                                                      14:49:03
                                    Microsoft (R) QuickBASIC Compiler Version 4.50

SUB AboutBox
    REDIM a$(9)
    DIM Ky$ a$(0) = "  Status  "
    a$(1) = ""
    a$(2) = "Version - " + LPad$(STR$(PgmVersion), 7)
    a$(3) = ""
    a$(4) = " Memory Available "
    a$(5) = "String - " + LPad$(STR$(FRE("x")), 8)
    a$(6) = "Array  - " + LPad$(STR$(FRE(-1)), 8)
    a$(7) = "Stack  - " + LPad$(STR$(FRE(-2)), 8)
    a$(8) = ""
    a$(9) = "Press any key to continue"

MsgBox a$(), 9, Ky$, -1, -1

ERASE a$
  END SUB

'$Page  $SubTitle:'SUB BoxIt'
```

71

```
MenuSys.Bas - QBasic PopDown Menu System                                    PAGE   6
SUB BoxIt                                                                   21 Nov 93
                                                                            14:49:03
                                          Microsoft (R) QuickBASIC Compiler Version 4.50

SUB BoxIt (x1 AS INTEGER, y1 AS INTEGER, x2 AS INTEGER, y2 AS INTEGER)

DIM Lt$, Hl$, Rt$, Vl$, Lb$, Rb$, top$, mdl$, btm$
  DIM r AS INTEGER, wide AS INTEGER 'Line chars
  Lt$ = "┌": Hl$ = "─": Rt$ = "┐"
  Vl$ = "│"
  Lb$ = "└": Rb$ = "┘"

wide = x2 - x1 + 1 - 2
  top$ = Lt$ + STRING$(wide, Hl$) + Rt$
  mdl$ = Vl$ + STRING$(wide, " ") + Vl$
  btm$ = Lb$ + STRING$(wide, Hl$) + Rb$ FOR r = y1 TO y2
    LOCATE r, x1
    IF r = y1 THEN
      PRINT top$;
    ELSEIF r = y2 THEN
      PRINT btm$;
    ELSE
      PRINT mdl$;
    END IF
  NEXT r
END SUB '$Page $SubTitle:'SUB BrList'
```

72

MenuSys.Bas - QBasic PopDown Menu System
SUB BrList

PAGE 7
21 Nov 93
14:49:03
Microsoft (R) QuickBASIC Compiler Version 4.50

```
SUB BrList (txt$(), NumLin AS INTEGER)

'Browse txt$(NumLin) - press ESC to exit
'txt$(0) is header on line 1

SHARED ForGnd AS INTEGER, BakGnd AS INTEGER

DIM i AS INTEGER, st AS INTEGER, en AS INTEGER
DIM a$

IF NumLin = 0 THEN EXIT SUB        'nothing to do

COLOR ForGnd, BakGnd
CLS

'header on line 1
COLOR BakGnd, ForGnd
LOCATE 1, 1
PRINT txt$(0)

COLOR ForGnd, BakGnd
VIEW PRINT 2 TO 25

'Display list
st = 1
en = Min(CSNG(NumLin), 24)

DO
  'update display
  CLS
  FOR i = st TO en
    LOCATE 2 + (i - st), 1
    PRINT txt$(i);
  NEXT i DO
    a$ = INKEY$
  LOOP UNTIL a$ <> ""

SELECT CASE LEN(a$)
    CASE 1
      IF a$ = CHR$(27) THEN EXIT DO       'ESC to quit CASE 2
      SELECT CASE ASC(MID$(a$, 2, 1))
        CASE 71                           'Home
          st = 1
          en = Min(CSNG(NumLin), 24!)
        CASE 79                           'End
          en = NumLin
          st = Max(CSNG(en - 23), 1!)
        CASE 72                           'Up
          st = Max(CSNG(st - 1), 1!)
          en = Min(CSNG(st + 23), CSNG(NumLin))
```

```
MenuSys.Bas - QBasic PopDown Menu System                                    PAGE    8
SUB BrList                                                                  21 Nov 93
                                                                            14:49:03
                                               Microsoft (R) QuickBASIC Compiler Version 4.50

CASE 80                 'Down
              en = Min(CSNG(en + 1), CSNG(NumLin))
              st = Max(CSNG(en - 23), 1!)
            CASE 73                 'PgUp
              st = Max(CSNG(st - 24), 1!)
              en = Min(CSNG(st + 23), CSNG(NumLin))
            CASE 81                 'PgDn
              en = Min(CSNG(en + 24), CSNG(NumLin))
              st = Max(CSNG(en - 23), 1!)
            CASE 75                 'Left
            CASE 77                 'Right
'           CASE ELSE
'             PRINT ASC(MID$(a$, 2, 1))
          END SELECT

END SELECT

LOOP

VIEW PRINT

END SUB

'$Page $SubTitle:'FUNCTION CenterStr$'
```

MenuSys.Bas - QBasic PopDown Menu System
FUNCTION CenterStr$

PAGE 9
21 Nov 93
14:49:03
Microsoft (R) QuickBASIC Compiler Version 4.50

```
FUNCTION CenterStr$ (s$, length AS INTEGER)

' Adds spaces to start and end of s$, until s$ is length chars

IF (LEN(s$) = length) THEN
    CenterStr$ = s$
  ELSEIF (LEN(s$) > length) THEN
    CenterStr$ = MID$(s$, 1, length)
  ELSE
    DO
      s$ = " " + s$ + " "
    LOOP UNTIL (LEN(s$) >= length)
    IF (LEN(s$) > length) THEN s$ = MID$(s$, 1, length)
    CenterStr$ = s$
  END IF
END FUNCTION '$Page  $SubTitle:'FUNCTION Exist'
```

MenuSys.Bas - QBasic PopDown Menu System
FUNCTION Exist

PAGE 10
21 Nov 93
14:49:03
Microsoft (R) QuickBASIC Compiler Version 4.50

```
FUNCTION Exist (FileName$)

DIM fp AS INTEGER, size AS LONG fp = FREEFILE
  OPEN FileName$ FOR RANDOM AS #fp
  size = LOF(fp)
  CLOSE #fp IF size = 0 THEN           'File doesn't exist
    KILL FileName$
    Exist = 0
  ELSE
    Exist = -1
  END IF

END FUNCTION

'$Page $SubTitle:'FUNCTION FUse$'
```

MenuSys.Bas - QBasic PopDown Menu System
FUNCTION FUse$

```
FUNCTION FUse$ (x AS SINGLE, wide AS INTEGER, dec AS INTEGER)

'Returns X as a string of length wide, with dec digits after decimal

DIM a$
    DIM i AS INTEGER, j AS INTEGER a$ = LTRIM$(STR$(x))

'ensure a decimal point exists
    IF INSTR(a$, ".") = 0 THEN a$ = a$ + "." + STRING$(dec, "0")

'add trailing 0's if necessary
    i = LEN(a$)
    j = INSTR(a$, ".")
    IF (i - j) < dec THEN a$ = a$ + STRING$(dec - (i - j), "0")

'remove trailing 0's if necessary
    i = LEN(a$)
    j = INSTR(a$, ".")
    IF (i - j) > dec THEN a$ = MID$(a$, 1, j + dec)

'pad the correct length
    a$ = LPad$(a$, wide)

FUse$ = a$
END FUNCTION

'$Page $SubTitle:'SUB GetConfig'
```

MenuSys.Bas - QBasic PopDown Menu System
SUB GetConfig

Microsoft (R) QuickBASIC Compiler Version 4.50

```
' ============================ GetConfig ============================
'   Get the starting number of lines and the video adapter.
' ====================================================================
'
SUB GetConfig STATIC SHARED InitRows AS INTEGER, BestMode AS INTEGER, Available AS STRING ' Assume 50 line display and fall through error
   ' until we get the actual number
   InitRows = 50
   ON ERROR GOTO RowErr
   LOCATE InitRows, 1

' Assume best possible screen mode
   BestMode = VGA
   Available = "12789BCD"

ON ERROR GOTO VideoErr
   ' Fall through error trap until a mode works
   SCREEN BestMode
   ' If EGA, then check pages to see whether more than 64K
   ON ERROR GOTO EGAErr
   IF BestMode = EGA256 THEN SCREEN 8, , 1

ON ERROR GOTO 0

' Reset text mode
   SCREEN 0, , 0
   WIDTH 80, 25

END SUB

'$Page $SubTitle:'SUB Init'
```

```
MenuSys.Bas - QBasic PopDown Menu System                                    PAGE  13
SUB Init                                                                  21 Nov 93
                                                                          14:49:03
                                              Microsoft (R) QuickBASIC Compiler Version 4.50

SUB Init
  SHARED CurPath$, ForGnd AS INTEGER, BakGnd AS INTEGER
  DIM fp AS INTEGER, Choice AS INTEGER
  REDIM Men$(2)

'Ask Dos for current Path
  SHELL "CD > Dir.Tmp"

fp = FREEFILE
  OPEN "Dir.Tmp" FOR INPUT AS #fp
    INPUT #fp, CurPath$
  CLOSE #fp
  KILL "Dir.Tmp"

IF RIGHT$(CurPath$, 1) <> "\" THEN CurPath$ = CurPath$ + "\"

'Select colour or monochrome
  Men$(0) = "Select your Monitor"
  Men$(1) = "Colour"
  Men$(2) = "Monochrome"

CLS
  ForGnd = 7
  BakGnd = 0
' LOCATE 10, 31
' PRINT "Select your Monitor"
  DO
    LOCATE 12, 34
      PopUpList Men$(), 2, Choice, Ky$, -1, 0         'pop
  LOOP UNTIL Ky$ = CHR$(13)

CLS
  IF Ky$ = CHR$(13) AND Choice = 1 THEN BakGnd = 1    'colour
  COLOR ForGnd, BakGnd ERASE Men$
END SUB '$Page $SubTitle:'FUNCTION LPad$'
```

MenuSys.Bas - QBasic PopDown Menu System
FUNCTION LPad$

PAGE 14
21 Nov 93
14:49:03
Microsoft (R) QuickBASIC Compiler Version 4.50

```
FUNCTION LPad$ (s$, length AS INTEGER)

' Adds spaces to s$ on left, until s$ is length chars

IF (LEN(s$) = length) THEN
    LPad$ = s$
  ELSEIF (LEN(s$) > length) THEN
    LPad$ = MID$(s$, 1, length)
  ELSE
    DO
      s$ = " " + s$
    LOOP UNTIL (LEN(s$) = length)
    LPad$ = s$
  END IF
END FUNCTION '$Page  $SubTitle:'SUB MainMenu'
```

80

```
MenuSys.Bas - QBasic PopDown Menu System                                    PAGE   15
SUB MainMenu                                                                21 Nov 93
                                                                            14:49:03
                                              Microsoft (R) QuickBASIC Compiler Version 4.50

SUB MainMenu
   SHARED CurPath$, ForGnd AS INTEGER, BakGnd AS INTEGER

DIM I AS INTEGER, Bchoice AS INTEGER, numpickM AS INTEGER
   DIM Done AS INTEGER, tmp AS INTEGER, barX AS INTEGER
   DIM DataSet AS INTEGER, Redraw AS INTEGER, RtnCode AS INTEGER
   DIM numpick AS INTEGER, Choice AS INTEGER
   DIM m$, Mky$, Ky$, CmdLst$ RESTORE MainMenuData        'determine # picks
   numpickM = 0
   DO
      READ m$
      numpickM = numpickM + 1
   LOOP UNTIL m$ = ""
   numpickM = numpickM - 1

REDIM MBar$(numpickM)

RESTORE MainMenuData        'Load the menu data and cmd table
   FOR I = 1 TO numpickM
      READ MBar$(I)
   NEXT I 'Init pull down valid command table
   'enter, esc, left & right arrow
   CmdLst$ = CHR$(13) + CHR$(27) + (CHR$(0) + CHR$(75)) + (CHR$(0) + CHR$(77))

Done = 0
   Redraw = 0

DO
      DO
         MenuBar MBar$(), numpickM, Bchoice, Mky$, barX, Redraw
      LOOP UNTIL Mky$ = CHR$(13)

'count # picks in the selected pull down menu
      RESTORE PullDownMenuData

DataSet = 0

DO WHILE DataSet < Bchoice numpick = 0                'scan group of pull down menu data
         DO
            READ m$, tmp
            numpick = numpick + 1
         LOOP UNTIL tmp = -1 numpick = numpick - 1      'correct # items in group
         DataSet = DataSet + 1      'correct ptr to pull down group
      LOOP REDIM Menu$(numpick), cmd(numpick) AS INTEGER       'allocate memory
```

MenuSys.Bas - QBasic PopDown Menu System
SUB MainMenu

PAGE 16
21 Nov 93
14:49:03
Microsoft (R) QuickBASIC Compiler Version 4.50

```
'Load the selected pull down menu

RESTORE PullDownMenuData

DataSet = 0

'scan group of pull down menu data, until at start of desired one
DO UNTIL DataSet = Bchoice - 1
   DO
      READ m$, tmp
   LOOP UNTIL tmp = -1

DataSet = DataSet + 1     'correct ptr to pull down group

LOOP

FOR i = 1 TO numpick          'load pull down data
   READ Menu$(i), cmd(i)
NEXT i VIEW PRINT 2 TO 25            'clear screen under menu bar
COLOR ForGnd, 0
CLS 2
COLOR ForGnd, BakGnd
VIEW PRINT DO
   LOCATE 2, barX
   PopUpList Menu$(), numpick, Choice, Ky$, 0, 0      'no pop, no center
LOOP UNTIL INSTR(CmdLst$, Ky$) > 0

SELECT CASE Ky$

CASE CHR$(0) + CHR$(77)    'right arrow
      Bchoice = Bchoice + 1
      IF Bchoice > numpickM THEN Bchoice = 1
      Redraw = -1      'unpop pulldown & move to adjacent pull down CASE CHR$(0) + CHR$(75)    'left arrow
      Bchoice = Bchoice - 1
      IF Bchoice < 1 THEN Bchoice = numpickM
      Redraw = -1      'unpop pulldown & move to adjacent pull down CASE CHR$(27)              'ESC
      Redraw = 0

CASE CHR$(13)              'Enter
      MenuExec cmd(Choice), Done, RtnCode
      Redraw = -1
END SELECT LOOP UNTIL Done
```

```
MenuSys.Bas - QBasic PopDown Menu System                                          PAGE  17
SUB MainMenu                                                                     21 Nov 93
                                                                                 14:49:03
                                                    Microsoft (R) QuickBASIC Compiler Version 4.50

ERASE Menu$, cmd         'deallocate pull down data
    ERASE MBar$
END SUB

'$Page $SubTitle:'FUNCTION Max'
```

```
MenuSys.Bas - QBasic PopDown Menu System                              PAGE  18
FUNCTION Max                                                          21 Nov 93
                                                                      14:49:03
                                       Microsoft (R) QuickBASIC Compiler Version 4.50

FUNCTION Max (x AS SINGLE, y AS SINGLE)
   IF x > y THEN
      Max = x
   ELSE
      Max = y
   END IF
END FUNCTION

'$Page  $SubTitle:'SUB MenuBar'
```

MenuSys.Bas - QBasic PopDown Menu System  PAGE 19
SUB MenuBar                                21 Nov 93
                                           14:49:03
                    Microsoft (R) QuickBASIC Compiler Version 4.50

```
SUB MenuBar (Item$(), NumLin AS INTEGER, Choice AS INTEGER, Ky$, x AS INTEGER, Redraw AS INTEGE
R)

' Horizontal Menu Bar
' Selected by down arrow or enter
' if Redraw true, the menu bar is only updated
' Item$(0) is ignored SHARED ForGnd AS INTEGER, BakGnd AS INTEGER DIM maxLen AS INTEGER, i AS INTEGER
  DIM hot AS INTEGER, oldhot AS INTEGER, Done AS INTEGER
  DIM mask$, cmd$, CmdTbl$ maxLen = 0
  FOR i = 1 TO NumLin       'get max width
    IF LEN(Item$(i)) > maxLen THEN maxLen = LEN(Item$(i))
  NEXT i
  IF maxLen + NumLin * 2 > 80 THEN STOP 'generate table for column positions for each pick REDIM whereX(NumLin) AS INTEGER whereX(1) = 1
  FOR i = 2 TO NumLin
    whereX(i) = whereX(i - 1) + LEN(Item$(i - 1)) + 2
  NEXT i VIEW PRINT 1 TO 1
  COLOR BakGnd, ForGnd
  CLS 2

'init command table for 1st letter in Item$
  CmdTbl$ = ""
  FOR i = 1 TO NumLin
    CmdTbl$ = CmdTbl$ + UCASE$(LEFT$(Item$(i), 1))
  NEXT i
  CmdTbl$ = CmdTbl$ + CmdTbl$          'double list to wrap around IF Choice >= 1 AND Choice <= NumLin THEN
    hot = Choice
  ELSE
    hot = 1
  END IF
  oldhot = hot 'Draw MenuBar
  FOR i = 1 TO NumLin
    LOCATE 1, whereX(i)
    mask$ = "\" + STRING$(LEN(Item$(i)), " ") + "\"
    IF i = hot THEN COLOR ForGnd, BakGnd
    PRINT USING mask$; " " + Item$(i) + " ";
    IF i = hot THEN COLOR BakGnd, ForGnd
```

MenuSys.Bas - QBasic PopDown Menu System
SUB MenuBar

PAGE 20
21 Nov 93
14:49:03
Microsoft (R) QuickBASIC Compiler Version 4.50

```
    NEXT i

'if Redraw, were done
    IF Redraw THEN
       Ky$ = CHR$(13)
       x = whereX(hot)
       VIEW PRINT
       ERASE whereX
       EXIT SUB
    END IF Done = 0

DO
       IF hot <> oldhot THEN              'update menu bar

'deselect oldhot
          LOCATE 1, whereX(oldhot)
          mask$ = "\" + STRING$(LEN(Item$(oldhot)), " ") + "\"
          PRINT USING mask$; " " + Item$(oldhot) + " ";

'select hot
          LOCATE 1, whereX(hot)
          mask$ = "\" + STRING$(LEN(Item$(hot)), " ") + "\"
          COLOR ForGnd, BakGnd
          PRINT USING mask$; " " + Item$(hot) + " ";
          COLOR BakGnd, ForGnd
       END IF Choice = hot
       oldhot = hot DO
          cmd$ = UCASE$(INKEY$)
       LOOP UNTIL cmd$ <> ""

SELECT CASE LEN(cmd$)

CASE 1             'one char
             Ky$ = cmd$         'save key pressed, to return it
             SELECT CASE ASC(cmd$)
                CASE 27          'Esc
                   Done = -1
                CASE 13          'Enter
                   Done = -1
                CASE ELSE            '1st letter of command?
                   i = INSTR(hot - 1 + 2, CmdTbl$, UCASE$(cmd$))
                   IF i > 0 THEN
                      hot = (i - 1) + 1
                      IF hot > NumLin THEN hot = hot - NumLin
                   END IF
             END SELECT CASE 2             'extended char
```

```
MenuSys.Bas - QBasic PopDown Menu System                                           PAGE  21
SUB MenuBar                                                                        21 Nov 93
                                                                                   14:49:03
                                                    Microsoft (R) QuickBASIC Compiler Version 4.50

SELECT CASE ASC(MID$(cmd$, 2, 1))
          CASE 71         'home
            hot = 1
          CASE 79         'end
            hot = NumLin
          CASE 80         'dn
            Ky$ = CHR$(13)        'dn = enter
            Done = -1
          CASE 77         'right
            hot = hot + 1
            IF hot > NumLin THEN hot = 1
          CASE 75         'left
            hot = hot - 1
            IF hot < 1 THEN hot = NumLin
        END SELECT
    END SELECT LOOP UNTIL Done 'return left x position of item selected on menu bar
  x = whereX(hot)

VIEW PRINT

ERASE whereX
END SUB

'$Page $SubTitle:'SUB MenuExec'
```

```
MenuSys.Bas - QBasic PopDown Menu System                                    PAGE 22
SUB MenuExec                                                                21 Nov 93
                                                                            14:49:03
                                          Microsoft (R) QuickBASIC Compiler Version 4.50

SUB MenuExec (cmd AS INTEGER, Done AS INTEGER, RtnCode AS INTEGER) STATIC

' cmd       = command to execute
' done      = if set to -1, causes menu to terminate program
' RtnCode   = error return of command (-1 if fail)

SHARED CurPath$, ForGnd AS INTEGER, BakGnd AS INTEGER
   DIM FileName$

SELECT CASE cmd

CASE 1000                      'quit
         Done = -1

CASE 1001                      'shell
         COLOR 7, 0
         CLS
         PRINT "Type Exit to return to program"
         SHELL
         CLS
         COLOR ForGnd, BakGnd CASE 1002                      'new path
         SelectNewPath CASE 1003                      'about
         AboutBox CASE 1004                      'Open
         SelectFile FileName$ CASE 1010                      'Import PRN..
         LoadVentDatPrn CASE 1011                      'Browse Data
         BrPrnData CASE 1012                      'Plot Data
         PlotVentDat CASE 2000
         InitDas16                   'Init Das16

CASE 2001                      'Demo of Acquisition primatives
         Demo

CASE 2002                      'Demo of Ohio Control Regression Analysis
         OhioFn CASE 2003                      'Slow LoopTest
         LoopTest CASE 2004                      'Medium speed LoopTest
         LoopTest5
```

```
MenuSys.Bas - QBasic PopDown Menu System                              PAGE  23
SUB MenuExec                                                          21 Nov 93
                                                                      14:49:03
                                           Microsoft (R) QuickBASIC Compiler Version 4.50

CASE 2005                  'High Speed LoopTest
            LoopTest6

CASE 2006                  'Interrupt LoopTest
            VentLoop

END SELECT

END SUB

'$Page  $SubTitle:'FUNCTION Min'
```

MenuSys.Bas - QBasic PopDown Menu System
FUNCTION Min

PAGE 24
21 Nov 93
14:49:03
Microsoft (R) QuickBASIC Compiler Version 4.50

```
FUNCTION Min (x AS SINGLE, y AS SINGLE)
  IF x < y THEN
    Min = x
  ELSE
    Min = y
  END IF
END FUNCTION

'$Page $SubTitle:'SUB MsgBox'
```

```
MenuSys.Bas - QBasic PopDown Menu System                      PAGE 25
SUB MsgBox                                                    21 Nov 93
                                                              14:49:03
                              Microsoft (R) QuickBASIC Compiler Version 4.50

SUB MsgBox (txt$(), NumLin AS INTEGER, Ky$, RestoreScrn AS INTEGER, Pause AS INTEGER)

' If RestoreScrn NOT true, user must call UnPop
' If Pause true, inkey$ returns Ky$
' Title of box in Txt$(0)

SHARED CurPath$, ForGnd AS INTEGER, BakGnd AS INTEGER
  DIM x1 AS INTEGER, y1 AS INTEGER, x2 AS INTEGER, y2 AS INTEGER
  DIM i AS INTEGER, maxLen AS INTEGER 'calcute area of centered box
  maxLen = 0
  FOR i = 0 TO NumLin
    IF LEN(txt$(i)) > maxLen THEN maxLen = LEN(txt$(i))
  NEXT i
  IF maxLen > 78 THEN maxLen = 78 x1 = 41 - (maxLen + 2) \ 2
  x2 = x1 + maxLen + 1
  y1 = 12 - (NumLin + 2) \ 2
  y2 = y1 + (NumLin + 1)

Pop x1, y1, x2, y2
  BoxIt x1, y1, x2, y2

'Title - Txt$(0) not blank
  IF txt$(0) <> "" THEN
    LOCATE y1, (x1 + (x2 - x1 + 1) \ 2) - LEN(txt$(0)) \ 2
    PRINT txt$(0);
  END IF FOR i = 1 TO NumLin
    LOCATE y1 + i, x1 + 1
    PRINT CenterStr$(txt$(i), maxLen);
  NEXT i IF Pause THEN
    DO
      Ky$ = UCASE$(INKEY$)
    LOOP UNTIL Ky$ <> ""
  END IF IF RestoreScrn THEN UnPop
END SUB '$Page $SubTitle:'SUB Pop'
```

MenuSys.Bas - QBasic PopDown Menu System                                PAGE 26
SUB Pop                                                                 21 Nov 93
                                                                        14:49:03
                                        Microsoft (R) QuickBASIC Compiler Version 4.50

```
SUB Pop (x1 AS INTEGER, y1 AS INTEGER, x2 AS INTEGER, y2 AS INTEGER)

SHARED PopBuf() AS INTEGER
  DIM r AS INTEGER, c AS INTEGER, i AS INTEGER

PopBuf(1, 0) = x1
  PopBuf(1, 1) = y1
  PopBuf(2, 0) = x2
  PopBuf(2, 1) = y2
  i = 3
  FOR r = y1 TO y2
    FOR c = x1 TO x2
      PopBuf(i, 0) = SCREEN(r, c, 0)
      PopBuf(i, 1) = SCREEN(r, c, 1)
      i = i + 1
    NEXT c
  NEXT r
END SUB

'$Page $SubTitle:'SUB PopUpList'
```

MenuSys.Bas - QBasic PopDown Menu System
SUB PopUpList

Microsoft (R) QuickBASIC Compiler Version 4.50

```
SUB PopUpList (Items(), NumLin AS INTEGER, Choice AS INTEGER, Ky$, SaveScrn AS INTEGER, Center
AS INTEGER)

' If SaveScrn TRUE, screen is popped/unpopped
' If Center TRUE, LIST is centered
' Left & Right arrow exit, with Ky$ set to [0 75], [0 77] respectivly
' If Choice in range, list is scrolled to selected item SHARED ForGnd AS INTEGER, BakGnd AS INTEGER DIM whereX AS INTEGER, whereY AS INTEGER, maxLen AS INTEGER, i AS INTEGER
DIM x1 AS INTEGER, y1 AS INTEGER, x2 AS INTEGER
DIM y2 AS INTEGER, po AS INTEGER, pe AS INTEGER, hot AS INTEGER
DIM oldhot AS INTEGER, Done AS INTEGER, scroll AS INTEGER
DIM mask$, CmdTbl$ maxLen = 0
whereY = CSRLIN        'save x,y position @ calling
whereX = POS(1)

FOR i = 0 TO NumLin    'get max width
  IF LEN(Items(i)) > maxLen THEN maxLen = LEN(Items(i))
NEXT i
IF maxLen > 78 THEN STOP 'choose popup area
IF NOT Center THEN
  y1 = whereY
  IF whereY + NumLin + 1 > 24 THEN    'determine lower screen limits
    y2 = 24
  ELSE
    y2 = whereY + NumLin + 1
  END IF x1 = whereX                    'cal popup hort region
  x2 = whereX + maxLen + 1
  IF x2 > 80 THEN                'force col 80 = right edge
    x2 = 80
    x1 = 80 - maxLen - 1
  END IF ELSE                             'Center popup
  x1 = 40 - (maxLen + 2) \ 2
  x2 = x1 + maxLen + 1
  y1 = 12 - (NumLin + 2) \ 2
  IF y1 < 2 THEN y1 = 2
  y2 = y1 + (NumLin - 1 + 2)
  IF y2 > 24 THEN y2 = 24
END IF COLOR ForGnd, BakGnd
IF SaveScrn THEN Pop x1, y1, x2, y2    'save region on screen
BoxIt x1, y1, x2, y2                   'box it
```

93

MenuSys.Bas - QBasic PopDown Menu System
SUB PopUpList

```
'Title - if not blank
IF Item$(0) <> "" THEN
    LOCATE y1, (x1 + (x2 - x1 + 1) \ 2) - LEN(Item$(0)) \ 2
    PRINT Item$(0);
END IF mask$ = "\" + STRING$(maxLen - 2, " ") + "\"

ps = 1
pe = ps + (y2 - y1 - 2)

'if value of Choice called with is in range - use it
IF Choice >= ps AND Choice <= NumLin THEN
    hot = Choice
    DO WHILE hot > pe
        ps = ps + 1
        pe = pe + 1
    LOOP
ELSE
    hot = ps
END IF oldhot = hot
Done = 0
scroll = 0

'init command table for 1st letter in Item$
CmdTbl$ = ""
FOR i = 1 TO NumLin
    CmdTbl$ = CmdTbl$ + UCASE$(LEFT$(Item$(i), 1))
NEXT i
CmdTbl$ = CmdTbl$ + CmdTbl$            'double list to wrap around FOR i = ps TO pe                        'draw list
    LOCATE y1 + 1 + i - ps, x1 + 1
    IF i = hot THEN COLOR BakGnd, ForGnd
    PRINT USING mask$; Item$(i);
    IF i = hot THEN COLOR ForGnd, BakGnd
NEXT i DO
    'Display picks
    IF hot >= ps AND hot <= pe THEN             'pick on screen
        LOCATE y1 + 1 + oldhot - ps, x1 + 1
        PRINT USING mask$; Item$(oldhot);        'deselect old LOCATE y1 + 1 + hot - ps, x1 + 1         'select new
        COLOR BakGnd, ForGnd
        PRINT USING mask$; Item$(hot);
        COLOR ForGnd, BakGnd ELSE                                         'scroll or moved by 1 line IF scroll THEN                           'scroll list
```

```
MenuSys.Bas - QBasic PopDown Menu System                                          PAGE  29
SUB PopUpList                                                                    21 Nov 93
                                                                                 14:49:03
                                                    Microsoft (R) QuickBASIC Compiler Version 4.50 scroll = 0
        IF hot < ps THEN                          'scroll up
            ps = ps - (y2 - y1 - 1)
            IF ps < 1 THEN ps = 1
            pe = ps + (y2 - y1 - 2)

ELSE                                      'scroll down
            pe = pe + (y2 - y1 - 1)
            IF pe > NumLin THEN pe = NumLin
            ps = pe - (y2 - y1 - 2)
        END IF ELSEIF hot < ps THEN                          'scroll up 1
        ps = hot
        pe = ps + (y2 - y1 - 2)

ELSE                                          'scroll down 1
        pe = hot
        ps = pe - (y2 - y1 - 2)
        IF ps < 1 THEN
            ps = 1
            pe = ps + (y2 - y1 - 2)
        END IF

END IF

FOR i = ps TO pe                              'draw list
        LOCATE y1 + 1 + i - ps, x1 + 1
        IF i = hot THEN COLOR BakGnd, ForGnd
        PRINT USING mask$; Items$(i);
        IF i = hot THEN COLOR ForGnd, BakGnd
    NEXT i

END IF

Choice = hot
oldhot = hot

DO
    cmd$ = UCASE$(INKEY$)
LOOP UNTIL cmd$ <> ""

SELECT CASE LEN(cmd$)

CASE 1                'one char
        Ky$ = cmd$        'save key pressed, to return it
        SELECT CASE ASC(cmd$)
            CASE 27       'Esc
                Done = -1
            CASE 13       'Enter
                Done = -1
            CASE ELSE             '1st letter of command?
                i = INSTR(hot - 1 + 2, CmdTbl$, UCASE$(cmd$))
                IF i > 0 THEN
```

MenuSys.Bas - QBasic PopDown Menu System
SUB PopUpList

PAGE 30
21 Nov 93
14:49:03
Microsoft (R) QuickBASIC Compiler Version 4.50

```
              hot = (i - 1) + 1
              IF hot > NumLin THEN hot = hot - NumLin
            END IF
        END SELECT CASE 2             'extended char
          SELECT CASE ASC(MID$(cmd$, 2, 1))
            CASE 71        'home
              hot = 1
            CASE 79        'end
              hot = NumLin
            CASE 73        'pg up
              hot = hot - (y2 - y1 - 1)
              IF hot < 1 THEN hot = 1
              scroll = -1
            CASE 81        'pg dn
              hot = hot + (y2 - y1 - 1)
              IF hot > NumLin THEN hot = NumLin
              scroll = -1
            CASE 72        'up
              hot = hot - 1
              IF hot < 1 THEN hot = NumLin
            CASE 80        'dn
              hot = hot + 1
              IF hot > NumLin THEN hot = 1
            CASE 77        'right
              Ky$ = cmd$
              Done = -1
            CASE 75        'left
              Ky$ = cmd$
              Done = -1
          END SELECT
      END SELECT LOOP UNTIL Done IF SaveScrn THEN UnPop

END SUB

'$Page $SubTitle:'FUNCTION RPad$'
```

MenuSys.Bas - QBasic PopDown Menu System
FUNCTION RPad$

PAGE 31
21 Nov 93
14:49:03
Microsoft (R) QuickBASIC Compiler Version 4.50

```
FUNCTION RPad$ (s$, length AS INTEGER)

' Adds spaces to s$ on right, until s$ is length chars

IF (LEN(s$) = length) THEN
    RPad$ = s$
  ELSEIF (LEN(s$) > length) THEN
    RPad$ = MID$(s$, 1, length)
  ELSE
    DO
      s$ = s$ + " "
    LOOP UNTIL (LEN(s$) = length)
    RPad$ = s$
  END IF
END FUNCTION '$Page $SubTitle:'SUB SelectFile'
```

```
MenuSys.Bas - QBasic PopDown Menu System                              PAGE  32
SUB SelectFile                                                        21 Nov 93
                                                                      14:49:03
                                              Microsoft (R) QuickBASIC Compiler Version 4.50

SUB SelectFile (FileName$)

SHARED CurPath$, ForGnd AS INTEGER, BakGnd AS INTEGER

DIM fp AS INTEGER, nfil AS INTEGER, Choice AS INTEGER, size AS LONG
  DIM FilSpec$, Ky$ FileName$ = ""

REDIM Msg$(3)
  Msg$(0) = "Select File"
  Msg$(1) = ""
  Msg$(2) = "Scanning " + CurPath$
  Msg$(3) = ""

MsgBox Msg$(), 3, Ky$, 0, 0      'no unpop, no pause
  ERASE Msg$

SHELL "Dir " + CurPath$ + "*.*  /ON /A-D /B > Dir.Tmp"

fp = FREEFILE
  OPEN "Dir.Tmp" FOR RANDOM AS #fp LEN = 1
  size = LOF(fp)
  CLOSE #fp IF size = 0 THEN
    UnPop                          'remove MsgBox message REDIM Msg$(7)
    Msg$(0) = "Select File"
    Msg$(1) = ""
    Msg$(2) = "---- WARNING ----"
    Msg$(3) = ""
    Msg$(4) = CurPath$
    Msg$(5) = "contained NO files"
    Msg$(6) = ""
    Msg$(7) = "Press any key to continue"

MsgBox Msg$(), 7, Ky$, -1, -1   'unpop, pause
    ERASE Msg$

KILL "Dir.Tmp"
    EXIT SUB
  END IF nfil = 0
  OPEN "Dir.Tmp" FOR INPUT AS #fp
  WHILE NOT EOF(fp)
    LINE INPUT #fp, FilSpec$
    FilSpec$ = LTRIM$(RTRIM$(FilSpec$))
    IF LEN(FilSpec$) > 0 AND FilSpec$ <> "DIR.TMP" THEN nfil = nfil + 1
  WEND
  CLOSE #fp
```

98

```
MenuSys.Bas - QBasic PopDown Menu System                              PAGE 33
SUB SelectFile                                                      21 Nov 93
                                                                     14:49:03
                                            Microsoft (R) QuickBASIC Compiler Version 4.50

IF nfil = 0 THEN
     UnPop                          'remove MsgBox message

REDIM Msg$(7)
     Msg$(0) = "Select File"
     Msg$(1) = ""
     Msg$(2) = "---- WARNING ----"
     Msg$(3) = ""
     Msg$(4) = CurPath$
     Msg$(5) = "contained NO files"
     Msg$(6) = ""
     Msg$(7) = "Press any key to continue"

MsgBox Msg$(), 7, Ky$, -1, -1    'unpop, pause
     ERASE Msg$

KILL "Dir.Tmp"
     EXIT SUB
   END IF

REDIM Fil$(nfil)

fp = FREEFILE
   OPEN "Dir.Tmp" FOR INPUT AS #fp
   nfil = 1
   WHILE NOT EOF(fp)
     LINE INPUT #fp, Fil$(nfil)
     Fil$(nfil) = LTRIM$(RTRIM$(Fil$(nfil)))
     IF LEN(Fil$(nfil)) > 0 AND Fil$(nfil) <> "DIR.TMP" THEN nfil = nfil + 1
   WEND
   nfil = nfil - 1
   CLOSE #fp KILL "Dir.Tmp"

UnPop                             'remove MsgBox message

Fil$(0) = CurPath$ + "*.*"
   DO
     PopUpList Fil$(), nfil, Choice, Ky$, -1, -1    'pop, center
   LOOP UNTIL Ky$ = CHR$(13) OR Ky$ = CHR$(27)

IF Ky$ = CHR$(13) THEN FileName$ = Fil$(Choice)

ERASE Fil$

END SUB

'$Page $SubTitle:'SUB SelectNewPath'
```

99

MenuSys.Bas - QBasic PopDown Menu System
SUB SelectNewPath

PAGE 34
21 Nov 93
14:49:03
Microsoft (R) QuickBASIC Compiler Version 4.50

```
SUB SelectNewPath

SHARED CurPath$, ForGnd AS INTEGER, BakGnd AS INTEGER

DIM fp AS INTEGER, ndir AS INTEGER, Choice AS INTEGER
  DIM Drv$, DirSpec$, Ky$

REDIM Msg$(4)
  Msg$(0) = "Select New Path"
  Msg$(1) = ""
  Msg$(2) = "Current Path: " + CurPath$
  Msg$(3) = ""
  Msg$(4) = "Drive to Scan [A..Z, ESC] = "

DO
    MsgBox Msg$(), 4, Drv$, -1, -1
  LOOP UNTIL INSTR("ABCDEFGHIJKLMNOPQRSTUVWXYZ" + CHR$(13) + CHR$(27), Drv$) > 0
  ERASE Msg$

IF Drv$ = CHR$(13) THEN
    Drv$ = LEFT$(CurPath$, 1)
  ELSEIF Drv$ = CHR$(27) THEN
    EXIT SUB
  END IF REDIM Msg$(3)
  Msg$(0) = "Select New Path"
  Msg$(1) = ""
  Msg$(2) = "Scanning Directory on " + Drv$ + ":"
  Msg$(3) = ""

MsgBox Msg$(), 3, Ky$, 0, 0      'no unpop, no pause
  ERASE Msg$

SHELL "Dir " + Drv$ + ":\ /AD /S /B | Sort > Dir.Tmp"
  fp = FREEFILE
  ndir = 1
  OPEN "Dir.Tmp" FOR INPUT AS #fp
  WHILE NOT EOF(fp)
    LINE INPUT #fp, DirSpec$
    ndir = ndir + 1
  WEND
  CLOSE #fp IF ndir = 2 AND LEN(DirSpec$) = 0 THEN      'Drive had no sub-dirs
    ndir = 1
  END IF REDIM Fdir$(ndir)

Fdir$(1) = Drv$ + ":\"         'Root Dir

IF ndir > 1 THEN
    fp = FREEFILE
```

```
MenuSys.Bas - QBasic PopDown Menu System                            PAGE  35
SUB SelectNewPath                                                   21 Nov 93
                                                                    14:49:03
                                        Microsoft (R) QuickBASIC Compiler Version 4.50

OPEN "Dir.Tmp" FOR INPUT AS #fp
      ndir = 2
      WHILE NOT EOF(fp)
        LINE INPUT #fp, Fdir$(ndir)
        ndir = ndir + 1
      WEND
      ndir = ndir - 1
      CLOSE #fp
   END IF KILL "Dir.Tmp"

UnPop                         'remove MsgBox message

IF ndir = 1 THEN
      REDIM Msg$(6)
      Msg$(0) = "Select New Path"
      Msg$(1) = ""
      Msg$(2) = "---- WARNING ----"
      Msg$(3) = ""
      Msg$(4) = Drv$ + ": had NO directories"
      Msg$(5) = ""
      Msg$(6) = "Press any key to continue"

MsgBox Msg$(), 6, Ky$, -1, -1    'unpop, pause
      ERASE Msg$
   END IF

Fdir$(0) = "Select New Path"
   DO
      PopUpList Fdir$(), ndir, Choice, Ky$, -1, -1     'pop, center
   LOOP UNTIL Ky$ = CHR$(13) OR Ky$ = CHR$(27)

IF Ky$ = CHR$(13) THEN
      CurPath$ = Fdir$(Choice)
      IF RIGHT$(CurPath$, 1) <> "\" THEN CurPath$ = CurPath$ + "\"
   END IF ERASE Fdir$
END SUB '$Page $SubTitle:'SUB SetConfig'
```

MenuSys.Bas - QBasic PopDown Menu System  
SUB SetConfig

PAGE 36  
21 Nov 93  
14:49:03  
Microsoft (R) QuickBASIC Compiler Version 4.50

```
' =========================== SetConfig ===========================
'   Sets the correct values for each field of the VC variable. They
'   vary depending on Mode and on the current configuration.
' =================================================================
'
SUB SetConfig (mode AS INTEGER) STATIC SHARED VC AS Config, BestMode AS INTEGER SELECT CASE mode
        CASE 1    ' Four-color graphics for CGA, EGA, VGA, and MCGA
            IF BestMode = CGA OR BestMode = MCGA THEN
                VC.Colors = 0
            ELSE
                VC.Colors = 16
            END IF
            VC.Atribs = 4
            VC.XPix = 319
            VC.YPix = 199
            VC.TCOL = 40
            VC.TROW = 25
        CASE 2    ' Two-color medium-res graphics for CGA, EGA, VGA, and MCGA
            IF BestMode = CGA OR BestMode = MCGA THEN
                VC.Colors = 0
            ELSE
                VC.Colors = 16
            END IF
            VC.Atribs = 2
            VC.XPix = 639
            VC.YPix = 199
            VC.TCOL = 80
            VC.TROW = 25
        CASE 3    ' Two-color high-res graphics for Hercules
            VC.Colors = 0
            VC.Atribs = 2
            VC.XPix = 719
            VC.YPix = 347
            VC.TCOL = 80
            VC.TROW = 25
        CASE 7    ' 16-color medium-res graphics for EGA and VGA
            VC.Colors = 16
            VC.Atribs = 16
            VC.XPix = 319
            VC.YPix = 199
            VC.TCOL = 40
            VC.TROW = 25
        CASE 8    ' 16-color high-res graphics for EGA and VGA
            VC.Colors = 16
            VC.Atribs = 16
            VC.XPix = 639
            VC.YPix = 199
            VC.TCOL = 80
            VC.TROW = 25
        CASE 9    ' 16- or 4-color very high-res graphics for EGA and VGA
```

```
MenuSys.Bas - QBasic PopDown Menu System                                PAGE  37
SUB SetConfig                                                           21 Nov 93
                                                                        14:49:03
                                        Microsoft (R) QuickBASIC Compiler Version 4.50

VC.Colors = 64
            IF BestMode = EGA64 THEN VC.Atribs = 4 ELSE VC.Atribs = 16
            VC.XPix = 639
            VC.YPix = 349
            VC.TCOL = 80
            VC.TROW = 25
        CASE 10   ' Two-color high-res graphics for EGA or VGA monochrome
            VC.Colors = 0
            VC.Atribs = 2
            VC.XPix = 319
            VC.YPix = 199
            VC.TCOL = 80
            VC.TROW = 25
        CASE 11   ' Two-color very high-res graphics for VGA and MCGA
            ' Note that for VGA screens 11, 12, and 13, more colors are
            ' available, depending on how the colors are mixed.
            VC.Colors = 216
            VC.Atribs = 2
            VC.XPix = 639
            VC.YPix = 479
            VC.TCOL = 80
            VC.TROW = 30
        CASE 12   ' 16-color very high-res graphics for VGA
            VC.Colors = 216
            VC.Atribs = 16
            VC.XPix = 639
            VC.YPix = 479
            VC.TCOL = 80
            VC.TROW = 30
        CASE 13   ' 256-color medium-res graphics for VGA and MCGA
            VC.Colors = 216
            VC.Atribs = 256
            VC.XPix = 639
            VC.YPix = 479
            VC.TCOL = 40
            VC.TROW = 25
        CASE ELSE
            VC.Colors = 16
            VC.Atribs = 16
            VC.XPix = 0
            VC.YPix = 0
            VC.TCOL = 80
            VC.TROW = 25
            VC.Scrn = 0
            EXIT SUB
    END SELECT
    VC.Scrn = mode

END SUB

FUNCTION StrTok$ (Srce$, Delim$)
STATIC Start%, SaveStr$

' If first call, make a copy of the string.
```

MenuSys.Bas - QBasic PopDown Menu System
SUB SetConfig

```
    IF Srce$ <> "" THEN
        Start% = 1: SaveStr$ = Srce$
    END IF

BegPos% = Start%: Ln% = LEN(SaveStr$)
    ' Look for start of a token (character that isn't delimiter).
    WHILE BegPos% <= Ln% AND INSTR(Delim$, MID$(SaveStr$, BegPos%, 1)) <> 0
        BegPos% = BegPos% + 1
    WEND
    ' Test for token start found.
    IF BegPos% > Ln% THEN
        StrTok$ = "": EXIT FUNCTION
    END IF
    ' Find the end of the token.
    EndPos% = BegPos%
    WHILE EndPos% <= Ln% AND INSTR(Delim$, MID$(SaveStr$, EndPos%, 1)) = 0
        EndPos% = EndPos% + 1
    WEND
    StrTok$ = MID$(SaveStr$, BegPos%, EndPos% - BegPos%)
    ' Set starting point for search for next token.
    Start% = EndPos%

END FUNCTION

'$Page  $SubTitle:'SUB TestGrModes'
```

MenuSys.Bas - QBasic PopDown Menu System
SUB TestGrModes

Microsoft (R) QuickBASIC Compiler Version 4.50

```
SUB TestGrModes

SHARED VC AS Config, InitRows AS INTEGER, BestMode AS INTEGER, Available AS STRING DIM i AS INTEGER, mode AS INTEGER, a$ 'test all modes
  FOR i = 1 TO LEN(Available)

a$ = MID$(Available, i, 1)

IF a$ >= "1" AND a$ <= "9" THEN
      mode = VAL(a$)
    ELSE
      mode = (ASC(a$) - ASC("A") + 1) + 9
    END IF SetConfig mode SCREEN VC.Scrn
    PRINT "Vc.Scrn";   VC.Scrn
    PRINT "Vc.Colors"; VC.Colors
    PRINT "Vc.Atribs"; VC.Atribs
    PRINT "Vc.XPix";   VC.XPix
    PRINT "Vc.YPix";   VC.YPix
    PRINT "Vc.TCOL";   VC.TCOL
    PRINT "Vc.TROW";   VC.TROW
    PRINT "InitRows";  InitRows
    PRINT "BestMode";  BestMode
    PRINT "Available"; Available
    INPUT a$ SCREEN 0
    WIDTH 80, InitRows
  NEXT i
END SUB '$Page $SubTitle:'SUB UnPop'
```

MenuSys.Bas - QBasic PopDown Menu System
SUB UnPop

PAGE 40
21 Nov 93
14:49:03
Microsoft (R) QuickBASIC Compiler Version 4.50

```
SUB UnPop

SHARED PopBuf() AS INTEGER, ForGnd AS INTEGER, BakGnd AS INTEGER
  DIM r AS INTEGER, c AS INTEGER, i AS INTEGER i = 3
  FOR r = PopBuf(1, 1) TO PopBuf(2, 1)
    FOR c = PopBuf(1, 0) TO PopBuf(2, 0)
      LOCATE r, c
      COLOR (PopBuf(i, 1) AND &HF), (PopBuf(i, 1) AND &HF0) \ 16
      PRINT CHR$(PopBuf(i, 0));
      i = i + 1
    NEXT c
  NEXT r

COLOR ForGnd, BakGnd
END SUB
```

43949 Bytes Available
26833 Bytes Free

0 Warning Error(s)
   0 Severe  Error(s)

106

VentLib.Bas - Ohio 7000 Ventilator Control                                    PAGE   1
                                                                              21 Nov 93
                                                                              14:49:11
                                              Microsoft (R) QuickBASIC Compiler Version 4.50

'$Title:'VentLib.Bas - Ohio 7000 Ventilator Control' $LineSize:112'

'VentLib
'Oct 2/93
'Chris McLennan

'MenuSys.Bas
DECLARE FUNCTION FUse$ (x AS SINGLE, wide AS INTEGER, dec AS INTEGER)
DECLARE FUNCTION LPad$ (s$, length AS INTEGER)
DECLARE FUNCTION StrTok$ (Srce$, Delim$)

DECLARE SUB BrList (txt$(), NumLin AS INTEGER)
DECLARE SUB MsgBox (txt$(), NumLin AS INTEGER, Ky$, RestoreScrn AS INTEGER, Pause AS INTEGER)
DECLARE SUB SelectFile (FileName$)
DECLARE SUB SetConfig (Mode AS INTEGER)
DECLARE SUB UnPop ()

'DasLib.Bas
DECLARE FUNCTION A2dToVolt! (A2dVal AS INTEGER)
DECLARE FUNCTION VoltToD2a% (Volt!)

DECLARE SUB DasMode0 ()
DECLARE SUB DasMode1 (ChLow AS INTEGER, ChHigh AS INTEGER)
DECLARE SUB DasMode2 (NextCh AS INTEGER, ChLow AS INTEGER, ChHigh AS INTEGER)
DECLARE SUB DasMode3 (A2dData AS INTEGER, A2dCh AS INTEGER)
DECLARE SUB DasMode4 (NumPts AS INTEGER)
DECLARE SUB DasMode5 (NumPts AS INTEGER, Cycle AS INTEGER)
DECLARE SUB DasMode6 (NumPts AS INTEGER, Cycle AS INTEGER)
DECLARE SUB DasMode7 ()
DECLARE SUB DasMode8 (Op AS INTEGER, Status AS INTEGER, Count AS INTEGER)
DECLARE SUB DasMode9 (NumPts AS INTEGER, StartPt AS INTEGER)
DECLARE SUB DasMode15 (D2aCh AS INTEGER, D2aData AS INTEGER)
DECLARE SUB DasMode16 (D2aDat0 AS INTEGER, D2aDat1 AS INTEGER)
DECLARE SUB DasMode17 (Rate!)

'VentLib.Bas
DECLARE SUB Demo ()
DECLARE SUB InitVentLib ()
DECLARE SUB LoopTest ()
DECLARE SUB LoopTest5 ()
DECLARE SUB LoopTest6 ()
DECLARE SUB OhioFn ()
DECLARE SUB TestD2a ()
DECLARE SUB TestMode5 ()
DECLARE SUB TestMode6 ()
DECLARE SUB VentLoop ()
DECLARE SUB VentPlotGrid ()

DECLARE FUNCTION AvgA2dChan% (Count AS INTEGER, Chan AS INTEGER, Period AS INTEGER, NumCh AS
INTEGER, NumPts AS INTEGER)
 DECLARE FUNCTION RateToV! (Opt AS INTEGER, Volt!)

VentLib.Bas - Ohio 7000 Ventilator Control

```
DECLARE FUNCTION VolToVi (Opt AS INTEGER, Volt!)

'$INCLUDE: 'DasLib.Bi1'
'---------- DasLib.Bi1 ----------

'Das16 Common Area

'Das16 Parameters MUST be in common

CONST A2dBuffSize = 2000

DIM Dio(4) AS INTEGER
  DIM A2dBuff(2000) AS INTEGER
  DIM A2dChNum(2000) AS INTEGER COMMON Dio() AS INTEGER, Md AS INTEGER, Flag AS INTEGER
  COMMON BiPolar AS INTEGER, DasChan AS INTEGER, VoltFS AS SINGLE
  COMMON A2dBuff() AS INTEGER          'Buffer for DasMode4
  COMMON A2dChNum() AS INTEGER         'Buffer for A/D channel info 'for Mode 5 & 6, Quick Basic manages the Data Segment '$DYNAMIC
  'Dynamic Common is dimensioned AFTER the COMMON specification CONST A2dBuf2Size = 2000
  COMMON A2dBuf2() AS INTEGER         'Buffer for A/D data

'$STATIC

'---------- End DasLib.Bi1 ----------

'$INCLUDE: 'MenuSys.Bi1'
'---------- MenuSys.Bi1 ----------

' Constants for best available screen mode
  CONST VGA = 12
  CONST MCGA = 13
  CONST EGA256 = 9
  CONST EGA64 = 8
  CONST MONO = 10
  CONST HERC = 3
  CONST CGA = 1

' User-defined type to hold information about the mode
  TYPE Config
      Scrn    AS INTEGER
      Colors  AS INTEGER
      Atribs  AS INTEGER
      XPix    AS INTEGER
      YPix    AS INTEGER
      TCol    AS INTEGER
```

108

VentLib.Bas - Ohio 7000 Ventilator Control  PAGE   3
21 Nov 93
14:49:11
Microsoft (R) QuickBASIC Compiler Version 4.50

```
    TROW    AS INTEGER
END TYPE

'*****Graphics Modes
COMMON VC AS Config, InitRows AS INTEGER, BestMode AS INTEGER, Available AS STRING '*****Menu system
'$DYNAMIC
COMMON PopBuf() AS INTEGER, CurPath$, ForGnd AS INTEGER, Bakgnd AS INTEGER
'$STATIC '---------- End MenuSys.Bi1----------

'$INCLUDE: 'VentLib.Bi1'
'---------- VentLib.Bi1 ----------

'VentLib Dynamic Common declaration

TYPE VentDat           'Structure to hold modulation data
      Time AS SINGLE
      Mode AS STRING * 1
      Modulation AS SINGLE
    END TYPE CONST VentArrSize = 2000

COMMON VentArrNum AS INTEGER       '# of items loaded in VentArr()
    COMMON VentDatFn$                  'Data File loaded '$DYNAMIC
    'Dynamic Common is dimensioned AFTER the COMMON specification COMMON VentArr() AS VentDat        'Buffer for Ventilator modulation data

'$STATIC

'---------- End VentLib.Bi1 ----------

'$INCLUDE: 'DasLib.Bi2'
'---------- DasLib.Bi2 ----------
 DIM A2dBuf2(A2dBuf2Size) AS INTEGER
'---------- End DasLib.Bi2 ----------

'$INCLUDE: 'MenuSys.Bi2'
'---------- MenuSys.Bi2----------
 DIM PopBuf(2002, 1) AS INTEGER  'PopUp Buffer
'---------- End MenuSys.Bi2----------

'$INCLUDE: 'VentLib.Bi2'
'---------- VentLib.Bi2 ----------
 DIM VentArr(VentArrSize) AS VentDat  'Buffer for Ventilator modulation data
```

VentLib.Bas - Ohio 7000 Ventilator Control

PAGE 4
21 Nov 93
14:49:11
Microsoft (R) QuickBASIC Compiler Version 4.50

```
'---------- End VentLib.Bi2 ----------

'$Page $SubTitle:'FUNCTION AvgA2dChanX'
```

110

```
VentLib.Bas - Ohio 7000 Ventilator Control                              PAGE   5
FUNCTION AvgA2dChan%                                                    21 Nov 93
                                                                        14:49:11
                                      Microsoft (R) QuickBASIC Compiler Version 4.50

FUNCTION AvgA2dChan% (Count AS INTEGER, Chan AS INTEGER, Period AS INTEGER, NumCh AS INTEGER, N
umPts AS INTEGER)

'Function returns the average of an A/D channel over the previous Period
  'of observations, ending at position Count.
  'Data is input into A2dBuff() and A2dChNum() before call by DasMode9.
  'Count is provided by DasMode8, before call to DasMode9.
  '      is in range [0..(NumCh*NumPts)-1].
  'Chan is the channel # to average.
  'Period is the # of previous observations to average over.
  'NumCh channels of data is in data arrays.
  'NumPts is the number of points per channel.

'The index pointers may wrap around.

SHARED A2dBuff() AS INTEGER         'A/D data buffer
  SHARED A2dChNum() AS INTEGER        'channel # buffer DIM ptr AS INTEGER, i AS INTEGER
  DIM sum IF Count < 0 OR Count > (NumCh * NumPts) - 1 THEN
    PRINT "Count out of range in AvgA2dChan"
    DasMode7
    STOP
  END IF ptr = Count - 1           'use last conversion as end 'scan backwards until desired channel is located
  DO
    IF ptr < 0 THEN ptr = ptr + (NumCh * NumPts)     'protect wrap arounds
    IF A2dChNum(ptr) = Chan THEN EXIT DO
    ptr = ptr - 1
  LOOP sum = 0

FOR i = 1 TO Period
    IF ptr < 0 THEN ptr = ptr + (NumCh * NumPts)     'protect wrap arounds
'   IF A2dChNum(ptr) = Chan THEN
      sum = sum + A2dBuff(ptr)
'   END IF
    ptr = ptr - NumCh
  NEXT i AvgA2dChan% = sum / Period

END FUNCTION

'$Page $SubTitle:'SUB BrPrrData'
```

111

```
VentLib.Bas - Ohio 7000 Ventilator Control                              PAGE   6
SUB BrPrnData                                                           21 Nov 93
                                                                        14:49:11
                                        Microsoft (R) QuickBASIC Compiler Version 4.50

SUB BrPrnData

'Browse Ventilator modulation data

SHARED CurPath$, ForGnd AS INTEGER, Bakgnd AS INTEGER

SHARED VentArrNum AS INTEGER    '# of items loaded in VentArr()
  SHARED VentDatFn$               'Data File loaded
  SHARED VentArr() AS VentDat     'Buffer for Ventilator modulation data DIM i AS INTEGER, Ky$ IF VentArrNum = 0 THEN
     REDIM Msg$(3)
     Msg$(0) = "Browse Data"
     Msg$(1) = ""
     Msg$(2) = "NO data loaded"
     Msg$(3) = ""

MsgBox Msg$(), 3, Ky$, -1, -1    'unpop, pause
     ERASE Msg$
     EXIT SUB    'nothing to do
  END IF 'entertain the Human
  REDIM Msg$(3)
  Msg$(0) = "Browse Data"
  Msg$(1) = ""
  Msg$(2) = "Formating List..."
  Msg$(3) = ""

MsgBox Msg$(), 3, Ky$, 0, 0     'no unpop, no pause
  ERASE Msg$

'Create list to browse
  REDIM txt$(VentArrNum)

'Generate header
  txt$(0) = "File: " + VentDatFn$
  i = 80 - LEN(txt$(0))
  txt$(0) = txt$(0) + LPad$("ESC - Exit", i)

FOR i = 1 TO VentArrNum
     txt$(i) = LPad$(STR$(i), 5)
     txt$(i) = txt$(i) + FUse$(VentArr(i).Time, 10, 2)
     txt$(i) = txt$(i) + LPad$(LEFT$(VentArr(i).Mode, 1), 5)
     txt$(i) = txt$(i) + FUse$(VentArr(i).Modulation, 10, 2)
  NEXT i UnPop                   'Clear Message box BrList txt$(), VentArrNum
```

```
VentLib.Bas - Ohio 7000 Ventilator Control                    PAGE   7
SUB BrPrmData                                                 21 Nov 93
                                                              14:49:11
                                    Microsoft (R) QuickBASIC Compiler Version 4.50

ERASE txt$

END SUB

'$Page  $SubTitle:'SUB demo'
```

113

VentLib.Bas - Ohio 7000 Ventilator Control PAGE 8
SUB demo 21 Nov 93
14:49:11
Microsoft (R) QuickBASIC Compiler Version 4.50

```
SUB Demo

SHARED Dio() AS INTEGER, Md AS INTEGER, Flag AS INTEGER
    SHARED BiPolar AS INTEGER, DasChan AS INTEGER, VoltFS AS SINGLE
    SHARED A2dBuff() AS INTEGER          'Buffer for DasMode4
    SHARED A2dBuf2() AS INTEGER DIM NextCh AS INTEGER, ChLow AS INTEGER, ChHigh AS INTEGER DasMode0
    PRINT BiPolar, DasChan DasMode1 0, 3
    DasMode2 NextCh, ChLow, ChHigh
    PRINT NextCh, ChLow, ChHigh DasMode7

'Test Mode 3
    INPUT "mode 3 test"; a$
    FOR ch = 0 TO 3
      DasMode3 A2dDataX, A2dCh%
      PRINT A2dToVolt(A2dDataX), A2dCh%
    NEXT ch 'Test Mode 4
    INPUT "mode 4 test"; a$
    DasMode17 (100)
    DasMode4 (100)
    FOR i = 0 TO 99 STEP 4
      PRINT A2dBuff(i); A2dBuff(i + 1); A2dBuff(i + 2); A2dBuff(i + 3)
    NEXT i INPUT "mode 5 test"; a$
    TestMode5

INPUT "mode 6 test"; a$
    TestMode6

TestD2a

END SUB

'$Page $SubTitle:'SUB InitDas16'
```

VentLib.Bas - Ohio 7000 Ventilator Control
SUB InitDas16

PAGE 9
21 Nov 93
14:49:11
Microsoft (R) QuickBASIC Compiler Version 4.50

```
SUB InitDas16
  'General Reset
  DasMode0         'Init Driver
  DasMode7         'Clear DMA or Interrupt operation
  DasMode16 0, 0   'D/A's to zero
END SUB '$Page  $SubTitle:'SUB InitVentLib'
```

115

VentLib.Bas - Ohio 7000 Ventilator Control
SUB InitVentLib

PAGE 10
21 Nov 93
14:49:11
Microsoft (R) QuickBASIC Compiler Version 4.50

```
SUB InitVentLib

SHARED VentArrNum AS INTEGER    '# of items loaded in VentArr()
    SHARED VentDatFn$               'Data File loaded
    SHARED VentArr() AS VentDat     'Buffer for Ventilator modulation data VentArrNum = 0
    VentDatFn$ = ""

END SUB

'$Page  $SubTitle:'SUB LoadVentDatPrn'
```

116

VentLib.Bas - Ohio 7000 Ventilator Control  
SUB LoadVentDatPrn

PAGE 11  
21 Nov 93  
14:49:11  
Microsoft (R) QuickBASIC Compiler Version 4.50

```
SUB LoadVentDatPrn

'Load a .PRN format file created by a spreadsheet to emulate real data
'       Time  Rate/Volume  Modulation
'         0        R            6
'         0        V            2
'      4.23569    R         36.81015
'     13.60336    R         13.74554
'     20.26031    V         28.91379
'     25.65653    V         14.68135

SHARED CurPath$, ForGnd AS INTEGER, Bakgnd AS INTEGER

SHARED VentArrNum AS INTEGER       '# of items loaded in VentArr()
SHARED VentDatFn$                  'Data File loaded
SHARED VentArr() AS VentDat        'Buffer for Ventilator modulation data DIM Ky$, p$
DIM fp AS INTEGER, i AS INTEGER REDIM Msg$(5)
Msg$(0) = "Import VENTILATOR data"
Msg$(1) = ""
Msg$(2) = "Select an ASCII data file to load"
Msg$(3) = "as a Ventilator control data file."
Msg$(4) = ""
Msg$(5) = "Press any key to continue"

MsgBox Msg$(), 5, Ky$, -1, -1     'unpop, pause
ERASE Msg$

IF Ky$ = CHR$(27) THEN EXIT SUB   'ESC pressed

'Try to open a file
SelectFile VentDatFn$

IF VentDatFn$ = "" THEN            'nothing selected
  InitVentLib                      'clear common buffer
  EXIT SUB
END IF 'Display status box while loading
REDIM Msg$(3)
Msg$(0) = "Import VENTILATOR data"
Msg$(1) = ""
Msg$(2) = "Loading: " + CurPath$ + VentDatFn$
Msg$(3) = ""
MsgBox Msg$(), 3, Ky$, 0, 0        'no unpop, no pause
ERASE Msg$ fp = FREEFILE
OPEN CurPath$ + VentDatFn$ FOR INPUT AS #fp VentArrNum = 0         'init # loaded
```

```
VentLib.Bas - Ohio 7000 Ventilator Control                                    PAGE  12
SUB LoadVentDatPrn                                                            21 Nov 93
                                                                              14:49:11
                                            Microsoft (R) QuickBASIC Compiler Version 4.50 i = 1

DO WHILE NOT EOF(1)
      LINE INPUT #1, p$
      p$ = UCASE$(LTRIM$(RTRIM$(p$)))

IF LEN(p$) > 0 THEN
        'Parse input line
        VentArr(0).Time = VAL(StrTok$(p$, " "))
        VentArr(0).Mode = LEFT$(StrTok$("", " "), 1)
        VentArr(0).Modulation = VAL(StrTok$("", " "))

'test if valid - see format above
        IF VentArr(0).Time >= 0 AND (VentArr(0).Mode = "R" OR VentArr(0).Mode = "V") AND VentArr(
    0).Modulation > 0 THEN
          VentArr(i).Time = VentArr(0).Time
          VentArr(i).Mode = VentArr(0).Mode
          VentArr(i).Modulation = VentArr(0).Modulation
          VentArrNum = i
          i = i + 1
        END IF 'test if buffer exceeded
        IF i > VentArrSize THEN EXIT DO
      END IF

LOOP

CLOSE #fp

UnPop                       'Clear "Loading" Message - no unpop

IF VentArrNum = 0 THEN
      VentDatFn$ = ""
      EXIT SUB
    END IF

REDIM Msg$(5)
    Msg$(0) = "Import VENTILATOR data"
    Msg$(1) = ""
    Msg$(2) = "File: " + CurPath$ + VentDatFn$
    Msg$(3) = STR$(VentArrNum) + " obs. loaded"
    Msg$(4) = ""
    Msg$(5) = "Press any key to continue"

MsgBox Msg$(), 5, Ky$, -1, -1      'unpop, pause
    ERASE Msg$

END SUB

'$Page $SubTitle:'SUB LoopTest'
```

VentLib.Bas - Ohio 7000 Ventilator Control
SUB LoopTest

```
SUB LoopTest

'Closed Loop Test of Ohio Ventilator
   'R decreases modulated rate, T increases
   'V decreases modulated volume, B increases
   'Uses Mode4 Das16 operation SHARED A2dBuff() AS INTEGER       'Buffer for DasMode4

DIM cmd$, Avg(3), i AS INTEGER, VolCtrl, RateCtrl, VolMod, RateMod
   DIM VolOut, RateOut, VolD2a, RateD2a CLS
   PRINT "ESC to terminate Closed Loop Test"
   PRINT "R/T = -/+ Rate     V/B = -/+ Volume"

LOCATE 5, 15: PRINT "---Volume--"
   LOCATE 6, 15: PRINT "L/Min  Volt";

LOCATE 5, 30: PRINT "----Rate---"
   LOCATE 6, 30: PRINT "Bth/M  Volt";

LOCATE 7, 1: PRINT "Baseline";
   LOCATE 8, 1: PRINT "Modulation";
   LOCATE 9, 1: PRINT "D/A Drive";
   LOCATE 10, 1: PRINT "Output";

DasMode1 0, 3           'Setup Das16 for channels 0-3
   DasMode17 (100)         '100 Hz/Ch sampling rate 'Initialize keyboard volume and rate modulation values
   VolMod = 2
   RateMod = 6

DO

'Use Mode4 to get 100 mS of Data - speed medium
      DasMode4 (4 * 10)       '10 pts per channel @ 10 mS/Pt = 100 mS 'Cal avg of the volume and rate control settings
      Avg(0) = 0           'Volume
      Avg(2) = 0           'Rate
      FOR i = 0 TO (10 * 4) - 1 STEP 4
         Avg(0) = Avg(0) + A2dBuff(i)
         Avg(2) = Avg(2) + A2dBuff(i + 2)
      NEXT i Avg(0) = A2dToVolt(CINT(Avg(0) / 101))
      VolCtrl = VolToV(1, Avg(0))
      Avg(2) = A2dToVolt(CINT(Avg(2) / 101))
      RateCtrl = RateToV(1, Avg(2))

'Report Control settings to screen
```

VentLib.Bas - Ohio 7000 Ventilator Control  
SUB LoopTest

PAGE 14
21 Nov 93
14:49:11

Microsoft (R) QuickBASIC Compiler Version 4.50

```
    LOCATE 7, 15
    PRINT USING "##.## #.###"; VolCtrl; Avg(0);
    LOCATE 7, 30
    PRINT USING "##.## #.###"; RateCtrl; Avg(2);

cmd$ = INKEY$

SELECT CASE UCASE$(cmd$)
      CASE "R"
        IF RateMod > 6 THEN RateMod = RateMod - 1
      CASE "T"
        IF RateMod < 40 THEN RateMod = RateMod + 1

CASE "V"
        IF VolMod > 2 THEN VolMod = VolMod - 1
      CASE "B"
        IF VolMod < 30 THEN VolMod = VolMod + 1

CASE CHR$(27)
        EXIT DO
      CASE ""
      CASE ELSE
        BEEP
    END SELECT

'Display the Volume and Rate Modulations
    LOCATE 8, 15
    PRINT USING "##.## #.###"; VolMod; VolToV(2, VolMod);
    LOCATE 8, 30
    PRINT USING "##.## #.###"; RateMod; RateToV(2, RateMod);

'If the Modulation level is greater than the set point,
    'increase the drive to the ventilator VolD2a = 0
    IF VolMod > VolCtrl THEN
       VolD2a = VolToV(2, VolMod) - VolToV(2, VolCtrl)
    END IF RateD2a = 0
    IF RateMod > RateCtrl THEN
       RateD2a = RateToV(2, RateMod) - RateToV(2, RateCtrl)
    END IF 'Output modulation to D/A
    DasMode16 VoltToD2aX(VolD2a), VoltToD2aX(RateD2a)

'Display the Volume and Rate D/A Modulations levels
    LOCATE 9, 15
    PRINT USING "    #.###"; VolD2a;
    LOCATE 9, 30
```

VentLib.Bas - Ohio 7000 Ventilator Control
SUB LoopTest

PAGE 15
21 Nov 93
14:49:11
Microsoft (R) QuickBASIC Compiler Version 4.50

```
      PRINT USING "      #.###"; RateD2a;

'Use Mode4 to get 100 mS of Data - speed medium
   DasMode4 (4 * 10)         '10 pts per channel @ 10 mS/Pt = 100 mS 'Cal avg of the volume output and rate output levels
   Avg(1) = 0            'Volume Output
   Avg(3) = 0            'Rate Output
   FOR i = 0 TO (10 * 4) - 1 STEP 4
     Avg(1) = Avg(1) + A2dBuff(i + 1)
     Avg(3) = Avg(3) + A2dBuff(i + 3)
   NEXT i Avg(1) = A2dToVolt(CINT(Avg(1) / 10!))
   VolOut = VolToV(1, Avg(1))
   Avg(3) = A2dToVolt(CINT(Avg(3) / 10!))
   RateOut = RateToV(1, Avg(3))

'Report Outputs to screen
   LOCATE 10, 15
   PRINT USING "##.## #.###"; VolOut; Avg(1);
   LOCATE 10, 30
   PRINT USING "##.## #.###"; RateOut; Avg(3);

LOOP UNTIL cmd$ = CHR$(27)

'Zero D/A's
  DasMode16 0, 0

END SUB

'$Page $SubTitle:'SUB LoopTest5'
```

VentLib.Bas - Ohio 7000 Ventilator Control  
SUB LoopTest5

PAGE 16  
21 Nov 93  
14:49:11  
Microsoft (R) QuickBASIC Compiler Version 4.50

```
SUB LoopTest5

'Uses Mode5 Das16 operation

'Closed Loop Test of Ohio Ventilator
  'R decreases modulated rate, T increases
  'V decreases modulated volume, B increases SHARED A2dBuff() AS INTEGER          'Buffer for DasMode4

DIM cmd$, Avg(3), i AS INTEGER, VolCtrl, RateCtrl, VolMod, RateMod
  DIM VolOut, RateOut, VolD2a, RateD2a
  DIM Op AS INTEGER, Status AS INTEGER, Count AS INTEGER CLS
  PRINT "ESC to terminate Closed Loop Test"
  PRINT "R/T = -/+ Rate    V/B = -/+ Volume"

LOCATE 5, 15: PRINT "---Volume--"
  LOCATE 6, 15: PRINT "L/Min  Volt";

LOCATE 5, 30: PRINT "----Rate---"
  LOCATE 6, 30: PRINT "Bth/M  Volt";

LOCATE 7, 1: PRINT "Baseline";
  LOCATE 8, 1: PRINT "Modulation";
  LOCATE 9, 1: PRINT "D/A Drive";
  LOCATE 10, 1: PRINT "Output";

DasMode1 0, 3              'Setup Das16 for channels 0-3
  DasMode17 (100)            '100 Hz/Ch sampling rate 'Initialize keyboard volume and rate modulation values
  VolMod = 2
  RateMod = 6

DO

'Use Mode5 to get 100 mS of Data - speed medium - Background
    DasMode5 4 * 10, 0     'get 10 pts per channel, only one cycle 'watch Count until done
    DO
      DasMode8 Op, Status, Count
    LOOP UNTIL Status = 0

DasMode9 10 * 4, 0         'Xfer to A2dBuff()

'Cal avg of the volume and rate control settings
    Avg(0) = 0          'Volume
    Avg(2) = 0          'Rate
    FOR i = 0 TO (10 * 4) - 1 STEP 4
```

```
VentLib.Bas - Ohio 7000 Ventilator Control                                    PAGE  17
SUB LoopTest5                                                                 21 Nov 93
                                                                              14:49:11
                                              Microsoft (R) QuickBASIC Compiler Version 4.50

Avg(0) = Avg(0) + A2dBuff(i)
      Avg(2) = Avg(2) + A2dBuff(i + 2)
   NEXT i

Avg(0) = A2dToVolt(CINT(Avg(0) / 10!))
   VolCtrl = VolToV(1, Avg(0))
   Avg(2) = A2dToVolt(CINT(Avg(2) / 10!))
   RateCtrl = RateToV(1, Avg(2))

'Report Control settings to screen
   LOCATE 7, 15
   PRINT USING "##.## #.###"; VolCtrl; Avg(0);
   LOCATE 7, 30
   PRINT USING "##.## #.###"; RateCtrl; Avg(2);

cmd$ = INKEY$

SELECT CASE UCASE$(cmd$)
      CASE "R"
         IF RateMod > 6 THEN RateMod = RateMod - 1
      CASE "T"
         IF RateMod < 40 THEN RateMod = RateMod + 1

CASE "V"
         IF VolMod > 2 THEN VolMod = VolMod - 1
      CASE "B"
         IF VolMod < 30 THEN VolMod = VolMod + 1

CASE CHR$(27)
         EXIT DO
      CASE ""
      CASE ELSE
         BEEP
   END SELECT

'Display the Volume and Rate Modulations
   LOCATE 8, 15
   PRINT USING "##.## #.###"; VolMod; VolToV(2, VolMod);
   LOCATE 8, 30
   PRINT USING "##.## #.###"; RateMod; RateToV(2, RateMod);

'If the Modulation level is greater than the set point,
   'increase the drive to the ventilator VolD2a = 0
   IF VolMod > VolCtrl THEN
      VolD2a = VolToV(2, VolMod) - VolToV(2, VolCtrl)
   END IF RateD2a = 0
   IF RateMod > RateCtrl THEN
```

```
VentLib.Bas - Ohio 7000 Ventilator Control                                    PAGE  18
SUB LoopTest5                                                                 21 Nov 93
                                                                              14:49:11
                                            Microsoft (R) QuickBASIC Compiler Version 4.50

RateD2a = RateToV(2, RateMod) - RateToV(2, RateCtrl)
    END IF

'Output modulation to D/A
    DasMode16 VoltToD2aX(VolD2a), VoltToD2aX(RateD2a)

'Display the Volume and Rate D/A Modulations levels
    LOCATE 9, 15
    PRINT USING "        #.###"; VolD2a;
    LOCATE 9, 30
    PRINT USING "        #.###"; RateD2a;

'Use Mode5 to get 100 mS of Data - speed medium - Background
    DasMode5 4 * 10, 0      'get 10 pts per channel, only one cycle 'watch Count until done
    DO
       DasMode8 Op, Status, Count
    LOOP UNTIL Status = 0

DasMode9 10 * 4, 0         'Xfer to A2dBuff()

'Cal avg of the volume output and rate output levels
    Avg(1) = 0            'Volume Output
    Avg(3) = 0            'Rate Output
    FOR i = 0 TO (10 * 4) - 1 STEP 4
       Avg(1) = Avg(1) + A2dBuff(i + 1)
       Avg(3) = Avg(3) + A2dBuff(i + 3)
    NEXT i Avg(1) = A2dToVolt(CINT(Avg(1) / 10!))
    VolOut = VolToV(1, Avg(1))
    Avg(3) = A2dToVolt(CINT(Avg(3) / 10!))
    RateOut = RateToV(1, Avg(3))

'Report Outputs to screen
    LOCATE 10, 15
    PRINT USING "##.## #.###"; VolOut; Avg(1);
    LOCATE 10, 30
    PRINT USING "##.## #.###"; RateOut; Avg(3);

LOOP UNTIL cmd$ = CHR$(27)

DasMode16 0, 0          'Zero D/A's
  DasMode7                'Disable Interrupt

END SUB

'$Page $SubTitle:'SUB LoopTest6'
```

```
VentLib.Bas - Ohio 7000 Ventilator Control                                        PAGE  19
SUB LoopTest6                                                                    21 Nov 93
                                                                                 14:49:11
                                                  Microsoft (R) QuickBASIC Compiler Version 4.50

SUB LoopTest6

'Uses Mode6 Das16 operation

'Closed Loop Test of Ohio Ventilator
    'R decreases modulated rate, T increases
    'V decreases modulated volume, B increases SHARED A2dBuff() AS INTEGER          'Buffer for DasMode4

DIM cmd$, Avg(3), i AS INTEGER, VolCtrl, RateCtrl, VolMod, RateMod
    DIM VolOut, RateOut, VolD2a, RateD2a
    DIM Op AS INTEGER, Status AS INTEGER, Count AS INTEGER CLS
    PRINT "ESC to terminate Closed Loop Test"
    PRINT "R/T = -/+ Rate     V/B = -/+ Volume"

LOCATE 5, 15: PRINT "---Volume--"
    LOCATE 6, 15: PRINT "L/Min  Volt";

LOCATE 5, 30: PRINT "----Rate---"
    LOCATE 6, 30: PRINT "Bth/M  Volt";

LOCATE 7, 1: PRINT "Baseline";
    LOCATE 8, 1: PRINT "Modulation";
    LOCATE 9, 1: PRINT "D/A Drive";
    LOCATE 10, 1: PRINT "Output";

DasMode1 0, 3           'Setup Das16 for channels 0-3
    DasMode17 (100)         '100 Hz/Ch sampling rate 'Initialize keyboard volume and rate modulation values
    VolMod = 2
    RateMod = 6

DO

'Use Mode6 to get 100 mS of Data - speed high - Background
      DasMode6 4 * 10, 0     'get 10 pts per channel, only one cycle 'watch Count until done
      DO
        DasMode8 Op, Status, Count
      LOOP UNTIL Status = 0

DasMode9 10 * 4, 0            'Xfer to A2dBuff()

'Cal avg of the volume and rate control settings
      Avg(0) = 0          'Volume
      Avg(2) = 0          'Rate
      FOR i = 0 TO (10 * 4) - 1 STEP 4
```

VentLib.Bas - Ohio 7000 Ventilator Control
SUB LoopTest6

```
        Avg(0) = Avg(0) + A2dBuff(i)
        Avg(2) = Avg(2) + A2dBuff(i + 2)
    NEXT i Avg(0) = A2dToVolt(CINT(Avg(0) / 101))
    VolCtrl = VolToV(1, Avg(0))
    Avg(2) = A2dToVolt(CINT(Avg(2) / 101))
    RateCtrl = RateToV(1, Avg(2))

'Report Control settings to screen
    LOCATE 7, 15
    PRINT USING "##.## #.###"; VolCtrl; Avg(0);
    LOCATE 7, 30
    PRINT USING "##.## #.###"; RateCtrl; Avg(2);

cmd$ = INKEY$

SELECT CASE UCASE$(cmd$)
        CASE "R"
            IF RateMod > 6 THEN RateMod = RateMod - 1
        CASE "T"
            IF RateMod < 40 THEN RateMod = RateMod + 1

CASE "Y"
            IF VolMod > 2 THEN VolMod = VolMod - 1
        CASE "B"
            IF VolMod < 30 THEN VolMod = VolMod + 1

CASE CHR$(27)
            EXIT DO
        CASE ""
        CASE ELSE
            BEEP
    END SELECT

'Display the Volume and Rate Modulations
    LOCATE 8, 15
    PRINT USING "##.## #.###"; VolMod; VolToV(2, VolMod);
    LOCATE 8, 30
    PRINT USING "##.## #.###"; RateMod; RateToV(2, RateMod);

'if the Modulation level is greater than the set point,
    'increase the drive to the ventilator VolD2a = 0
    IF VolMod > VolCtrl THEN
        VolD2a = VolToV(2, VolMod) - VolToV(2, VolCtrl)
    END IF RateD2a = 0
    IF RateMod > RateCtrl THEN
```

VentLib.Bas - Ohio 7000 Ventilator Control    PAGE 21
SUB LoopTest6                                  21 Nov 93
                                               14:49:11
                       Microsoft (R) QuickBASIC Compiler Version 4.50

```
    RateD2a = RateToV(2, RateMod) - RateToV(2, RateCtrl)
  END IF

'Output modulation to D/A
  DasMode16 VoltToD2aX(VolD2a), VoltToD2aX(RateD2a)

'Display the Volume and Rate D/A Modulations levels
  LOCATE 9, 15
  PRINT USING "     #.###"; VolD2a;
  LOCATE 9, 30
  PRINT USING "     #.###"; RateD2a;

'Use Mode6 to get 100 mS of Data - speed high - Background
  DasMode6 4 * 10, 0     'get 10 pts per channel, only one cycle 'watch Count until done
  DO
     DasMode8 Op, Status, Count
  LOOP UNTIL Status = 0

DasMode9 10 * 4, 0         'Xfer to A2dBuff()

'Cal avg of the volume output and rate output levels
  Avg(1) = 0          'Volume Output
  Avg(3) = 0          'Rate Output
  FOR i = 0 TO (10 * 4) - 1 STEP 4
     Avg(1) = Avg(1) + A2dBuff(i + 1)
     Avg(3) = Avg(3) + A2dBuff(i + 3)
  NEXT i Avg(1) = A2dToVolt(CINT(Avg(1) / 10!))
  VolOut = VolToV(1, Avg(1))
  Avg(3) = A2dToVolt(CINT(Avg(3) / 10!))
  RateOut = RateToV(1, Avg(3))

'Report Outputs to screen
  LOCATE 10, 15
  PRINT USING "##.## #.###"; VolOut; Avg(1);
  LOCATE 10, 30
  PRINT USING "##.## #.###"; RateOut; Avg(3);

LOOP UNTIL cmd$ = CHR$(27)

DasMode16 0, 0         'Zero D/A's
DasMode7               'Disable Interrupt

END SUB

'$Page $SubTitle:'SUB OhioFn'
```

VentLib.Bas - Ohio 7000 Ventilator Control
SUB OhioFn

```
SUB OhioFn
  'VentFn4.Bas
  'Sept 29/93

DIM i AS INTEGER, Volt, Vol, Rate

DasMode0
  DasMode1 0, 3
  DasMode7

CLS
  LOCATE 4, 1
  PRINT "Volt";
  LOCATE 5, 1
  PRINT "Calc";
  LOCATE 3, 10
  PRINT "-----Litre/Min-----";
  LOCATE 3, 40
  PRINT "-----Breath/Min-----";

DO
    FOR ch = 0 TO 3
      DasMode3 A2dDataX, A2dChX
      PRINT A2dChX;

IF ch < 2 THEN
        LOCATE 6, 10 + (ch * 15)
        PRINT USING "####"; A2dDataX;
        LOCATE 4, 10 + (ch * 15)
        PRINT USING "#.##"; A2dToVolt(A2dDataX);
        IF ch = 1 THEN DasMode15 0, VoltToD2aX(A2dToVolt(A2dDataX))
        LOCATE 5, 10 + (ch * 15)
        PRINT USING "##.##"; VolToV(1, A2dToVolt(A2dDataX));

ELSE
        LOCATE 4, 10 + (ch * 15)
        PRINT USING "#.##"; A2dToVolt(A2dDataX);
        LOCATE 5, 10 + (ch * 15)
        PRINT USING "##.##"; RateToV(1, A2dToVolt(A2dDataX));
      END IF NEXT ch
    PRINT
    a$ = INKEY$
  LOOP UNTIL a$ <> ""

EXIT SUB

FOR i = 2 TO 30
    Volt = VolToV(2, CSNG(i))
    Vol = VolToV(1, Volt)
```

VentLib.Bas - Ohio 7000 Ventilator Control  PAGE 23
SUB OhioFn  21 Nov 93
  14:49:11
  Microsoft (R) QuickBASIC Compiler Version 4.50

```
    PRINT USING "## #.### ####.#"; i; Volt; Vol
    IF i MOD 10 = 0 THEN INPUT a$
  NEXT i FOR i = 6 TO 40
    Volt = RateToV(2, CSNG(i))
    Rate = RateToV(1, Volt)
    PRINT USING "## #.### ####.#"; i; Volt; Rate
    IF i MOD 10 = 0 THEN INPUT a$
  NEXT i

END SUB

'$Page  $SubTitle:'SUB PlotVentDat'
```

```
VentLib.Bas - Ohio 7000 Ventilator Control                              PAGE  24
SUB PlotVentDat                                                         21 Nov 93
                                                                        14:49:11
                                          Microsoft (R) QuickBASIC Compiler Version 4.50

SUB PlotVentDat

SHARED VentArrNum AS INTEGER     '# of items loaded in VentArr()
    SHARED VentDatFn$                'Data File loaded
    SHARED VentArr() AS VentDat      'Buffer for Ventilator modulation data DIM i AS INTEGER, init AS INTEGER
    DIM oldY AS SINGLE IF VentArrNum = 0 THEN
       REDIM Msg$(3)
       Msg$(0) = "Plot Data"
       Msg$(1) = ""
       Msg$(2) = "NO data loaded"
       Msg$(3) = ""

MsgBox Msg$(), 3, Ky$, -1, -1     'unpop, pause
       ERASE Msg$
       EXIT SUB    'nothing to do
    END IF VentPlotGrid              'draw axis and define plot window 'Plot Volume
    WINDOW (0, 0)-(VentArr(VentArrNum).Time, 30)

init = -1

FOR i = 1 TO VentArrNum
       IF VentArr(i).Mode = "V" THEN         'Volume data
          IF init THEN
             init = 0
             PSET (VentArr(i).Time, VentArr(i).Modulation), 1
             oldY = VentArr(i).Modulation
          ELSE
             LINE -(VentArr(i).Time, oldY), 1
             LINE -(VentArr(i).Time, VentArr(i).Modulation), 1
             oldY = VentArr(i).Modulation
          END IF
       END IF
    NEXT i 'Plot Rate
    WINDOW (0, 0)-(VentArr(VentArrNum).Time, 40)

init = -1

FOR i = 1 TO VentArrNum
       IF VentArr(i).Mode = "R" THEN         'Rate data
          IF init THEN
             init = 0
             PSET (VentArr(i).Time, VentArr(i).Modulation), 2
             oldY = VentArr(i).Modulation
          ELSE
```

129

VentLib.Bas - Ohio 7000 Ventilator Control  
SUB PlotVentDat

PAGE 25  
21 Nov 93  
14:49:11  
Microsoft (R) QuickBASIC Compiler Version 4.50

```
      LINE -(VentArr(i).Time, oldY), 2
      LINE -(VentArr(i).Time, VentArr(i).Modulation), 2
      oldY = VentArr(i).Modulation
     END IF
   END IF
 NEXT i DO
   a$ = INKEY$
 LOOP UNTIL a$ <> ""
 SCREEN 0, 0, 0
 WIDTH 80

END SUB

'$Page  $SubTitle:'FUNCTION RateToV'
```

131

VentLib.Bas - Ohio 7000 Ventilator Control  
FUNCTION RateToV

PAGE 26  
21 Nov 93  
14:49:11  
Microsoft (R) QuickBASIC Compiler Version 4.50

```
FUNCTION RateToV (Opt AS INTEGER, Volt)

'Sept 29/93
    '--------------------------------------------------
    'Function Library for Ohio 7000 Ventilator Control
    '--------------------------------------------------

'Based on observations of Breath/Min Rate control
    '   Y =    a    +    bX
    '   mV = 18.06555 + 50.48908 * Rate      R^2=0.999555

'   V = 1.80655462E-02 + 5.04890756E-02 * Rate    R^2=0.999555

'   Rate      Regression Output:
    '   Constant                           1.80655462E-02
    '   Std Err of Y Est                   1.10777101E-02
    '   R Squared                          9.99555207E-01
    '   No. of Observations                            35
    '   Degrees of Freedom                             33
    '
    '   X Coefficient(s)     5.04890756E-02
    '   Std Err of Coef.     1.85402629E-04

DIM V, Rate, a, b

'   V = 1.80655462E-02 + 5.04890756E-02 * Rate    R^2=0.999555
    a = .0180655462#
    b = .0504890756#

SELECT CASE Opt%
        CASE 1           'V to Rate
            V = Volt
            Rate = (V - a) / b      ' x = (Y - a) / b
            RateToV = Rate
        CASE 2           'Rate to V
            Rate = Volt
            V = a + b * Rate        ' y = a + bx
            RateToV = V
    END SELECT

END FUNCTION

'$Page $SubTitle:'SUB TestD2a'
```

VentLib.Bas - Ohio 7000 Ventilator Control  
SUB TestO2a

PAGE 27  
21 Nov 93  
14:49:11  
Microsoft (R) QuickBASIC Compiler Version 4.50

```
SUB TestO2a

DIM I AS INTEGER, a$

INPUT "Channel 0 ramp"; a$
  FOR I = 0 TO 4095 STEP 2
    DasMode15 0, I
  NEXT I
  DasMode15 0, 0

INPUT "Channel 1 ramp"; a$
  FOR I = 0 TO 4095 STEP 2
    DasMode15 1, I
  NEXT I
  DasMode15 1, 0

INPUT "Dual Channel ramp"; a$
  FOR I = 0 TO 4095 STEP 2
    DasMode16 I, I
  NEXT I
  DasMode16 0, 0

END SUB

'$Page $SubTitle:'SUB TestMode5'
```

VentLib.Bas - Ohio 7000 Ventilator Control
SUB TestMode5

```
SUB TestMode5

SHARED A2dBuff() AS INTEGER        'A/D data buffer
    SHARED A2dChNum() AS INTEGER       'channel # buffer DIM Op AS INTEGER, Status AS INTEGER, Count AS INTEGER, i AS INTEGER DasMode0            'init
    DasMode1 0, 3       'scan 0 to 3
    DasMode17 (100)     'sample @ 100 Hz
    DasMode5 500, 0     'get 500 pts, only one cycle DO
      DasMode8 Op, Status, Count
      PRINT Op, Status, Count
    LOOP UNTIL Status = 0
    PRINT Op, Status, Count DasMode9 500, 0         'Xfer to A2dBuff(), A2dChNum()

FOR i = 0 TO 499 STEP 4
      PRINT A2dChNum(i); A2dBuff(i), A2dChNum(i + 1); A2dBuff(i + 1), A2dChNum(i + 2); A2dBuff(i
    + 2), A2dChNum(i + 3); A2dBuff(i + 3)
    NEXT i DasMode7            'clear Background operation
END SUB '$Page $SubTitle:'SUB TestMode6'
```

134

VentLib.Bas - Ohio 7000 Ventilator Control　　　　　　　　　　　　　PAGE  29
SUB TestMode6　　　　　　　　　　　　　　　　　　　　　　　　　　21 Nov 93
　　　　　　　　　　　　　　　　　　　　　　　　　　　　　　　14:49:11
　　　　　　　　　　　　　　　　　　　Microsoft (R) QuickBASIC Compiler Version 4.50

```
SUB TestMode6

SHARED A2dBuff() AS INTEGER       'A/D data buffer
    SHARED A2dChNum() AS INTEGER      'channel # buffer DIM Op AS INTEGER, Status AS INTEGER, Count AS INTEGER, i AS INTEGER DasMode0            'init
    DasMode1 0, 3       'scan 0 to 3
    DasMode17 (100)     'sample @ 100 Hz
    DasMode6 500, 0     'get 100 pts, only one cycle DO
        DasMode8 Op, Status, Count
        PRINT Op, Status, Count
    LOOP UNTIL Status = 0

DasMode9 500, 0         'Xfer to A2dBuff()

FOR i = 0 TO 499 STEP 4
        PRINT A2dChNum(i); A2dBuff(i), A2dChNum(i + 1); A2dBuff(i + 1), A2dChNum(i + 2); A2dBuff(i
+ 2), A2dChNum(i + 3); A2dBuff(i + 3)
    NEXT i DasMode7            'clear Background operation
END SUB '$Page $SubTitle:'SUB VentLoop'
```

```
VentLib.Bas - Ohio 7000 Ventilator Control                              PAGE  30
SUB VentLoop                                                            21 Nov 93
                                                                        14:49:11
                                         Microsoft (R) QuickBASIC Compiler Version 4.50

SUB VentLoop

'Uses function to return avg of A/D channels when running
   'in continuous acquisition mode 6.

'Modulates ventilator with data in common - if loaded.

SHARED VentArrNum AS INTEGER      '# of items loaded in VentArr()
   SHARED VentDatFn$                 'Data File loaded
   SHARED VentArr() AS VentDat       'Buffer for Ventilator modulation data DIM Op AS INTEGER, Status AS INTEGER, Count AS INTEGER
   DIM OldCount AS INTEGER, Done AS INTEGER, Chan AS INTEGER
   DIM i AS INTEGER
   DIM a$, mask$, mask1$ DIM tStart AS SINGLE              'starting time
   DIM tNow AS SINGLE                'current time DIM NumCh AS INTEGER              '# channels to acquire
   DIM PtsPerCh AS INTEGER           '# points per channel
   DIM AvPer AS INTEGER              'Avg Period of A/D data DIM VolMod, RateMod               'Vol & Rate Modulation level
   DIM VolModV, RateModV             'Volts of Vol & Rate Modulation level DIM VolCtrl, RateCtrl             'Setting of ventilator Vol & Rate Ctrls
   DIM VolCtrlV, RateCtrlV           'Volts of ventilator Vol & Rate Ctrls DIM VolD2a, RateD2a               'D/A outputs for Volume and Rate DIM Vol, Rate                     'Current drive to Ventilator
   DIM VolV, RateV                   'Current drive Voltage to Ventilator NumCh = 4                         'channels 0 to 3
   PtsPerCh = 20                     'acquire 20 pts per channel
   AvPer = 10                        'average previous 100 mS DasMode0                          'Init Driver
   DasMode7                          'Clear DMA or Interrupt operation
   DasMode16 0, 0                    'D/A's to zero 'Build Status Screen
   COLOR 14, 1
   CLS
   a$ = "Ventilation Control - Press ESC to Terminate"
   LOCATE 1, 40 - LEN(a$) / 2
   PRINT a$ IF VentArrNum > 0 THEN            'Display Modulation file - if loaded
      a$ = "File: " + VentDatFn$
      LOCATE 25, 40 - LEN(a$) / 2
      PRINT a$;
```

VentLib.Bas - Ohio 7000 Ventilator Control
SUB VentLoop

PAGE 31
21 Nov 93
14:49:11
Microsoft (R) QuickBASIC Compiler Version 4.50

```
    END IF

LOCATE 7, 30
    PRINT "--Volume---"
    LOCATE 8, 30
    PRINT "L/Min  Volt"

LOCATE 7, 45
    PRINT "---Rate----"
    LOCATE 8, 45
    PRINT "Bth/M  Volt"

LOCATE 10, 15
    PRINT "BaseLine"
    LOCATE 11, 15
    PRINT "Modulation"
    LOCATE 12, 15
    PRINT "D/A Drive"
    LOCATE 13, 15
    PRINT "Output"
    mask$ = "##.## #.###"
    mask1$ = "      #.###"

DasMode1 0, NumCh - 1       'Setup Das16 for channels 0-3
    DasMode17 (100)             '100 Hz/Ch sampling rate 'Use Mode6 to get 200 mS of Data - speed high - Background
    DasMode6 NumCh * PtsPerCh, 1   'get 10 pts per ch, cycle continuously 'Wait until filled A/D buffer once - 200 mS DasMode8 Op, Status, OldCount   'look at A/D buffer index pointer
    Done = 0
    DO
        DasMode8 Op, Status, Count  'look at A/D buffer index pointer IF Count < OldCount THEN    'wrapped around!
            Done = -1
        ELSE
            OldCount = Count        'wait until wrap around
        END IF LOOP UNTIL Done VolMod = 2                  'Zero Modulation Levels
    RateMod = 6

'What to do i = 0

DO
```

137

```
VentLib.Bas - Ohio 7000 Ventilator Control                              PAGE  32
SUB VentLoop                                                            21 Nov 93
                                                                        14:49:11
                                        Microsoft (R) QuickBASIC Compiler Version 4.50

IF i = 0 THEN              'Init
      i = 1
      tStart = TIMER           'remember starting time
    END IF 'If data loaded, see if it is time to change modulation level
    IF VentArrNum > 0 THEN
      tNow = TIMER - tStart IF tNow < 0 THEN tNow = tNow + 86400   'working late eh!

IF tNow >= VentArr(i).Time THEN        'change modulation
    '   LOCATE 17, 30
    '   PRINT USING "####.# | ##.##"; tNow; VentArr(i).Mode; VentArr(i).Modulation SELECT CASE VentArr(i).Mode
          CASE "R"
            RateMod = VentArr(i).Modulation
            i = i + 1
          CASE "V"
            VolMod = VentArr(i).Modulation
            i = i + 1
        END SELECT
      END IF 'When we reach the end of the data send [VentArr()] - wrap arround
      IF i > VentArrNum THEN i = 0

END IF t1 = TIMER
    IF 1 = 1 THEN                    'Volume

'Read Volume control - avg of previous 100 mS
      DasMode8 Op, Status, Count     'determine current index pointer
      DasMode9 NumCh * PtsPerCh, 0   'Xfer to A2dBuff(), A2dChNum()

'Read Volume control position
      Chan = 0
      VolCtrlV = A2dToVolt(AvgA2dChanX(Count, Chan, AvPer, NumCh, PtsPerCh))
      VolCtrl = VolToV(1, VolCtrlV)

'Read Volume Ventilator is running at
      Chan = 1
      VolV = A2dToVolt(AvgA2dChanX(Count, Chan, AvPer, NumCh, PtsPerCh))
      Vol = VolToV(1, VolV)

'Calculate Volume Modulation into volts
      VolModV = VolToV(2, VolMod)

'Calculate D/A drive to Achieve Modulation Level
      IF VolModV > VolCtrlV THEN       'Modulation > set point
```

VentLib.Bas - Ohio 7000 Ventilator Control  
SUB VentLoop

PAGE 33  
21 Nov 93  
14:49:11  
Microsoft (R) QuickBASIC Compiler Version 4.50

```
        VolD2a = VolModV - VolCtrlV
    ELSE                            'Modulation <= set point
        VolD2a = 0
    END IF 'Send the Volume Drive to the Ventilator via D/A channel 0
    DasMode15 0, VoltToD2aX(VolD2a)

LOCATE 10, 30
    PRINT USING mask$; VolCtrl; VolCtrlV
    LOCATE 11, 30
    PRINT USING mask$; VolMod; VolModV
    LOCATE 12, 30
    PRINT USING mask1$; VolD2a
    LOCATE 13, 30
    PRINT USING mask$; Vol; VolV
END IF IF 2 = 2 THEN                       'Rate 'Read Rate control - avg of previous 100 mS
    DasMode8 Op, Status, Count      'determine current index pointer
    DasMode9 NumCh * PtsPerCh, 0    'Xfer to A2dBuff(), A2dChNum()

'Read Rate control position
    Chan = 2
    RateCtrlV = A2dToVolt(AvgA2dChanX(Count, Chan, AvPer, NumCh, PtsPerCh))
    RateCtrl = RateToV(1, RateCtrlV)

'Read Rate Ventilator is running at
    Chan = 3
    RateV = A2dToVolt(AvgA2dChanX(Count, Chan, AvPer, NumCh, PtsPerCh))
    Rate = RateToV(1, RateV)

'Calculate Rate Modulation into volts
    RateModV = RateToV(2, RateMod)

'Calculate D/A drive to Achieve Modulation Level
    IF RateModV > RateCtrlV THEN    'Modulation > set point
        RateD2a = RateModV - RateCtrlV
    ELSE                            'Modulation <= set point
        RateD2a = 0
    END IF 'Send the Rate Drive to the Ventilator via D/A channel 1
    DasMode15 1, VoltToD2aX(RateD2a)

LOCATE 10, 45
    PRINT USING mask$; RateCtrl; RateCtrlV
    LOCATE 11, 45
    PRINT USING mask$; RateMod; RateModV
    LOCATE 12, 45
```

VentLib.Bas - Ohio 7000 Ventilator Control
SUB VentLoop

PAGE 34
21 Nov 93
14:49:11
Microsoft (R) QuickBASIC Compiler Version 4.50

```
    PRINT USING mask1$; RateD2a
    LOCATE 13, 45
    PRINT USING mask$; Rate; RateV
  END IF
  t2 = TIMER LOCATE 15, 30: PRINT USING "loop time = ##.##"; t2 - t1 a$ = INKEY$
LOOP UNTIL a$ = CHR$(27)

DasMode16 0, 0          'Zero D/A's
DasMode7                'Disable Interrupt

END SUB

'$Page $SubTitle:'SUB VentPlotGrid'
```

140

VentLib.Bas - Ohio 7000 Ventilator Control
SUB VentPlotGrid

PAGE 35
21 Nov 93
14:49:11
Microsoft (R) QuickBASIC Compiler Version 4.50

```
SUB VentPlotGrid

SHARED Vc AS Config, InitRows AS INTEGER, BestMode AS INTEGER, Available AS STRING SHARED VentArrNum AS INTEGER      '# of items loaded in VentArr()
    SHARED VentDatFn$                 'Data File loaded
    SHARED VentArr() AS VentDat       'Buffer for Ventilator modulation data DIM txtX AS INTEGER, txtY AS INTEGER
    DIM x1 AS INTEGER, x2 AS INTEGER, y1 AS INTEGER, y2 AS INTEGER
    DIM i AS INTEGER
    DIM r AS SINGLE SCREEN BestMode
    SetConfig BestMode         'Fill in VC Parameters COLOR 1, 1         'White BackGround, Palette 1
    CLS 'Calculate Char size in this mode
    txtX = (Vc.XPix + 1) \ Vc.TCol
    txtY = (Vc.YPix + 1) \ Vc.TRow 'Label Header
    LOCATE 1, 7
    PRINT "File: "; VentDatFn$;

'Label Left Vertical Axis - Volume
    LOCATE 2, 2: PRINT "Vol";
    LOCATE 3, 3: PRINT "30";
    LOCATE Vc.TRow - 2, 3: PRINT " 0";

'Tick Left Axis [0..30] every 5
    x1 = 4 * txtX
    x2 = 5 * txtX
    y1 = 2 * txtY + (txtY) \ 2
    y2 = (Vc.TRow - 2) * txtY - (txtY) \ 2
    VIEW (x1, y1)-(x2, y2)
    WINDOW (0, 1)-(1, 7)
    FOR i = 1 TO 7
        LINE (0, i)-(1, i), 1
    NEXT i 'Label Right Vertical Axis - Rate
    LOCATE 2, Vc.TCol - 4: PRINT "Rate";
    LOCATE 3, Vc.TCol - 4: PRINT "40";
    LOCATE Vc.TRow - 2, Vc.TCol - 4: PRINT " 0";

'Tick Right Axis [0..40] every 5
    x1 = (Vc.TCol - 5) * txtX
    x2 = (Vc.TCol - 6) * txtX
    y1 = 2 * txtY + (txtY) \ 2
    y2 = (Vc.TRow - 2) * txtY - (txtY) \ 2
    VIEW (x1, y1)-(x2, y2)
```

141

VentLib.Bas - Ohio 7000 Ventilator Control
SUB VentPlotGrid

PAGE 36
21 Nov 93
14:49:11
Microsoft (R) QuickBASIC Compiler Version 4.50

```
WINDOW (0, 1)-(1, 9)
FOR i = 1 TO 9
  LINE (0, i)-(1, i), 2
NEXT i

'Label X Axis
LOCATE Vc.TRow, (Vc.TCol \ 2) - 2
PRINT "(Sec)";
LOCATE Vc.TRow, 6
PRINT "0.0";
LOCATE Vc.TRow, Vc.TCol - 4 - 6
PRINT FUseS(VentArr(VentArrNum).Time, 6, 1);

'Tick Horizontal Axis by 100 Secs
x1 = 5 * txtX
x2 = (Vc.TCol - 6) * txtX
y1 = (Vc.TRow - 2) * txtY - (txtY) \ 2
y2 = y1 + (txtY \ 2)
VIEW (x1, y1)-(x2, y2)
WINDOW (0, 0)-(VentArr(VentArrNum).Time, 1)
FOR r = 0 TO VentArr(VentArrNum).Time STEP 100
  LINE (r, 0)-(r, 1), 3
NEXT r 'Exit with the Plot Window defined
x1 = 5 * txtX' - 1
x2 = (Vc.TCol - 6) * txtX' + 1
y1 = 2 * txtY + (txtY) \ 2' - 1
y2 = (Vc.TRow - 2) * txtY - (txtY) \ 2' + 1
VIEW (x1, y1)-(x2, y2), 3, 3

END SUB

'$Page $SubTitle:'FUNCTION VolToV'
```

142

```
VentLib.Bas - Ohio 7000 Ventilator Control                                    PAGE  37
FUNCTION VolToV                                                               21 Nov 93
                                                                              14:49:11
                                                  Microsoft (R) QuickBASIC Compiler Version 4.50

FUNCTION VolToV (Opt AS INTEGER, Volt)

'Sept 29/93
   '--------------------------------------------------
   'Function Library for Ohio 7000 Ventilator Control
   '--------------------------------------------------

'Based on observations of Litre/Min Volume control
   '   Y  =   a   +    bX
   '   mV = 66.19015 + 66.71872 * Vol     R^2=0.998923

'   V = 6.61901478E-02 + 6.67187192E-02 * Vol     R^2=9.98922670E-01

'   Vol      Regression Output:
   '   Constant                          6.61901478E-02
   '   Std Err of Y Est                  1.89986311E-02
   '   R Squared                         9.98922670E-01
   '   No. of Observations                           29
   '   Degrees of Freedom                            27
   '
   '   X Coefficient(s)     6.67187192E-02
   '   Std Err of Coef.     4.21671541E-04

DIM V, Vol, a, b

'   V = 6.61901478E-02 + 6.67187192E-02 * Vol     R^2=9.98922670E-01
   a = .06619014788#
   b = .0667187192#

SELECT CASE Opt%
      CASE 1          'Volt to Vol
         V = Volt
         Vol = (V - a) / b     ' x = (Y - a) / b
         VolToV = Vol
      CASE 2          'Vol to V
         Vol = Volt
         V = a + b * Vol       ' y = a + bx
         VolToV = V
   END SELECT

END FUNCTION

43949 Bytes Available
28608 Bytes Free

0 Warning Error(s)
   0 Severe  Error(s)
```

TABLE 3

| Variable | Control Ventilator | Computer Ventilator | p-value |
|---|---|---|---|
| Weight (kg) | 21.7 ± 2.8 | 23.4 ± 1.3 | ns |
| Oleic Acid Infused (ml/kg) | 0.20 ± 0.05 | 0.24 ± 0.11 | ns |
| Mean Airway Pressure (cm $H_2O$) | 12.02 ± 0.54 | 11.41 ± 0.39 | ns |
| Mean Peak Airway Pressure (cm $H_2O$) | 59.5 ± 1.3 | 56.6 ± 3.0 | ns |
| Wet:Dry Weight Ratio | 10.1 ± 1.1 | 9.2 ± 1.2 | ns |

Mean ± S.D.
Control Group n = 6
Computer Group n = 7 except for mean airway pressure and mean peak airway pressure
Control Group n = 4
Computer Group n = 3

TABLE 4

| | | Time (minutes) Following Oleic Acid Infusion | | | | | | |
|---|---|---|---|---|---|---|---|---|
| Variable | Baseline | 0 | 30 | 60 | 90 | 120 | 150 | 180 |
| Temp (°C.) | | | | | | | | |
| Computer | 37.8 ± 1.0 | 38.3 ± 1.0* | 38.4 ± 1.1* | 38.5 ± 1.0* | 38.4 ± 0.9* | 38.5 ± 1.0* | 38.6 ± 1.1* | 38.6 ± 1.3* |
| Control | 37.2 ± 1.2+ | 38.0 ± 1.2* | 38.3 ± 1.1* | 38.4 ± 1.2* | 38.5 ± 1.0* | 38.5 ± 1.4* | 38.9 ± 1.2* | 39.0 ± 1.3* |
| Temp (°C.) | | | | | | | | |
| Computer | 36.8 ± 0.6 | 37.0 ± 0.9 | 37.3 ± 0.6 | 37.1 ± 0.8 | 37.3 ± 0.5 | 37.2 ± 0.5 | 37.2 ± 0.7 | 37.2 ± 1.1 |
| Control | 36.4 ± 1.2 | 37.1 ± 1.1* | 37.5 ± 0.9* | 37.3 ± 0.7* | 37.4 ± 0.8* | 37.7 ± 0.7* | 37.7 ± 1.0* | 37.9 ± 1.0* |
| Hgb (g %) | | | | | | | | |
| Computer | 9.2 ± 1.0 | 11.6 ± 1* | 11.8 ± 8* | 11.9 ± .7* | 11.6 ± .7* | 11.7 ± .5* | 11.8 ± .8* | 12.3 ± .7* |
| Control | 10.0 ± .9+ | 12.6 ± 1*+ | 13.0 ± 1*+ | 13.3 ± 1.3*+ | 13.7 ± 1*+ | 13.9 ± 1*+ | 14.1 ± 1*+ | 14.5 ± .8*+ |
| pH | | | | | | | | |
| Computer | 7.49 ± .03 | 7.37 ± .04* | 7.38 ± .05* | 7.36 ± .07* | 7.38 ± .06*+ | 7.37 ± .04*+ | 7.37 ± .04*+ | 7.34 ± .05*+ |
| Control | 7.48 ± .04 | 7.38 ± .03* | 7.35 ± .02* | 7.33 ± .02* | 7.33 ± .03* | 7.33 ± .03* | 7.31 ± .06* | 7.29 ± .07* |

Mean ± S.D.
*P < 0.05 within Groups
+P < 0.05 between Groups
Bonferroni's correction applied for multiple comparisons
Computer Group n = 7
Control Group n = 6
Temp = blood temperature
Temp = nasopharyngeal temperature

TABLE 5

| | | Time (minutes) Following Oleic Acid Infusion | | | | | | |
|---|---|---|---|---|---|---|---|---|
| Variable | Baseline | 0 | 30 | 60 | 90 | 120 | 150 | 180 |
| MAP (mm Hg) | | | | | | | | |
| Computer | 91 ± 15 | 78 ± 11*+ | 75 ± 14* | 75 ± 12* | 73 ± 10* | 75 ± 12* | 76 ± 9* | 77 ± 8* |
| Control | 92 ± 14 | 68 ± 16* | 69 ± 20* | 71 ± 14* | 71 ± 15* | 78 ± 19* | 79 ± 20* | 78 ± 17* |
| MPAP (mm Hg) | | | | | | | | |
| Computer | 22 ± 5 | 40 ± 4* | 39 ± 3* | 39 ± 5* | 37 ± 5* | 39 ± 6* | 40 ± 7* | 42 ± 4* |
| Control | 19 ± 2+ | 37 ± 4* | 37 ± 6* | 40 ± 5* | 40 ± 3*+ | 40 ± 5* | 43 ± 2* | 43 ± 3* |
| PCWP (mm Hg) | | | | | | | | |
| Computer | 10 ± 1 | 11 ± 1 | 11 ± .6 | 10 ± 1 | 10 ± .5 | 11 ± 1 | 12 ± 3 | 11 ± 3 |
| Control | 11 ± 1 | 12 ± 1 | 11 ± 2 | 11 ± 1 | 11 ± .8 | 10 ± 1 | 10 ± 2+ | 10 ± 1 |
| PVR (mm Hg · $l^{-1}$ min) | | | | | | | | |
| Computer | 3 ± 1 | 12 ± 1* | 12 ± 2* | 12 ± 2* | 10 ± 2* | 12 ± 4* | 12 ± 5* | 11 ± 4* |
| Control | 2 ± .7 | 13 ± 4* | 13 ± 6* | 15 ± 6* | 14 ± 5*+ | 15 ± 5*+ | 15 ± 7*+ | 15 ± 5*+ |
| CO (l · $min^{-1}$) | | | | | | | | |
| Computer | 4.2 ± .3 | 2.5 ± .4* | 2.6 ± .4* | 2.5 ± .4* | 2.6 ± .3* | 2.5 ± .3* | 2.5 ± .4* | 2.7 ± .4* |

TABLE 5-continued

| | | Time (minutes) Following Oleic Acid Infusion | | | | | | |
|---|---|---|---|---|---|---|---|---|
| Variable | Baseline | 0 | 30 | 60 | 90 | 120 | 150 | 180 |
| Control | 4.0 ± .9 | 2.4 ± .6* | 2.5 ± .9* | 2.5 ± .9* | 2.3 ± .6* | 2.5 ± .8* | 2.5 ± 1.0* | 2.5 ± .8* |

Mean ± S.D.
*P < 0.05 within Groups
+P < 0.05 between Groups
Bonferroni's correction applied for multiple comparisons
Computer Group n = 7
Control Group n = 6
MPAP = Mean Pulmonary Artery Pressure
PCWP = Pulmonary Capillary Wedge Pressure
PVR = Pulmonary Vascular Resistance
CO = Cardiac Output

TABLE 6

| | | Time (minutes) Following Oleic Acid Infusion | | | | | | |
|---|---|---|---|---|---|---|---|---|
| Variable | Baseline | 0 | 30 | 60 | 90 | 120 | 150 | 180 |
| $PeCO_2$ (mm Hg) | | | | | | | | |
| Computer | 17.5 ± 4.8 | 13.7 ± 2.6 | 14.4 ± 2.5 | 16.1 ± 3.2 | 14.7 ± 2.9 | 15.0 ± 2.2 | 13.1 ± 2.3 | 15.2 ± 2.7 |
| Control | 19.8 ± 3.7 | 16.1 ± 4.1 | 14.5 ± 2.5 | 15.4 ± 3.6 | 15.7 ± 3.8 | 16.8 ± 4.9 | 17.8 ± 6.8 | 17.3 ± 6.1 |
| $PaCO_2$ (mm Hg) | | | | | | | | |
| Computer | 36.3 ± 2 | 46.6 ± 3* | 45.3 ± 6* | 47.7 ± 8* | 45.8 ± 8* | 46.0 ± 4* | 46.8 ± 6* | 49.9 ± 6* |
| Control | 36.9 ± 2 | 43.6 ± 1* | 46.1 ± 4* | 48.2 ± 7* | 48.1 ± 3* | 49.0 ± 5* | 49.0 ± 7* | 51.2 ± 13* |
| $PaO_2$ (mm Hg) | | | | | | | | |
| Computer | 558 ± 31 | 133 ± 39* | 140 ± 68* | 158 ± 93* | 203 ± 88* | 197 ± 124* | 162 ± 119* | 116 ± 64* |
| Control | 556 ± 57 | 112 ± 56* | 103 ± 56* | 92 ± 51*+ | 90 ± 53*+ | 75 ± 20*+ | 65 ± 10*+ | 65 ± 15* |
| QS/QT | | | | | | | | |
| Computer | 10.0 ± 4.6 | 18.4 ± 3.9* | 17.4 ± 4.0* | 16.8 ± 4.1* | 15.9 ± 3.5* | 15.9 ± 4.2* | 16.7 ± 3.4* | 17.8 ± 3.9* |
| Control | 9.0 ± 3.0 | 18.6 ± 4.6* | 19.0 ± 5.7* | 17.7 ± 3.3* | 17.9 ± 4.1* | 18.3 ± 4.0* | 17.6 ± 4.6* | 18.3 ± 5.1* |
| VD/VT | | | | | | | | |
| Computer | 52.1 ± 10.2 | 70.5 ± 5.8* | 68.0 ± 5.2 | 66.0 ± 5.0* | 67.5 ± 6.1* | 67.3 ± 5.2* | 71.6 ± 5.3* | 69.6 ± 4.1* |
| Control | 45.6 ± 12.1 | 63.3 ± 8.5* | 68.3 ± 6.0* | 67.9 ± 7.4* | 67.5 ± 7.2* | 65.6 ± 8.1* | 64.4 ± 10* | 66.9 ± 4.6* |

Mean ± S.D.
*P < 0.05 within Groups
+P < 0.05 between Groups
Bonferroni's correction applied for multiple comparisons
Computer Group n = 7
Control Group n = 6
$PeCO_2$ = end expired $CO_2$
QS/QT = shunt fraction
VD/VT = dead space ventilation

TABLE 7

| Variable | Hypothermia | Rewarming |
|---|---|---|
| Temp °C. | | |
| Computer | 28.4 ± .3 | 35.6 ± .82* |
| Control | 28.0 ± .24 | 35.0 ± .91* |
| MAP (mm HG) | | |
| Computer | 91 ± 26 | 93 ± 17 |
| Control | 81 ± 13 | 82 ± 10+ |
| CSFP (mm Hg) | | |
| Computer | 9.1 ± 3 | 14.6 ± 3.7* |
| Control | 8.2 ± 4.3 | 12.3 ± 4.1*+ |
| CPP (mm Hg) | | |
| Computer | 82 ± 26 | 80 ± 19 |
| Control | 72 ± 15 | 69 ± 11 |

TABLE 7-continued

| Variable | Hypothermia | Rewarming |
|---|---|---|
| Computer n = 6 | | |
| Control n = 6 | | |
| *p < 0.05 within groups | | |
| +p < 0.05 between groups | | |

TABLE 8

| Variable | Hypothermia | Rewarming |
|---|---|---|
| Hgb (g/dl) | | |
| Computer | 7.4 ± .7 | 8.1 ± .9 |
| Control | 7.7 ± 1.1 | 7.7 ± 1 |
| $PaCO_2$ (mm Hg) | | |
| Computer | 37 ± 2 | 36 ± 1 |

TABLE 8-continued

| Variable | Hypothermia | Rewarming |
|---|---|---|
| Control | 38 ± 2 | 36 ± 6 |
| pH | | |
| Computer | 7.35 ± .01 | 7.35 ± .02 |
| Control | 7.33 ± .02 | 7.35 ± .08 |
| Cont Diff (Vol %) | | |
| Computer | 4.4 ± 1.2 | 4.3 ± 1.1 |
| Control | 3.6 ± 0.7 | 4.9 ± 1.1* |
| SSS PO$_2$ (mm Hg) | | |
| Computer | 44 ± 6 | 42 ± 7* |
| Control | 44 ± 3 | 38 ± 4*+ |
| SSS Sat (%) | | |
| Computer | 68 ± 11 | 67 ± 10 |
| Control | 69 ± 6 | 60 ± 7*+ |

Computer n = 6
Control n = 6
*p < 0.05 within groups
+p < 0.05 between groups

TABLE 9

| Variable | Hypothermia | Rewarming |
|---|---|---|
| tCBF (ml · g$^{-1}$ · min$^{-1}$) | | |
| Computer | .18 ± .08 | .36 ± .07* |
| Control | .17 ± .06 | .33 ± .06* |
| hCBF (ml · g$^{-1}$ · min$^{-1}$) | | |
| Computer | .17 ± .1 | .35 ± .08* |
| Control | .17 ± .06 | .32 ± .06* |
| bsCBF (ml · g$^{-1}$ · min$^{-1}$) | | |
| Computer | .21 ± .11 | .41 ± .07* |
| Control | .20 ± .07 | .38 ± .08* |
| FLOW:METABOLISM | | |
| Computer | 23.1 ± 5.2 | 23.9 ± 5.0 |
| Control | 28.6 ± 5.6 | 22.3 ± 4.3* |
| CMRO$_2$ | | |
| Computer | .008 ± .004 | .016 ± .008* |
| Control | .006 ± .002 | .014 ± .002* |

Computer n = 6
Control n = 6
*p < 0.005 within groups
+p < 0.005 between groups

What we claim is:

1. A method of controlling flow of a biological fluid to an organ during controlled life support conditions, said biological fluid being the primary source of fluid to sustain life support to an organ, wherein said method which comprises:

establishing a predetermined pattern of variations over time of instantaneous changes in flow of a biological fluid to an independently-functioning normal organ of a mammalian species, generating a variable control parameter for regulation of flow of said biological fluid to an organ during controlled life support conditions in accordance with said predetermined pattern, and controlling said flow of said biological fluid to said organ during controlled life support conditions in accordance with said variable control parameter to provide a variable flow of said biological fluid to the organ during controlled life support conditions which mimics the normal flow of said biological fluid to a normal organ.

2. A method of controlling flow of ventilating gas from a ventilator device to the lungs of a body during controlled life support conditions, said biological fluid being the primary source of fluid to sustain life support to an organ, wherein said method comprises:

establishing a predetermined pattern of variation over time of instantaneous respiratory rate and tidal volume of the independently-functioning normal lungs of a mammalian species, generating a signal corresponding in value to an individually-determined respiratory rate and tidal volume in said predetermined pattern, generating a control voltage corresponding in magnitude to said signal, applying said control voltage to said ventilator device to provide an output of ventilating gas from said ventilating device of a respiratory rate proportional to the magnitude of said signal, and repeating said steps of generating a signal, generating a control voltage and applying said control voltage to said ventilator device for each next individually-determined respiratory rate of said predetermined pattern, to provide a variable flow of ventilating gas from the ventilator device to the lungs of the body under controlled life support conditions which mimics normal breathing of healthy lungs.

3. Apparatus for controlling the flow of a biological fluid to an organ, said biological fluid being the primary source of fluid to sustain life support to an organ, wherein said method comprises:

means for establishing a predetermined pattern of variations over time of instantaneous changes in flow of a biological fluid to an independently-functioning normal organ of a mammalian species, means for generating a variable control parameter for regulation of flow of the biological fluid to an organ during controlled life support conditions in accordance with the predetermined pattern, and means for controlling the flow of the biological fluid to the organ during controlled life support conditions in accordance with the variable control parameter to provide a variable flow of said biological fluid to the organ during controlled life support conditions which mimics the normal flow of said biological fluid to a normal organ.

* * * * *